(12) United States Patent
Molldrem et al.

(10) Patent No.: US 11,192,958 B2
(45) Date of Patent: Dec. 7, 2021

(54) MONOCLONAL ANTIBODIES FOR USE IN DIAGNOSIS AND THERAPY OF CANCERS AND AUTOIMMUNE DISEASE

(71) Applicant: Board of Regents, The University of Texas System, Austin, TX (US)

(72) Inventors: Jeffrey Molldrem, Houston, TX (US); Anna Sergeeva, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 717 days.

(21) Appl. No.: 15/895,782

(22) Filed: Feb. 13, 2018

(65) Prior Publication Data

US 2018/0371106 A1    Dec. 27, 2018

Related U.S. Application Data

(62) Division of application No. 14/413,833, filed as application No. PCT/US2013/049368 on Jul. 3, 2013, now Pat. No. 9,926,380.

(60) Provisional application No. 61/702,916, filed on Sep. 19, 2012, provisional application No. 61/669,967, filed on Jul. 10, 2012.

(51) Int. Cl.
| | | |
|---|---|---|
| A61K 39/00 | (2006.01) | |
| A61K 47/68 | (2017.01) | |
| C07K 16/28 | (2006.01) | |
| C07K 16/40 | (2006.01) | |
| C07K 16/30 | (2006.01) | |
| A61K 45/06 | (2006.01) | |
| G01N 33/574 | (2006.01) | |

(52) U.S. Cl.
CPC .............. *C07K 16/40* (2013.01); *A61K 45/06* (2013.01); *A61K 47/6851* (2017.08); *A61K 47/6871* (2017.08); *C07K 16/2833* (2013.01); *C07K 16/30* (2013.01); *C07K 16/3061* (2013.01); *G01N 33/57488* (2013.01); *A61K 39/00* (2013.01); *C07K 2317/24* (2013.01); *C07K 2317/32* (2013.01); *C07K 2317/34* (2013.01); *C07K 2317/567* (2013.01); *C07K 2317/71* (2013.01); *C07K 2317/73* (2013.01); *C07K 2317/92* (2013.01); *G01N 2333/96433* (2013.01)

(58) Field of Classification Search
None
See application file for complete search history.

(56) References Cited

U.S. PATENT DOCUMENTS

| | | | |
|---|---|---|---|
| 6,534,633 B1 | 3/2003 | Weidanz et al. | |
| 7,074,904 B2 | 7/2006 | Wong et al. | |
| 7,456,263 B2 | 11/2008 | Sherman et al. | |
| 7,713,524 B2 | 5/2010 | Bourel et al. | |
| 8,105,830 B2 | 1/2012 | Weidanz et al. | |
| 8,158,385 B2 | 4/2012 | Ozaki et al. | |
| 2006/0045881 A1 | 3/2006 | Molldrem | |
| 2006/0045884 A1 | 3/2006 | Molldrem | |
| 2006/0167230 A1 | 7/2006 | Koga et al. | |
| 2007/0280951 A1 | 12/2007 | Kimura et al. | |
| 2009/0022687 A1 | 1/2009 | Matsumoto et al. | |
| 2009/0233318 A1 | 9/2009 | Weidanz | |
| 2009/0304679 A1 | 12/2009 | Weidanz | |
| 2010/0003254 A1 | 1/2010 | Hattori et al. | |
| 2010/0092461 A1 | 4/2010 | Matsumoto et al. | |
| 2010/0150927 A1 | 6/2010 | Kimura et al. | |
| 2010/0291102 A1 | 11/2010 | Dalgleish et al. | |
| 2011/0293620 A1 | 12/2011 | Molldrem et al. | |
| 2011/0293623 A1 | 12/2011 | Weidanz | |
| 2011/0318369 A1 | 12/2011 | Reiter et al. | |
| 2012/0121577 A1 | 5/2012 | Weidanz et al. | |

FOREIGN PATENT DOCUMENTS

| | | |
|---|---|---|
| EP | 1561759 | 8/2005 |
| EP | 1712565 | 10/2006 |
| EP | 1927367 | 6/2008 |
| EP | 2048230 | 4/2009 |
| EP | 2072045 | 6/2009 |
| EP | 2481755 | 8/2012 |
| WO | WO 1991/012332 | 8/1991 |
| WO | WO 2007/030451 | 3/2007 |
| WO | WO 2009/073163 | 6/2009 |
| WO | WO 2010/065962 | 6/2010 |

OTHER PUBLICATIONS

Dubrovsky et al. (OncoImmunol. 5:1, e1049803, 2015) (Year: 2015).*
Qazilbash et al. (Blood, 2004, 11: 259, meeting abstract) (Year: 2004).*
Alatrash et al., "Broad cross-presentation of the hematopoietically derived PR1 antigen on solid tumors leads to susceptibility to PR1-targeted immunotherapy," *The Journal of Immunology*, 189:5476-5484, 2012.
Burchert, et al., "Interferon-alpha, but not the ABL-kinase inhibitor imatinib (STI571), and a specific T-cell response in chronic myeloid leukemia," *Blood*, 101:259-264, 2003.
Molldrem, et al., "A PR1-human leukocyte antigen-A2 tetramer can be used to isolate low-frequency cytotoxic T lymphocytes from healthy donors that selectively lyse chronic myelogenous leukemia," *Cancer Res.*, 59:2675-2681, 1999.

(Continued)

*Primary Examiner* — G. R. Ewoldt
*Assistant Examiner* — Marianne DiBrino
(74) *Attorney, Agent, or Firm* — Parker Highlander PLLC

(57) ABSTRACT

The specification describes the sequences for antibodies that recognize the HLA-A2-restricted peptide PR-1 in the context of HLA presentation on the surface of cancer cells. Use of these antibodies in the diagnosis and treatment of cancer and immune-related diseases are also provided.

9 Claims, 38 Drawing Sheets

Specification includes a Sequence Listing.

(56) References Cited

OTHER PUBLICATIONS

Molldrem, et al., "Chronic myelogenous leukemia shapes host immunity by selective deletion of high-avidity leukemia-specific T cells," *J. Clin. Invest.*, 111:639-647, 2003.

Molldrem, et al., "Cytotoxic T lymphocytes specific for a nonpolymorphic proteinase 3 peptide preferentially inhibit chronic myeloid leukemia colony-forming units," *Blood*, 90:2529-2534, 1997.

Molldrem, et al., "Evidence that specific T lymphocytes may participate in the elimination of chronic myelogenous leukemia," *Nat. Med.*, 6:1018-1023, 2000.

Molldrem, et al., "Targeted T-cell therapy for human leukemia: cytotoxic T lymphocytes specific for a peptide derived from proteinase 3 preferentially lyse human myeloid leukemia cells," *Blood*, 88:2450-2457, 1996.

Office Action issued in Chinese Application No. 201380042522.1, dated Jan. 28, 2016, and English language translation thereof.

PCT International Preliminary Report on Patentability issued in International Application No. PCT/US2013/049368, dated Jan. 13, 2015.

PCT International Preliminary Report on Patentability issued in International Application No. PCT/US2009/067017, dated Jun. 16, 2011.

PCT International Search Report and Written Opinion issued in International Application No. PCT/US2013/049368, dated Jan. 13, 2014.

PCT International Search Report and Written Opinion issued in International Application No. PCT/US2009/067017, dated Aug. 18, 2010.

Sergeeva et al., "An anti-PR1/HLA-A2 T-cell receptor-like antibody mediates complement-dependent cytotoxicity against acute myeloid leukemia progenitor cells," *Blood*, 117(16):4262-4272, 2011.

Sun, et al., "Construction and characterization of soluble HLA-A*0201-PR1 complex," *Zhongguo Shi Yan Xue Ye Xue Za Zhi*, 15:352-356, 2007, English abstract only.

* cited by examiner

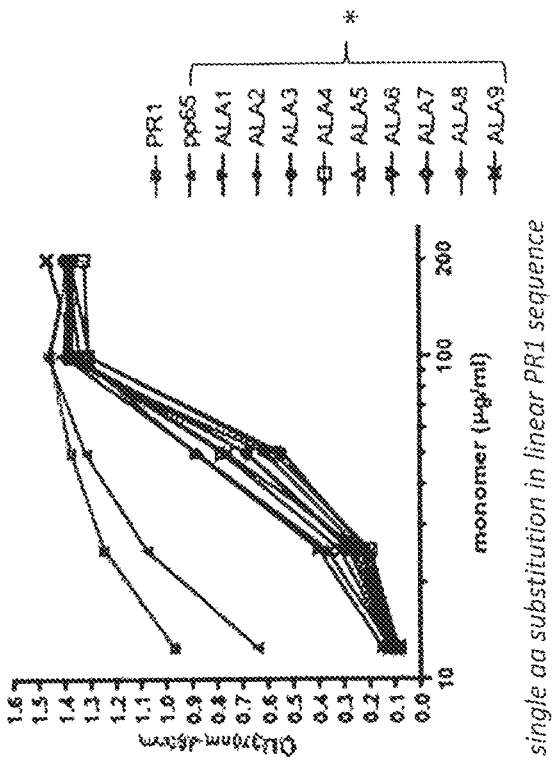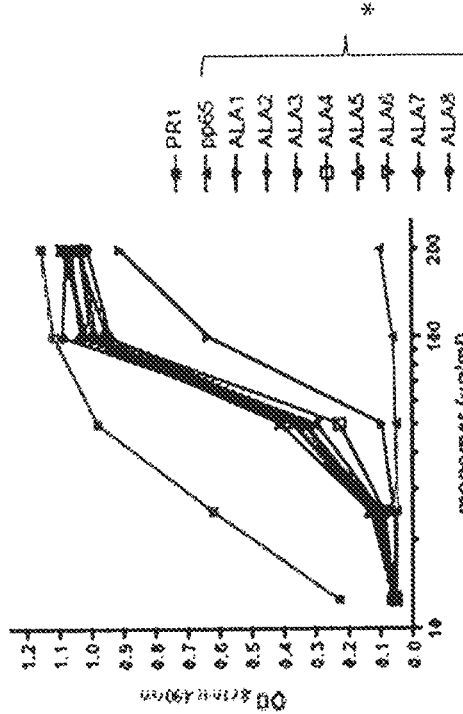
FIG. 1

FIG. 4A-B

Patient-derived AML blasts into irradiated A2-transgeneic NOD/SCID mice

Heart 400X 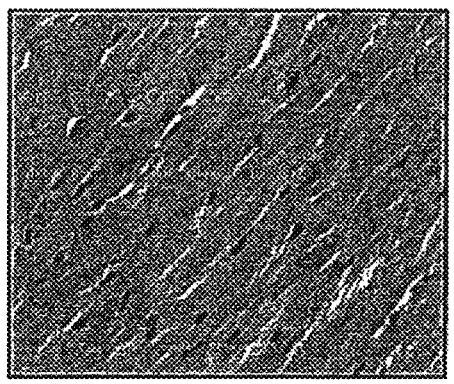
Kidney 400X 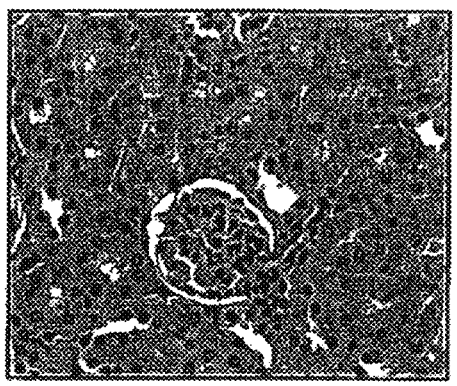
Cerebellum 400X 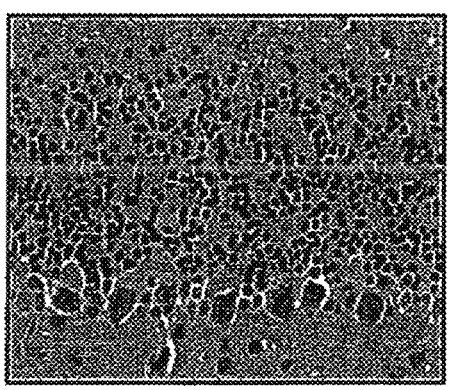
Spleen 400X 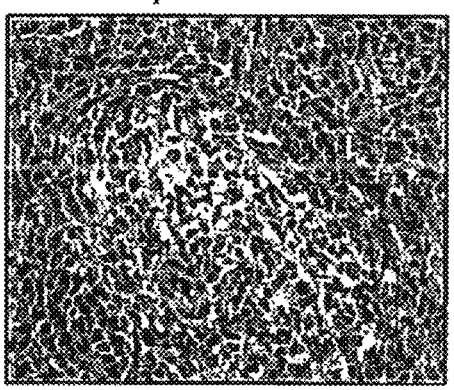
Lung 100X 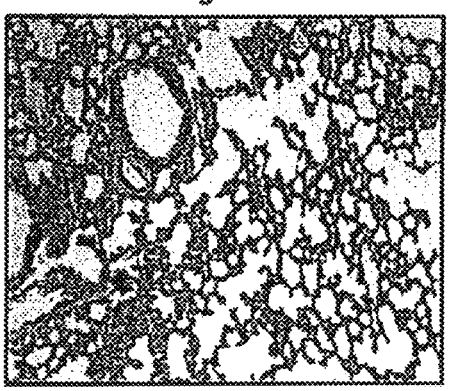
Liver 100X 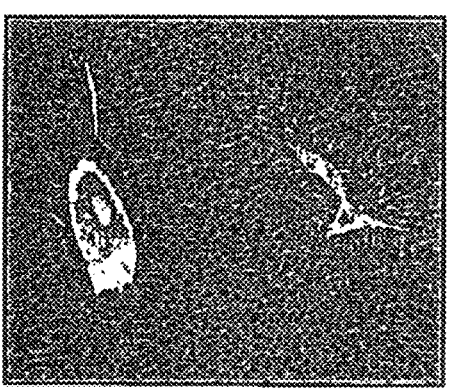
FIG. 9C

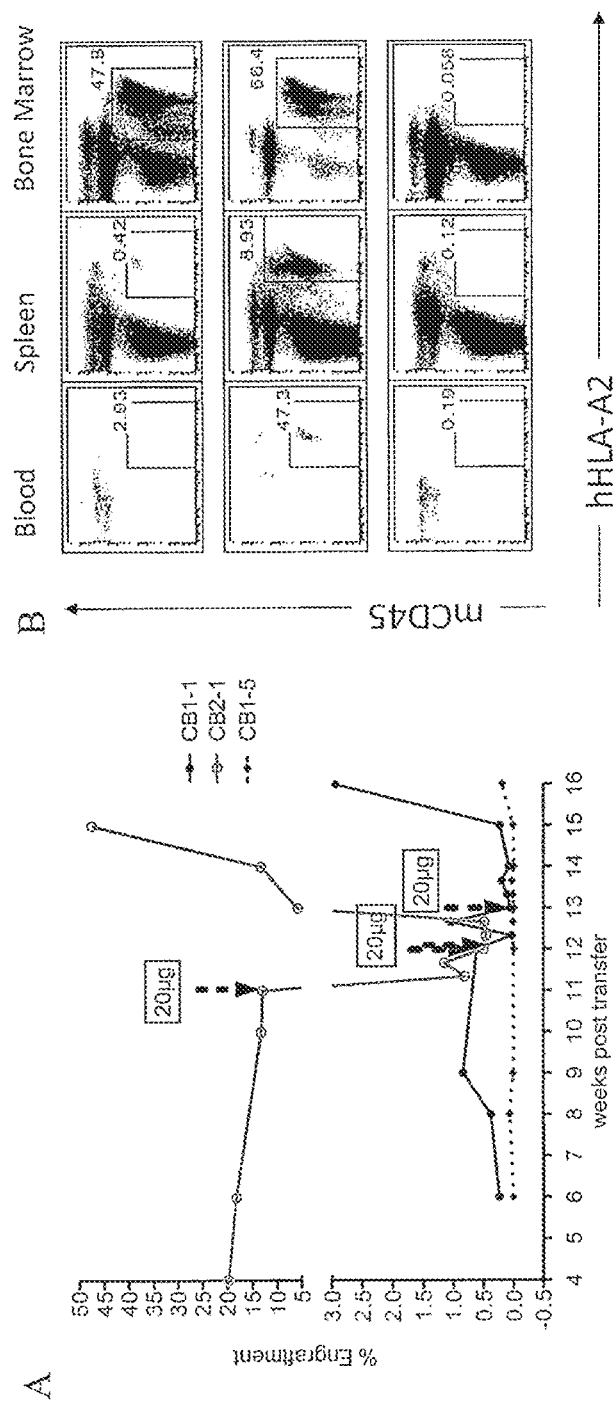
FIG. 10A-B

```
                        1           2           3
            123456789  0123456789  0123456789  0123456789
8F4    VH   EVQLVESGG  DLVKPGGSLK  LSCAASGFTF  SGYGMSWVRQ
Hu8F4  VH   EVQLVESGG  GLVQPGGSLR  LSCAASGFTF  SGYGMSWVRQ
U96282 VH   EVQLVESGG  GLVQPGGSLR  LSCAASGFTF  S-----WVRQ 4           5            6           7
            0123456789  01223456789  0123456789  0123456789
                            a
8F4    VH   TPDKRLEWVA  TISSGGSYTYY  PDSVKGRFTI  SRDNAKNTLY
Hu8F4  VH   APGKGLEWVA  TISSGGSYTYY  PDSVKGRFTI  SRDNAKNSLY
U96282 VH   APGKGLEWVA  -----------  ------RFTI  SRDNAKNSLY 1                    1
            8              9              0                    1
            0122223456789  0123456789     00000000123456789    0123
              abc                           abcdefg
8F4    VH   LQMSSLKSEDTAM  YYCARHEGGY     YGSSPAWFVYWGQGTLV    TLSA
Hu8F4  VH   LQMNSLRAEDTAV  YYCARHEGGY     YGSSPAWFVYWGQGTMV    TVSS
U96282 VH   LQMNSLRAEDTAV  YYCAR-----     ----------WGQGTMV    TVSS
```

FIG. 12

```
                              1          2          3
              123456789  0123456789 0123456789 0123456789
8F4 VL        DIVMTQSHK  FMSTSVGDRV SITCKASQDV STAVAWYQQK
Hu8F4 VL1     DIQMTQSPS  SLSASVGDRV TITCKASQDV STAVAWYQQK
Hu8F4 VL2     DIQMTQSPS  SLSASVGDRV TITCKASQDV STAVAWYQQK
AY043146 VL   DIQMTQSPS  SLSASVGDRV TITC------ -----WYQQK 4          5          6          7
              0123456789 0123456789 0123456789 0123456789
8F4 VL        PGQSPKLLIY STSYRYTGVP DRFTGSGSGT VFTFTINSVQ
Hu8F4 VL1     PGKAPKLLIY STSYRYTGVP SRFSGSGSGT VFTFTISSLQ
Hu8F4 VL2     PGKAPKLLIY STSYRYTGVP SRFSGSGSGT DFTFTISSLQ
AY043146 VL   PGKAPKLLIY --------GVP SRFSGSGSGT DFTFTISSLQ 1
              8          9                     0
              0123456789 0123456789 01234567
8F4 VL        AEDLAVYYCQ QHFITPPTFG GGTKLEIK
Hu8F4 VL1     PEDIATYYCQ QHFITPPTFG GGTKVEIK
Hu8F4 VL2     PEDIATYYCQ QHFITPPTFG GGTKVEIK
AY043146 VL   PEDIATYYC- --------FG GGTKVEIK
```

FIG. 13

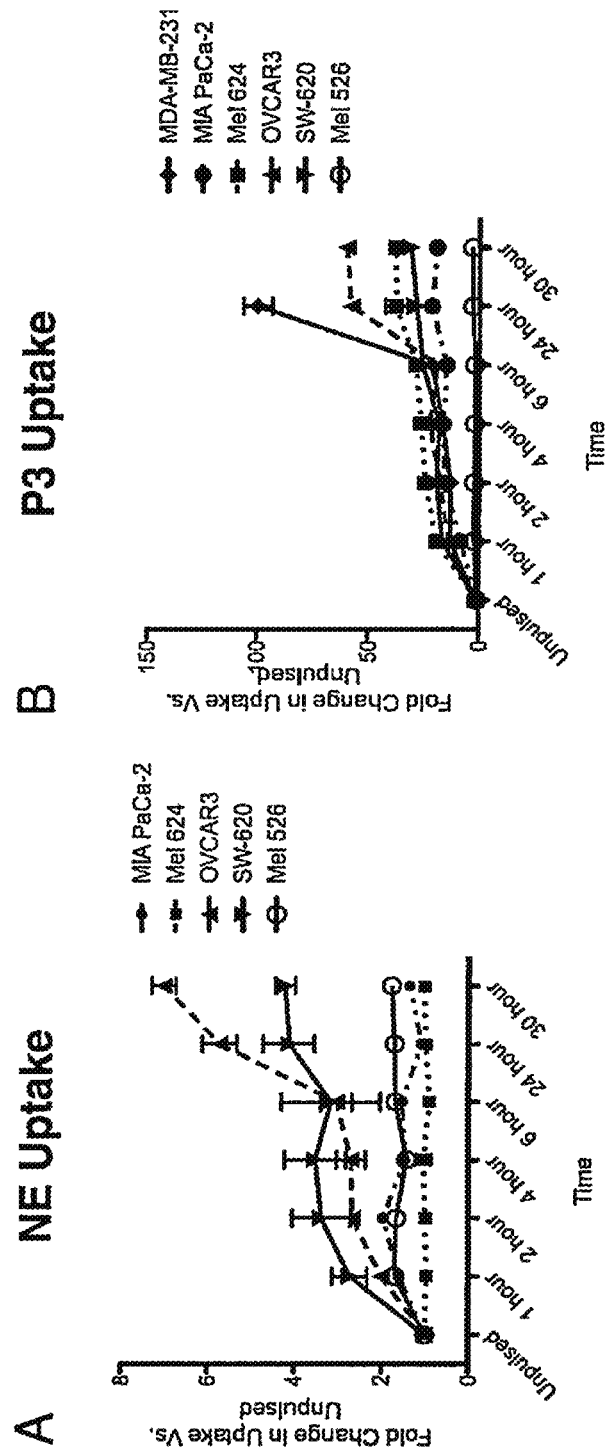
FIGS. 21A-B

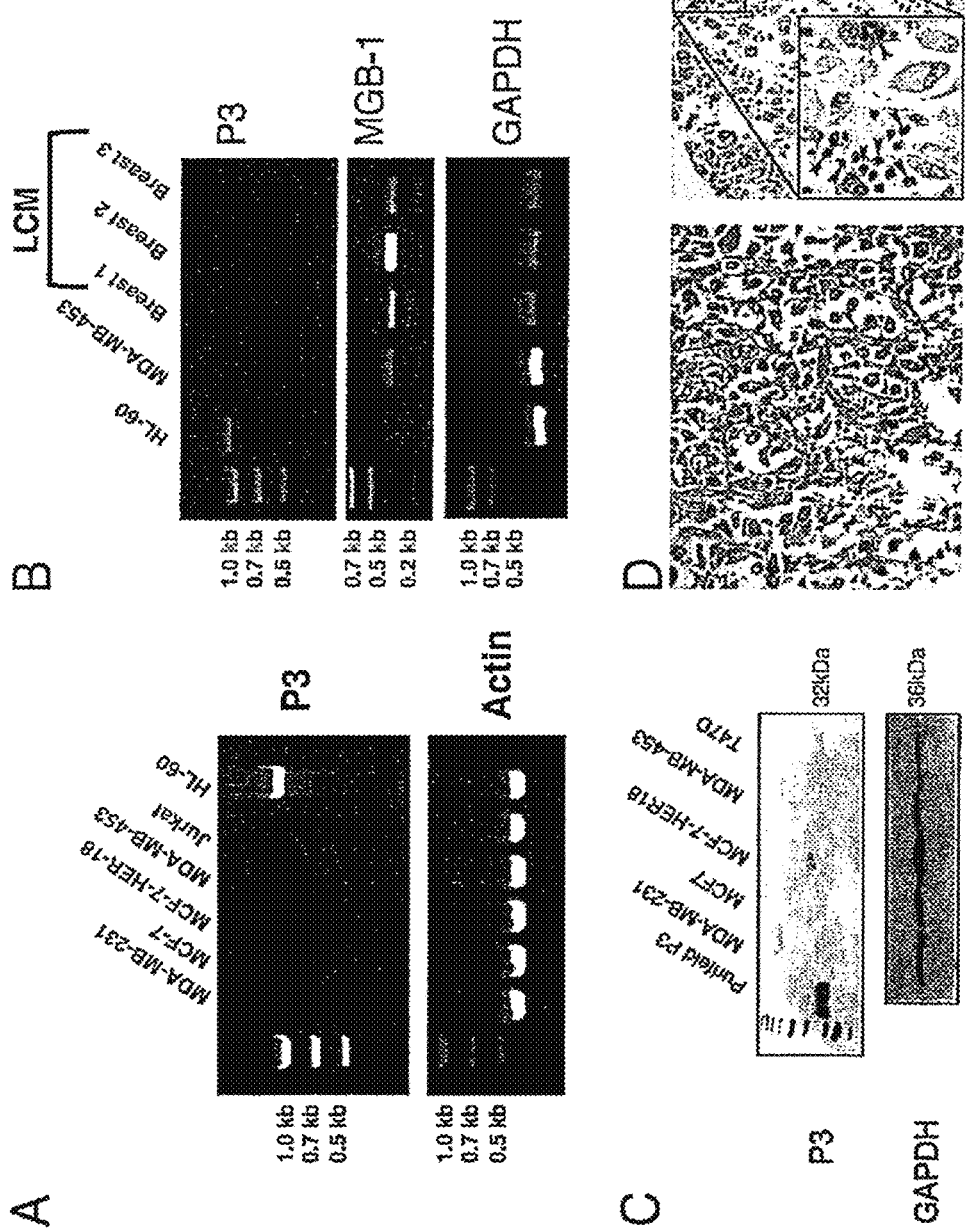
FIGS. 22A-D

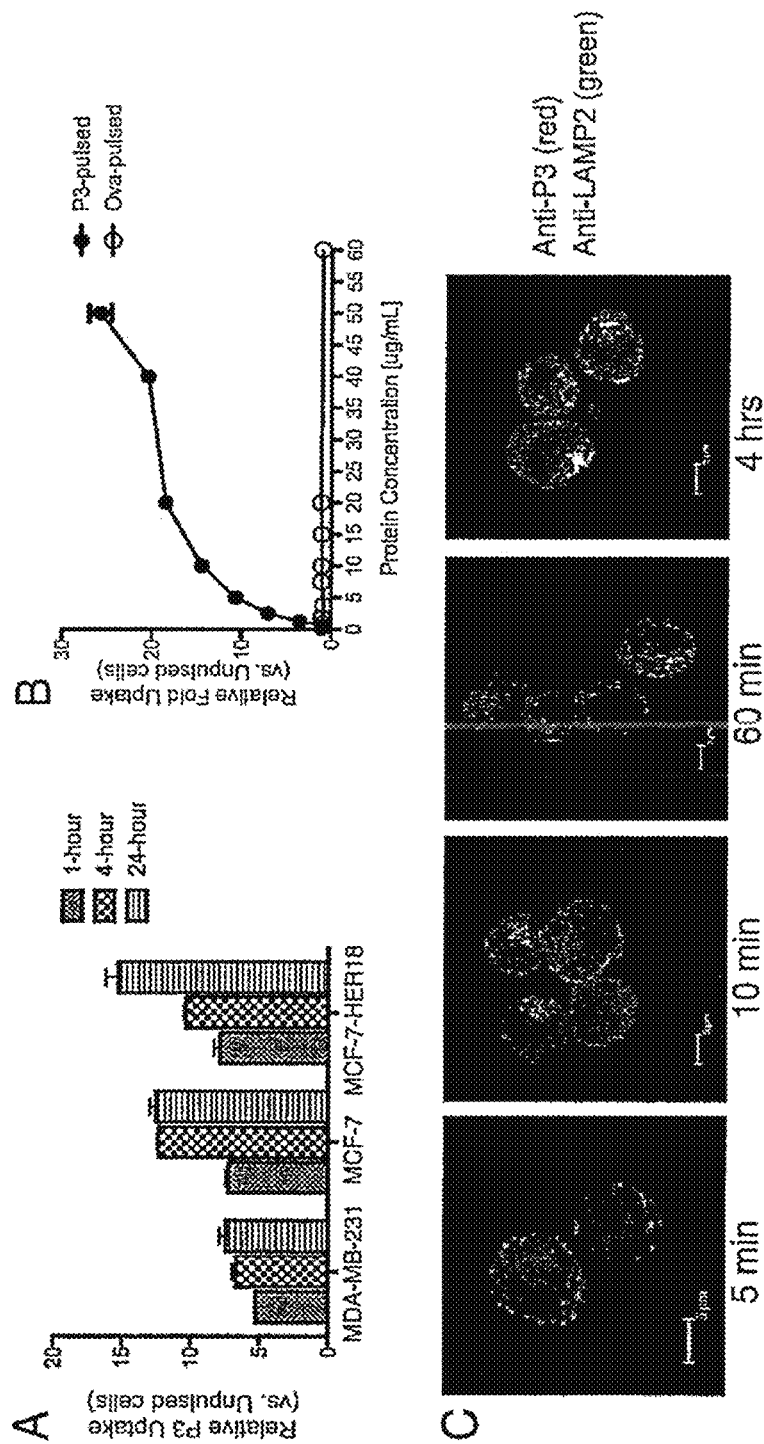
FIGS. 23A-C

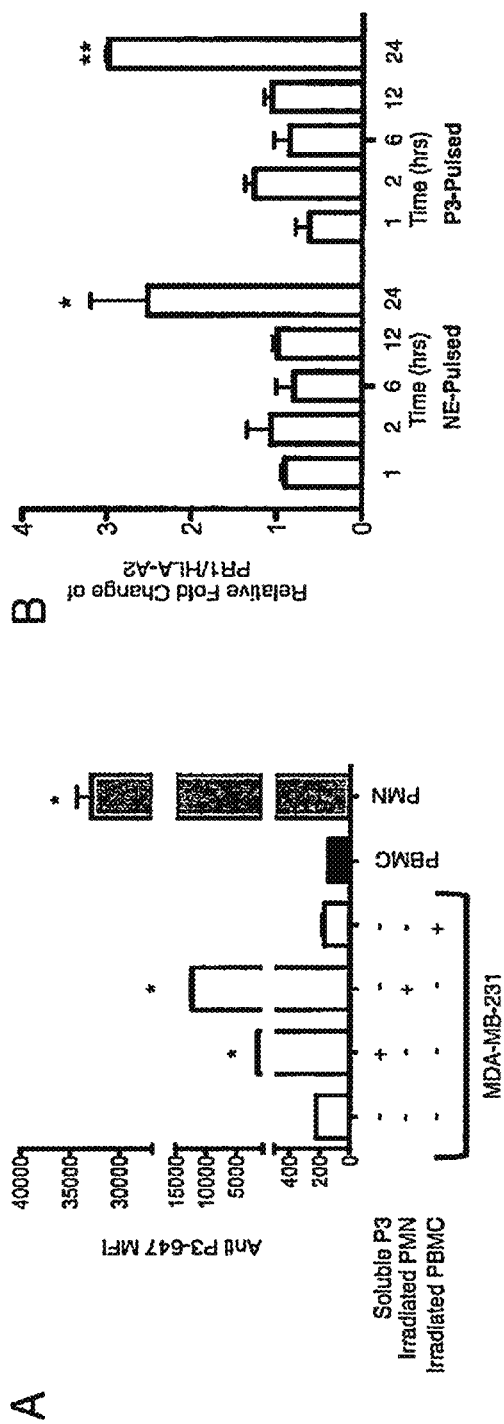
FIGS. 24A-B

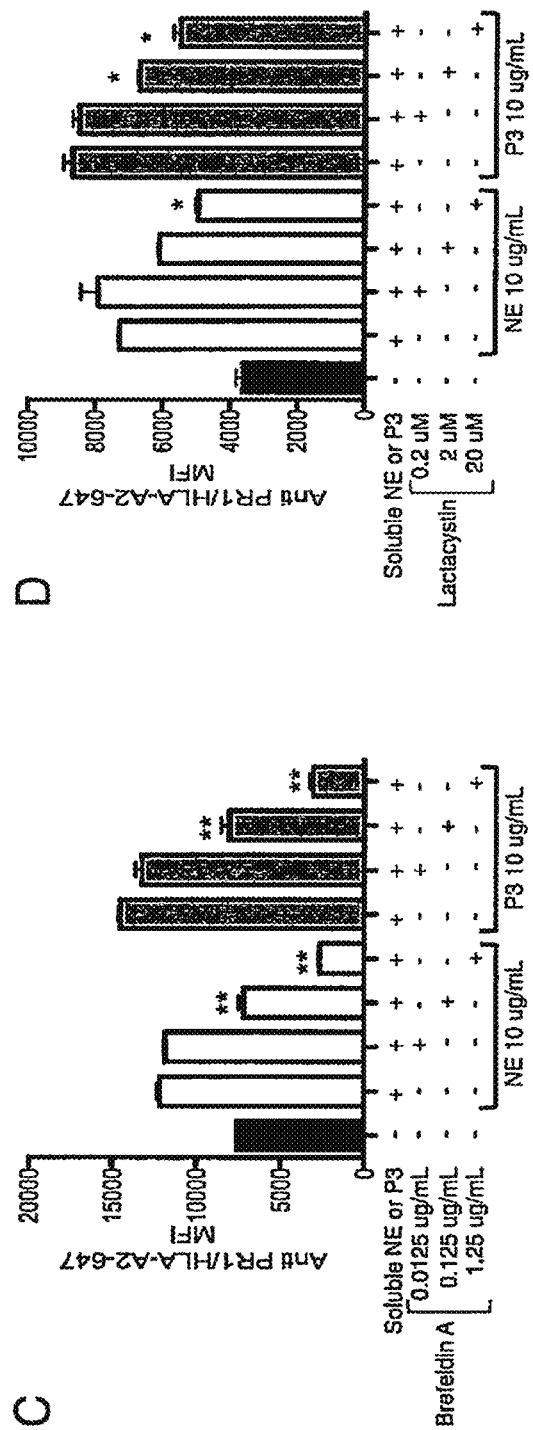
FIGS. 24C-D

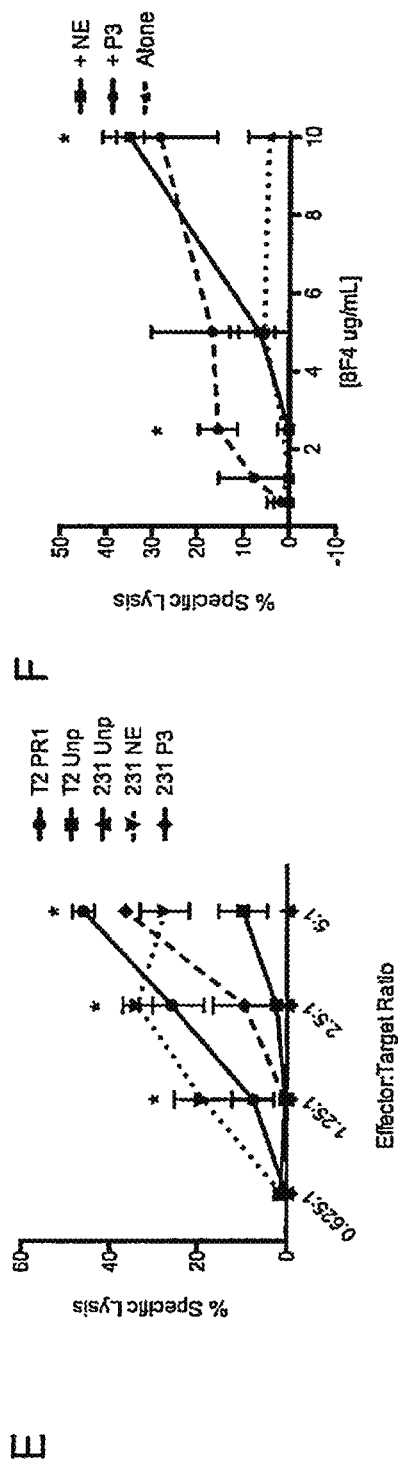
FIGS. 24E-F

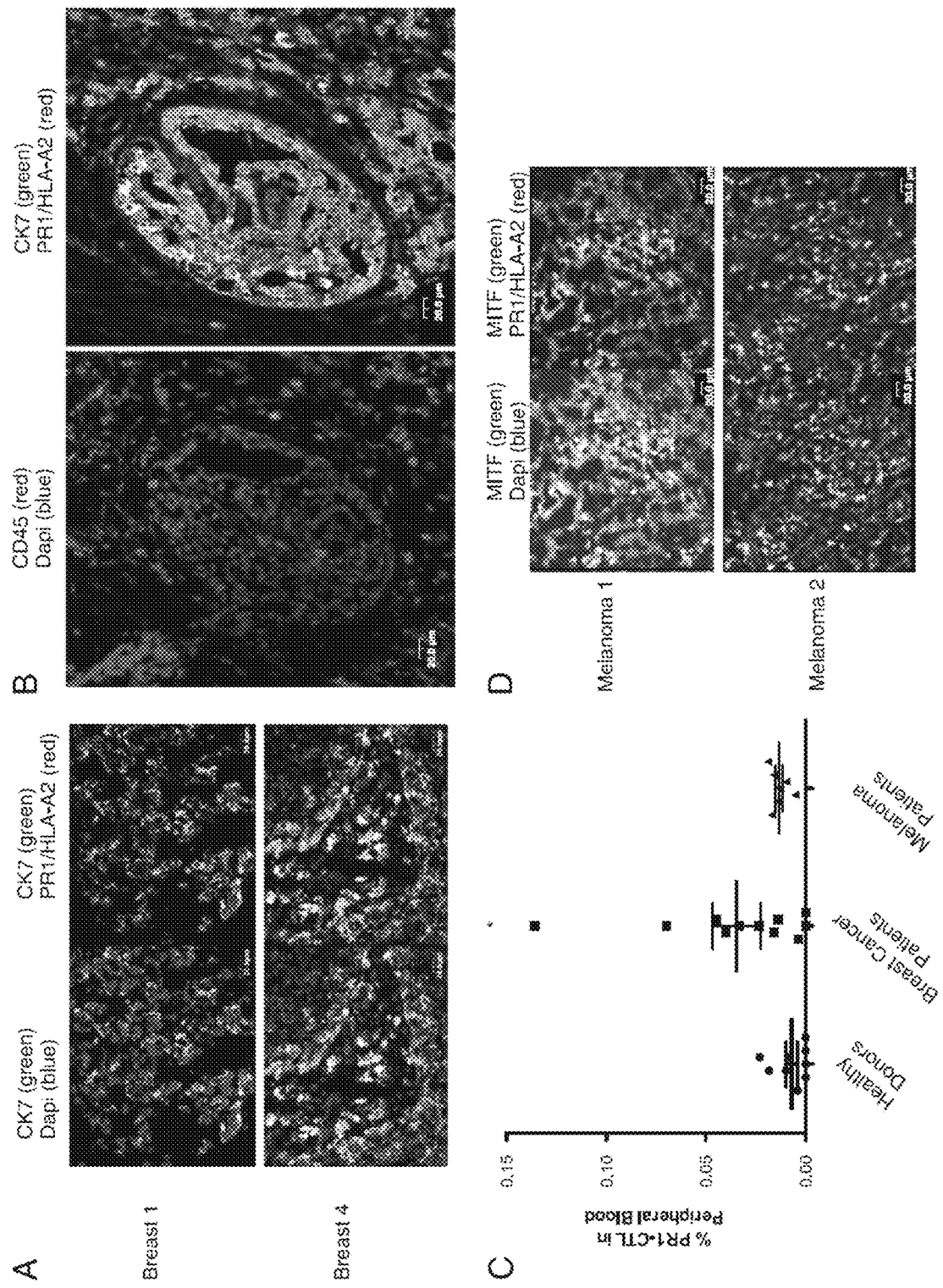
FIGS. 25A-D

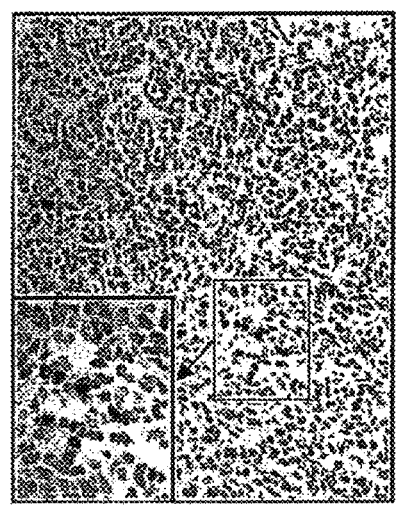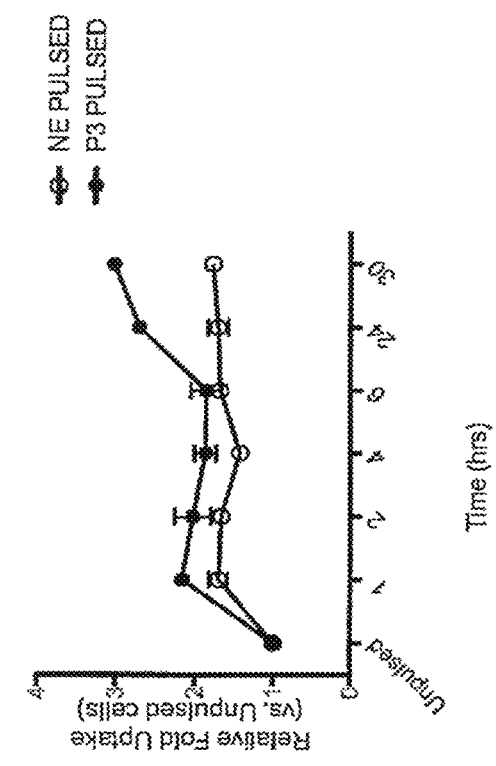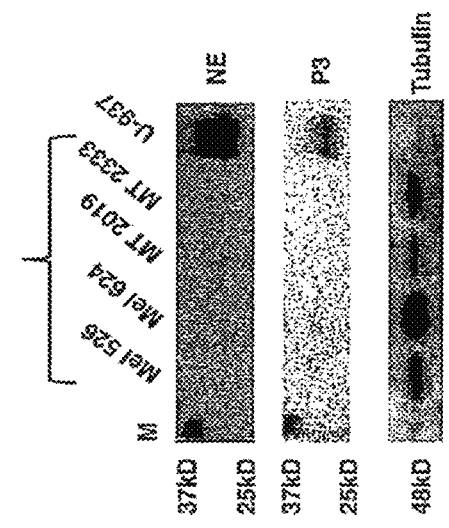
FIGS. 26A-D

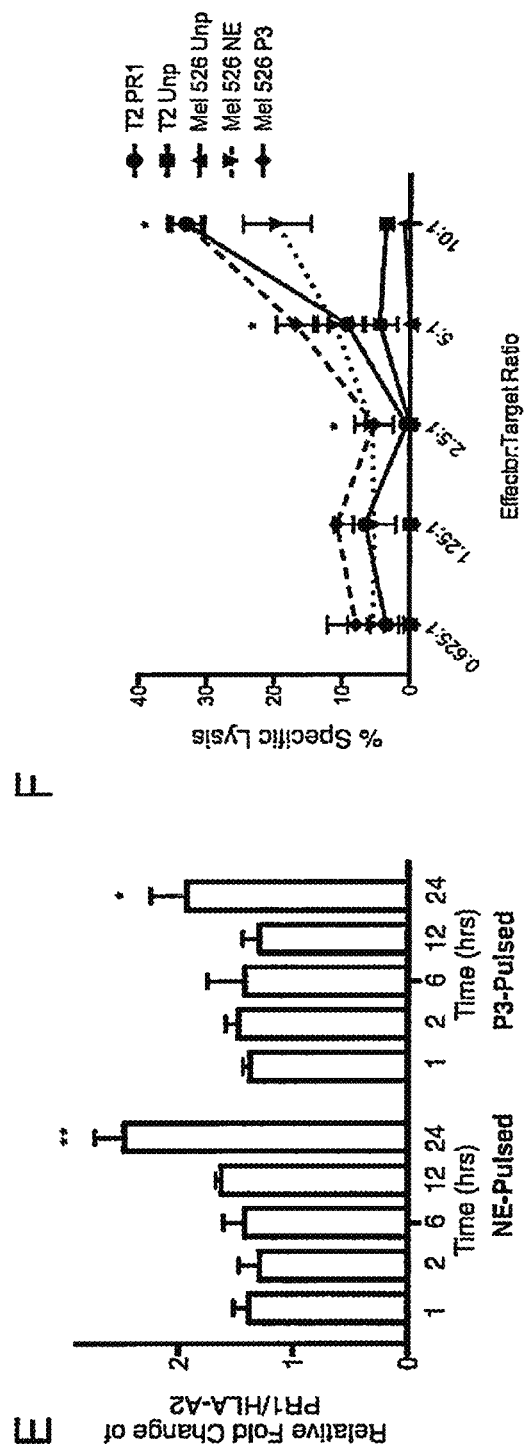
FIGS. 26E-F

MONOCLONAL ANTIBODIES FOR USE IN DIAGNOSIS AND THERAPY OF CANCERS AND AUTOIMMUNE DISEASE

The present application is a divisional of U.S. application Ser. No. 14/413,833, filed Jan. 9, 2015, which is a national phase application under 35 U.S.C. § 371 of International Application No. PCT/US2013/049368, filed Jul. 3, 2013, which claims benefit of priority to U.S. Provisional Application Ser. Nos. 61/669,967, filed Jul. 10, 2012 and 61/702,916, filed Sep. 19, 2012, the entire contents of each of the applications being hereby incorporated by reference.

This invention was made with government support under P50 CA100632 awarded by the National Cancer Institute/National Institutes of Health. The government has certain rights in the invention.

BACKGROUND OF THE INVENTION

1. Field of the Invention

The present invention relates generally to the fields of cancer and immunotherapy. More particularly, it concerns immunodiagnostic and immunotherapeutic antibodies for the treatment and prevention of cancer and autoimmune disease.

2. Description of Related Art

The immune system has long been implicated in the control of cancer; however, evidence for specific and efficacious immune responses in human cancer have been lacking. In chronic myelogenous leukemia (CIVIL), either allogeneic bone marrow transplant (BMT) or interferon-α2b (IFN-α2b) therapy have resulted in complete remission, but the mechanism for disease control is unknown and may involve immune antileukemic responses.

Based on evidence in the art, it is thought that lymphocytes play a role in meditating an antileukemia effect. Studies have demonstrated that allogeneic donor lymphocyte infusions (DLI) have been used to treat relapse of myeloid leukemia after allogeneic BMT (Giralt and Kolb, 1996; Kolb and Holler, 1997; Kolb et al., 1995; Kolb et al., 1996; Antin, 1993). Lymphocyte transfusion from the original bone marrow (BM) donor induces both hematological and cytogenetic responses in approximately 70% to 80% of patients with chronic myelocytic leukemia (CML) in chronic phase (CP) (Kolb et al., 1996, Kolb and Holler, 1997). Remissions after DLI for AML are generally not as durable as those obtained in chronic phase CML, which may reflect the rapid kinetics of tumor growth outpacing the kinetics of the developing immune response. Additionally, most patients with myeloid forms of leukemia will die from the disease unless they can be treated with allogeneic bone marrow transplant, where the associated graft versus leukemia (GVL) effect cures patients. However, graft-versus-host disease (GVHD) and transplant-related toxicity limit this treatment. It is believed that GVL may be separable from GHVD, and that targeting the immune response toward leukemia-associated antigens will allow for the transfer of GVL to patients without GVHD.

Thus, if more antigens (i.e., leukemia antigens or antigens against other cancers) could be determined, and if large numbers of the most potent antigen-specific cytotoxic T lymphocytes (CTLs) could be obtained, it would allow for development of leukemia-specific therapies, breast cancer specific therapies, etc. using the antigens as a targets for vaccines or for generating specific T-cells for use in adoptive immunotherapy.

PR1, an HLAA2.1-restricted nonamer derived from proteinase 3 (P3) and elastase, was identified as a leukemia-associated antigen (Molldrem et al., 2000; Molldrem et al., 1996; Molldrem et al., 1997; Molldrem et al., 1999; Molldrem et al., 2003 each incorporated herein by reference in their entirety). The finding that PR1 is a leukemia-associated antigen has been independently confirmed by Burchert et al. (2002) and Scheibenbogen et al. (2002). CTLs that are specific for PR1 kill AML, CIVIL and MDS cells, but not normal bone marrow cells. In a recent phase I/II vaccine study, the PR1 peptide has been administered to patients with AML, CML and MDS, and PR1-specific CTL immunity has been elicited in 47% of patients, and clinical responses have been observed in 26%. Thus, this antigen provides an interesting platform for further investigation into anti-cancer immune responses as well as for the development of new therapeutic agents.

SUMMARY OF THE INVENTION

Thus, in accordance with the present invention, there is provided an isolated and purified antibody that binds to VLQELNVTV (SEQ ID NO: 45) when bound by an HLA-A2 receptor, said antibody having heavy chain CDRs including SEQ ID NOS: 3, 60 and 5, and light chain CDRs including SEQ ID NOS: 8, 9 and 10. The antibody may be a mouse antibody, a single chain antibody, a bispecific antibody, fused to a non-antibody peptide or polypeptide segment, linked to a diagnostic reagent (such as a fluorophore, a chromophore, a dye, a radioisotope, a chemiluminescent molecule, a paramagnetic ion, or a spin-trapping reagent), linked to a therapeutic reagent (such as a cytokine, a chemotherapeutic, a radiotherapeutic, a hormone, an antibody Fc fragment, a TLR agonist, a CpG-containing molecule, or an immune co-stimulatory molecule), a humanized antibody, or combinations of the above. The bispecific antibody may have, in addition to binding affinity for SEQ ID NO: 45, binding affinity for B cells (CD19, CD20), NK cells, phagocytes (CD16), or monocytes (CD14). A particular humanized antibody may have a light chain/heavy chain sequences of SEQ ID NOS: 40 and 38_or SEQ ID NOS: 42 and 38 and SEQ ID NOS: 42 and 44.

In another embodiment, there is provided a nucleic acid encoding light chain CDRs encoded by SEQ ID NOS: 8, 9 and 10. The nucleic acid may encode SEQ ID NO: 7 or SEQ ID NO: 14 or may encode SEQ ID NO: 25 or SEQ ID NO: 27. The nucleic acid may further comprise a promoter sequence positioned 5' to the nucleic acid encoding the light chain CDRs, such as one active in eukaryotic cells or prokaryotic cells. The nucleic acid may be located in a replicable vector, such as a non-viral vector or a viral vector. The nucleic acid further may comprise linker-encoding segments, wherein said linker-encoding segments located between said CDR-encoding segments, such as one that encodes a helix-turn-helix motif.

In yet another embodiment, there is provided an artificial antibody comprising a heavy chain-encoding segment comprising CDRs comprising the sequences of SEQ ID NOS: 3, 60 and 5; and comprising a light chain-encoding segment comprising CDRs comprising the sequences of SEQ ID NOS: 8, 9 and 10. The CDRs may be joined by synthetic linkers. The heavy chain may be fused to a non-antibody peptide or polypeptide segment. The antibody may be linked to a diagnostic reagent, such as a fluorophore, a chromophore, a dye, a radioisotope, a chemiluminescent molecule, a paramagnetic ion, or a spin-trapping reagent. The antibody may be linked to a therapeutic reagent, such as a cytokine, a toxin, a chemotherapeutic, a radiotherapeutic, a hormone, an antibody Fc fragment, neutrophil elastase, proteinase 3, a TLR agonist, a CpG-containing molecule, or an immune co-stimulatory molecule. The light chain may comprise SEQ ID NO: 40 or SEQ ID NO: 42, and/or the heavy chain comprises SEQ ID NO: 38 or SEQ ID NO: 44.

In still yet another embodiment, there is provided a method of making an antibody comprising (a) introducing into a host cell (i) a nucleic acid sequence encoding a heavy chain comprising CDRs shown in SEQ ID NOS: 3, 60 and 5, and (ii) a nucleic acid sequence encoding a light chain comprising CDRs shown in SEQ ID NOS: 8, 9 and 10; and (b) culturing said host cell under conditions supporting expression of said light and heavy chains. The method may further comprise isolating said antibody. The method may further comprising the step of linking said antibody to a diagnostic or therapeutic agent.

In a further embodiment, there is provided a method of detecting abnormal cells in a sample suspected of containing abnormal cells comprising contacting said sample with an antibody or an artificial antibody as described above. The antibody or artificial antibody may be conjugated to a diagnostic agent (such as a fluorophore, a chromophore, a dye, a radioisotope, a chemiluminescent molecule, a paramagnetic ion, or a spin-trapping reagent). The antibody or artificial antibody may be detected using a secondary binding agent, such as an anti-Fc receptor antibody. The sample may be (a) a tumor tissue from head & neck, brain, esophagus, breast, lung, liver, spleen, stomach, small intestine, large intestine, rectum, ovary, uterus, cervix, prostate, testicle or skin tissue, or (b) a fluid such as blood, lymph, urine, bone marrow aspirate or nipple aspirate. The sample may be from a resected tumor bed. The method may further comprising making a treatment decision based on the presence, absence or degree of detection, such as a decision to treat said subject with a PR-1-based peptide vaccine. The method may detect primary cancer cells, metastatic cancer cells or myeloid dysplastic cells.

In yet a further embodiment, there is provided a method of treating a subject with cancer comprising administering to said subject an antibody or an artificial antibody as described above. The antibody or artificial antibody may be conjugated to a therapeutic agent. The cancer may be a solid tumor, such as a head & neck tumor, a brain tumor, an esophageal tumor, a breast tumor, a lung tumor, a liver tumor, a spleen tumor, and stomach tumor, a small intestinal tumor, a large intestinal tumor, a rectal tumor, an ovarian tumor, a uterine tumor, a cervical tumor, a prostate tumor, a testicular tumor or a skin tumor. The cancer may be a blood cancer, such as a leukemia or lymphoma. The therapeutic agent may be a cytokine, a toxin, a chemotherapeutic, a radiotherapeutic, a hormone, an antibody Fc fragment, a TLR agonist, a CpG-containing molecule, or an immune co-stimulatory molecule. The method may further comprising providing said subject with a second anti-cancer therapy, such as a gene therapy, a chemotherapy, a radiotherapy, a hormone therapy, a toxin therapy or surgery. The antibody or artificial antibody may be administered to said subject more than once. The cancer may be recurrent or metastatic cancer. The antibody may be administered to said subject more than once.

In still yet a further embodiment, there is provided a method of treating a subject with an autoimmune disease comprising administering to said subject an antibody or an artificial antibody as described above. The autoimmune disease may be Wegener's granulomatosis, Churg-Strauss Syndrome, or systemic small vessel vasculitis. The antibody or artificial antibody may be conjugated to a therapeutic agent, such as a toxin or apoptosis-inducing agent. The method may further comprise providing said subject with a second anti-autoimmune therapy. The second anti-autoimmune therapy may be an anti-inflammatory agent. The antibody may be administered to said subject more than once.

Also provided is a method of inducing complement-mediated cytotoxicity of an HLA-A2 cancer cell comprising contacting said cancer cell with an antibody or an artificial antibody as described above.

Another embodiment of the present invention provides a method of detecting abnormal cells in a sample suspected of containing abnormal cells comprising contacting said sample with an antibody or artificial antibody as described above. The antibody or artificial antibody may be conjugated to a diagnostic agent, such as a fluorophore, a chromophore, a dye, a radioisotope, a chemiluminescent molecule, a paramagnetic ion, or a spin-trapping reagent. The antibody or artificial antibody may be detected using a secondary binding agent, such as an anti-Fc receptor antibody. The sample may be (a) a tumor tissue from head & neck, brain, esophagus, breast, lung, liver, spleen, stomach, small intestine, large intestine, rectum, ovary, uterus, cervix, prostate, testicle or skin tissue, or (b) a fluid such as blood, lymph, urine, bone marrow aspirate or nipple aspirate. The sample may be from a resected tumor bed. The method may further comprise making a treatment decision based on the presence, absence or degree of detection, such as deciding to treat said subject with a PR-1-based peptide vaccine. The method may detect primary cancer cells, metastatic cancer cells or myeloid dysplastic cells are detected.

In still another embodiment, there is provided a method of treating a subject with cancer comprising administering to said subject an antibody or artificial antibody as described above. The antibody or artificial antibody may be conjugated to a therapeutic agent, such a cytokine, a toxin, a chemotherapeutic, a radiotherapeutic, a hormone, an antibody Fc fragment, a TLR agonist, a CpG-containing molecule, or an immune co-stimulatory molecule. The cancer may be a solid tumor, such as a head & neck tumor, a brain tumor, an esophageal tumor, a breast tumor, a lung tumor, a liver tumor, a spleen tumor, and stomach tumor, a small intestinal tumor, a large intestinal tumor, a rectal tumor, an ovarian tumor, a uterine tumor, a cervical tumor, a prostate tumor, a testicular tumor or a skin tumor. Alternatively, the cancer may be a blood cancer, such as a leukemia or lymphoma. The cancer may be recurrent or metastatic cancer. The method may further comprise providing said subject with a second anti-cancer therapy, such as a gene therapy, a chemotherapy, a radiotherapy, a hormone therapy, a toxin therapy or surgery. The antibody or artificial antibody may be administered to said subject more than once.

In yet a further embodiment, there is provided a method of treating a subject with an autoimmune disease comprising administering to said subject an antibody or artificial antibody as described above. The autoimmune disease may be Wegener's granulomatosis, Churg-Strauss Syndrome, or systemic small vessel vasculitis. The antibody or artificial antibody may be conjugated to a therapeutic agent, such as a toxin or apoptosis-inducing agent. The method may further comprise providing said subject with a second anti-autoimmune therapy, such as an anti-inflammatory agent. The antibody may be administered to said subject more than once.

Additional methods include (i) treating a subject with a myeloid dysplastic disease comprising administering to said subject the antibody or artificial antibody described above; and (ii) inducing complement-mediated cytotoxicity of an HLA-A2 cancer cell comprising contacting said cancer cell with the antibody or artificial antibody described above.

Hu1-8F4 and Hu2-8F4 refer to Hu8F4-1 and Hu8F4-2, respectively. In addition, the term "Hu8F4" in this document refers generally to both humanized forms of 8F4 (Hu8F4-1 and Hu8F4-2).

As used herein the specification, "a" or "an" may mean one or more. As used herein in the claim(s), when used in conjunction with the word "comprising," the words "a" or "an" may mean one or more than one. As used herein "another" may mean at least a second or more.

Other objects and features of the present invention will become apparent from the following detailed description. It should be understood, however, that the description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Specificity of 8F4 for PR1/HLA-A2. ELISA with recombinant peptide/HLA-A2 monomers, loaded with PR1 or single amino acid-modified PR1 analogs. To determine the amino acid positions within the PR1 sequence (SEQ ID NO: 45) that are essential for optimal 8F4 binding, HLA-A2 monomers loaded with peptides containing alanine substitutions in PR1 (ALA1-ALA9) coated onto microtiter wells at increasing concentrations. Wells were then incubated with a fixed concentration of 8F4 or the control antibody bb7.2 (an HLA-A*0201 allele-specific mouse IgG2a monoclonal antibody). Binding was measured by ELISA using peroxidase-conjugated goat anti-mouse antibody. 8F4 bound to HLA-A2 loaded with PR1 and to most of PR1 analogs, with significantly less binding to the ALA1 analogue (alanine substituted for valine in position 1 of the peptide), and no binding to control peptide pp65/HLA-A2. Control antibody bb7.2 bound equally well to PR1- and pp65-loaded HLA-A2.

FIGS. 4A-B—8F4 Antibody induces complement-dependent cytotoxicity (CDC) of AML. Target cells were washed and resuspended in 10-RPMI/HEPES at a concentration $5 \times 10^5$ cells/ml. Twenty microliter (µl) of antibody and 100 µl of cells were mixed and warmed to 37° C. in 96-well plates, then 20 µl of ice cold standard rabbit complement (Cedarlane, Ontario, Canada) was added and incubated at 37° C. for 90 min. The cytotoxicity was determined using the Cyto-Tox Glo Cytotoxicity Assay (Promega). The antibody-specific CDC (AB-CDC) was calculated as: AB-CDC=$((L_{C+AB}-L_{C-AB})/(L_{max}-L_S)) \times 100\%$, where $L_{C+AB}$ is target cell lysis in the presence of complement plus antibody; $L_{T+C}$ is lysis in the presence of complement alone; $L_{spont}$ and $L_{max}$ were measured before and after adding the cytotoxic agent digitonin to the cells, per the manufacturers instructions. (FIG. 4A) Incubation with 20 µg 8F4 induced complement-dependent cytotoxicity of PBMC and leukopheresis (LP) cells taken from HLA-A2+ AML patients, but did not lyse control samples of PBMC from HLA-A2-negative AML or PBMC from HLA-A2+ normal donor. (FIG. 4B) 8F4-mediated lysis of HLA-A2+ AML was antibody dose-dependent, whereas isotype control antibody (IgG2a mouse anti-KLH) and human intravenous immunoglobulin (commercial IVIG) showed no lysis of AML.

FIG. 6—8F4 antibody prevents engraftment of AML in in vivo model. Primary HLA-A2+ leukemia cells ($10^6$) were washed, resuspended in PBS (100 µl), mixed with 8F4 or isotype control antibody (20 µg) and intravenously injected into 200 cGy-irradiated HLA-A2+ transgenic NOD/SCID mice. After two weeks mice were sacrificed, dissected, and the tissues were homogenized and analyzed for the presence of leukemia cells by flow cytometry with human and mouse cell surface markers. Flow cytometry results of cells isolated from mouse bone marrow (BM) are shown. Control (PBS-treated) and experimental animals that received AML cells plus 8F4 (AML+8F4 antibody) showed no human leukemia cell in BM. In contrast, animals that received AML cells plus control antibody (AML+isotype control) showed human CD33+CD45+ cells in bone marrow, with the same phenotype as the infused AML.

FIGS. 8A-B—8F4 Antibody Prevents Engraftment of Human AML in HLA-A2 Tg Xenograft Model. Primary HLA-A2+ AML cells ($10^6$) were washed, resuspended in PBS (250 µl), mixed with 2 0 µg 8F4 or isotype control antibody and intravenously injected into sub-lethally irradiated (200 cGy) HLA-A2 Tg NOD/SCID mice. At the indicated times, peripheral blood, bone marrow and tissues were analyzed for presence of leukemia by histochemistry (FIG. 8A) and flow cytometry (FIG. 8B). Irradiated mice without AML transfer and pre-transfer AML cells were used as negative and positive controls, respectively. (FIG. 8A) AML infiltration in tissues of experimental mice following injection with AML cells plus 8F4 (left panels), injection with AML cells plus isotype control antibody (iso, central panels), and no AML transfer control mice (right panels). (FIG. 8B) AML cells (shown pre-transfer, left panels) were not detected in the bone marrow (top two panels) and peripheral blood (bottom two panels) of no transfer control and experimental 8F4-treated mice. Mice that received AML cells mixed with isotype matched control antibody (iso) showed engraftment of AML1 and AML5 two or four weeks after AML transfer. An extended panel, including a mouse cell specific marker (mCD45), 3-6 human markers (CD45, CD13, CD33, CD34, CD38, HLA-DR), and Live/Dead Fixable Aqua (Invitrogen) was used for flow cytometric analysis of AML engraftment. All plots show viable mCD45-cells.

FIGS. 9A-C—8F4 Induces Transient (21-day) Neutropenia in HLA-A2 Transgenic NOD/SCID due to the Expression of Conserved PR1 Sequence on HLA-A2-Expressing Murine Hematopoietic Cells. HLA-A2 Tg NOD/SCID mice were injected with 200 µg (10 mg/kg) 8F4 or isotype control Ab. These animals have been shown to present endogenous PR1. Nine days later, bone marrow cells were harvested and stained with mAb directed to mouse antigens (B220-PE, Gr-1-PB, CD11b-APC, F4/80-PE-Cy7, CD3-FITC and LIVE/DEAD Fixable Aqua) and examined by flow cytometry. (FIG. 9A) Reduced granulocytes were evident in scatter profiles of bone marrow (left panels). Gr-1lo immature neutrophils were present, but Gr-1hi mature neutrophils were less numerous in the bone marrow of 8F4-treated mice (center panels). Additionally, monocytes (SSClo CD11b+; lower right gate of right panels) were reduced in 8F4-treated animals. (FIG. 9B) Intravenous injection of 8F4 (5 mg/kg) induced transient reduction in absolute numbers of circulating mature granulocytes, macrophages and monocytes in HLA-A2 Tg NOD/SCID mice. Three weeks after treatment all populations remain. Gates shown in FIG. 9A were used to determine the frequency of each cell type as a percentage of live cells. Error bars are standard deviations of n=2 animals per group. One representative experiment out of three is shown. (FIG. 9C) No significant pathological changes were evident in liver, lung, spleen, kidney, heart or brains of HLA-A2 Tg NOD/SCID mice 7 days after injection of 200 µg (10 mg/kg) 8F4. H&E sections of representative tissues from 2 mice are shown.

FIGS. 10A-B—8F4 Induces Transient Leukopenia of Established Human Hematopoietic Cells after Transfer of Human CD34+ Cell Enriched Cord Blood into NOD/SCID Mice. Fresh HLA-A2+ cord blood (CB) units (50-150 ml) were ficolled by using Histopaque1077, washed with PBS, then with CliniMACS buffer (0.5% HSA in PBS pH 7.2/1 mM EDTA, Miltenyi). $10^8$ cells were resuspended in 300 ml MACS buffer, mixed with 100 ml CD34 Microbeads (Miltenyi) and incubated at 4° C. for 30 minutes and washed. CD34⁻ cells, labeled with magnetic beads, were purified by using 2 LS columns (Miltenyi). CD34⁺ cells were eluted from the column, counted and iv injected into the irradiated (400 rad) NOD/SCID mouse ($1-2.5\times10^6$ cells per mouse). Control mouse CB1-5 did not received CB cells. (FIG. 10A) Beginning 4 weeks after transplant, peripheral blood from mice was taken weekly or every other week to monitor cord blood engraftment by using FACS with mouse CD45, human CD45, and HLA markers. 9-12 weeks after transfer mice were i.v. injected with 20 µg (1 mg/kg) 8F4 twice with one week interval between injection (dotted arrows). (FIG. 10B) Four weeks after $2^{nd}$ 8F4 injection mice were sacrificed. Blood, spleen and bone arrow were analyzed for engraftment of human cells as above.

FIG. 12. Alignment of the amino acid sequences of 8F4 VH (SEQ ID NO: 15), humanized 8F4 (Hu8F4) VH (SEQ ID NO: 16) and human acceptor U96282 VH (SEQ ID NO: 17). Amino acid residues are shown in single letter code. Numbers above the sequences indicate the positions according to Kabat et al. (1991). CDR sequences defined by Kabat et al. (1991) are underlined. CDR residues in U96282 VH are omitted in the figure.

FIG. 13. Alignment of the amino acid sequences of 8F4 VL (SEQ ID NO: 18), two versions of humanized 8F4 VL (Hu8F4 VL1 and VL2) (SEQ ID NOS: 19-20) and human acceptor AY043146 VL (SEQ ID NO: 21). Amino acid residues are shown in single letter code. Numbers above the sequences indicate the positions according to Kabat et al. (1991). CDR sequences defined by Kabat et al. (1991) are underlined. An underlined residue in Hu8F4 VL1 was predicted to contact with the CDRs and the corresponding mouse residue was retained at this location in Hu8F4 VL1. CDR residues in AY043146 VL are omitted in the figure.

(FIG. 16A) Specificity assay. (FIG. 16B) Affinity assay. (FIG. 16C) CDC assay.

(FIG. 20A) Tumor-associated neutrophils in 231 BrCA xenograft tumors. (FIG. 20B) Primary tumor model. (FIG. 20C) Metastatic tumor model.

FIGS. 21A-B. Solid tumor cell lines take up NE and P3. Cell lines representing solid tumors were incubated with (FIG. 21A) NE (10 mg/ml) or (FIG. 21B) P3 (10 mg/ml), and then permeabilized and stained with anti-NE or anti-P3 Abs. Data represent mean 6 SEM fold increase in NE or P3 uptake versus unpulsed cells from triplicate wells from two independent experiments. MDA-MB-231, Breast carcinoma; MIA PaCa-2, pancreatic carcinoma; Mel 624 and Mel 526, melanoma; OVCAR3, ovarian adenocarcinoma; SW-620, colon adenocarcinoma.

FIGS. 22A-D. Breast cancer does not endogenously express P3. mRNA was extracted from (FIG. 22A) breast cancer cell lines and (FIG. 22B) primary breast cancer tissue. RT-PCR was performed using P3 primers, which shows lack of P3 mRNA expression in breast cancer cell lines and primary breast cancer. Jurkat and HL-60 leukemia cell lines were used as negative and positive controls, respectively. Primary breast cancer cells from patient tissues, sample breasts 1-3, were obtained by LCM performed on tumor obtained from patients at the time of surgical resection. Mammaglobin-1 (MGB-1) was used to confirm analysis of breast cancer cells. β-actin and GAPDH were used as loading controls. (FIG. 22C) Immunoblots demonstrate lack of P3 protein in WCL from five different breast cancer cell lines. Gels were loaded with 20 mg protein. Purified P3 (5 mg) was used as positive control, and GAPDH was used as a loading control. (FIG. 22D) Immunohistochemistry showing absence of P3 in patient breast cancer tissue (breast 3). Left panel, H&E section (original magnification 3200) showing poorly differentiated carcinoma with admixed neutrophils. Right panel, Immunohistochemical staining for P3 shows positive staining of P3 (brown) in the admixed neutrophils, but not in the breast cancer cells. The inset (original magnification 3400) shows a rare tumor cell engulfing a neutrophil. Both images are taken from the same patient and are representative of five tissues. Arrowheads indicate neutrophils.

FIGS. 23A-C. P3 is taken up by breast cancer cell lines and localizes to lysosomal compartments. (FIG. 23A) MDA-MB-231, MCF-7, and MCF-7-HER18 cell lines were incubated with soluble P3 (10 mg/ml) for 1, 4, and 24 h and then intracellularly stained with anti-P3 Ab. MFI was measured for triplicate experimental groups and was normalized to the MFI of unpulsed cells. Fold increase in MFI versus unpulsed cells is plotted on the y-axis. Data are means 6 SEM and represent two independent experiments. (FIG. 23B) MDA-MB-231 cells were incubated with increasing doses of soluble P3 or OVA (ova) and analyzed by flow cytometry for intracellular uptake of P3 or OVA using anti-P3 or anti-OVA Abs, respectively. Data are means 6 SEM from duplicate experiments. (FIG. 23C) MDA-MB-231 cells were cultured with soluble P3 (10 mg/ml) and then stained intracellularly for P3 (red) and LAMP-2 (green). Confocal microscopy images demonstrate localization of P3 in lysosomal compartments 4 h following uptake, as shown by overlay images (yellow). Nuclei appear blue using DAPI. Scale bars, 5 mm.

FIGS. 24A-F. Uptake of P3 and cross-presentation of P3 and NE increases breast cancer susceptibility to killing by PR1-CTLs and anti-PR1/HLA-A2. (FIG. 24A) MDA-MB-231 breast cancer cells were incubated with soluble P3, irradiated PMNs, or PBMC for 4 h. Cells were permeabilized, stained with anti-P3 Ab, and analyzed by flow cytometry. For cell-associated uptake, light scatter seen on flow cytometry provided a clear distinction between PBMC, PMNs, and MDA-MB-231 cells. PBMC and PMNs alone were used as negative and positive controls, respectively. ANOVA followed by Tukey test was performed using Prism 5.0 software (*p, 0.05). Data are means 6 SEM from duplicate experiments. (FIG. 24B) MDA-MB-231 breast cancer cells were cultured with soluble P3 or NE (10 mg/ml) at increasing time points and then analyzed for expression of PR1/HLA-A2. Mean 6 SEM fold increase of the MFI of PR1/HLA-A2 versus unpulsed cells is shown from duplicate experiments. ANOVA followed by Tukey test was performed using Prism 5.0 software (*p=0.01, **p, 0.0001). (FIGS. 24C-D) MDA-MB-231 cells were cultured for 24 h in media containing NE or P3 (10 mg/ml) and the Ag presentation inhibitors brefeldin A or lactacystin. Cells were then analyzed for expression of PR1/HLA-A2. Mean 6 SEM of the MFI of PR1/HLA-A2 is shown from duplicate wells of a representative experiment. ANOVA followed by Tukey test were performed using Prism 5.0 software (*p, 0.01, **p, 0.0001). (FIG. 24E) MDA-MB-231 cells were cultured overnight in media containing P3 or NE (10 mg/ml), loaded with calcein-AM, and then cocultured with PR1-CTLs for 4 h. Cytotoxicity was determined by measuring released calcein-AM. NE- or P3-pulsed cells show higher killing versus unpulsed MDA-MB-231 cells. PR1-pulsed and unpulsed T2 cells were used as positive and negative controls, respectively. Data are means 6 SEM from duplicate wells from a representative experiment. (FIG. 24F) MDAMB-231 cells were cultured with NE (10 mg/ml) or P3 (10 mg/ml) for 24 h. Cells were then incubated with anti-PR1/HLA-A2 (8F4) Ab for 60 min, and then complement was added. Complement-dependent cytotoxicity was measured using calcein-AM release and shows specific killing of NE- or P3-pulsed MDA-MB-231 cells by 8F4 Ab. Cytotoxicity data are means 6 SEM from duplicate wells from a representative experiment. Unpaired t test was performed using Prism 5.0 software (*p, 0.05).

FIGS. 25A-D. PR1/HLA-A2 and PR1-CTL are detected in breast cancer and melanoma patients. (FIG. 25A) Resected HLA-A2+ patient breast cancer tissues (breasts 1 and 4) were stained with anti-PR1/HLA-A2 (8F4)-647 (red) and anti-CK7)-FITC (green), and then imaged using confocal laser microscopy. PR1/HLA-A2 appears to be expressed by breast cancer cells, as shown by the costaining of 8F4 with CK7. DAPI-blue was used to stain cell nuclei. (FIG. 25B) Consecutive sections from resected HLA-A2+ breast cancer tissue were stained with anti-CD45-647 (red) (left panel) or anti-CK7-FITC (green) and 8F4-647 (red) (right panel), and then imaged using confocal laser microscopy. PR1/HLA-A2 is expressed by breast cancer cells (8F4+/CK7+) in areas that have minimal leukocytes (CD452), thereby confirming PR1/HLA-A2 expression by breast cancer cells. DAPI-blue was used to stain cell nuclei. (FIG. 25C) Box and whisker plot shows PR1-CTLs in peripheral blood from HLA-A2+ patients with breast cancer (n=11), melanoma (n=7), and healthy (n=9) HLA-A2+ donors. Mann-Whitney U test was performed using Prism 5.0 software (*p, 0.05). (FIG. 25D) Resected HLA-A2+ (Melanoma 1) and HLA-A22 (Melanoma 2) patient tissues were stained with 8F4-647 (red) and anti-MITF-FITC (green), and then imaged using confocal laser microscopy. PR1/HLA-A2 appears to be expressed in the HLA-A2+ melanoma sample (Melanoma 1), as shown by the costaining of 8F4 with MITF. DAPI-blue was used to stain for cell nuclei. Scale bars, 20 mm.

FIGS. 26A-F. Cross-presentation of P3 and NE by melanoma cells increases susceptibility to PR1-CTL. (FIG. 26A) Double staining of NE (brown) and MITF (pink), or (FIG. 26B) P3 (brown) and MITF (pink) in primary melanoma patient samples shows lack of NE and P3 in melanoma. The images were taken at original magnification 3100. Inset, Original magnification 3400, shows scattered NE- or P3-positive cells, which are most likely inflammatory cells. (FIG. 26C) Western blot showing absence of NE and P3 in melanoma cell lines. U-937 leukemia cell line was used as a positive control for NE and P3. Tubulin was used as loading control. M=m.w. marker. (FIGS. 26D-E) The 526 HLA-A2+ melanoma cell line was cultured with soluble NE (10 mg/ml) or P3 (10 mg/ml) at increasing time points and then analyzed for (FIG. 26D) uptake of NE and P3 and (FIG. 26E) cross-presentation (i.e., PR1/HLA-A2 expression). -Fold increase of the MFI of NE or P3 (FIG. 26D) or PR1/HLA-A2 (FIG. 26E) versus unpulsed cells is shown on the y-axis. ANOVA followed by Tukey test was performed using Prism 5.0 software (**p=0.0001, *p, 0.05). Data represent mean 6 SEM from duplicate experiments. (F) Calcein-AM cytotoxicity assay shows killing of NE (10 mg/ml) and P3 (10 mg/ml) 24-h pulsed 526 HLA-A2+ melanoma cell line by PR1-CTLs versus unpulsed (Unp) Mel 526. Unpulsed (T2 Unp) and PR1-pulsed (T2 PR1) T2 cells were used as negative and positive controls, respectively. Data are means 6 SEM from duplicate wells from a representative experiment. Unpaired t-test was performed using Prism 5.0 software (*p, 0.05).

DESCRIPTION OF ILLUSTRATIVE EMBODIMENTS

Figure 2:
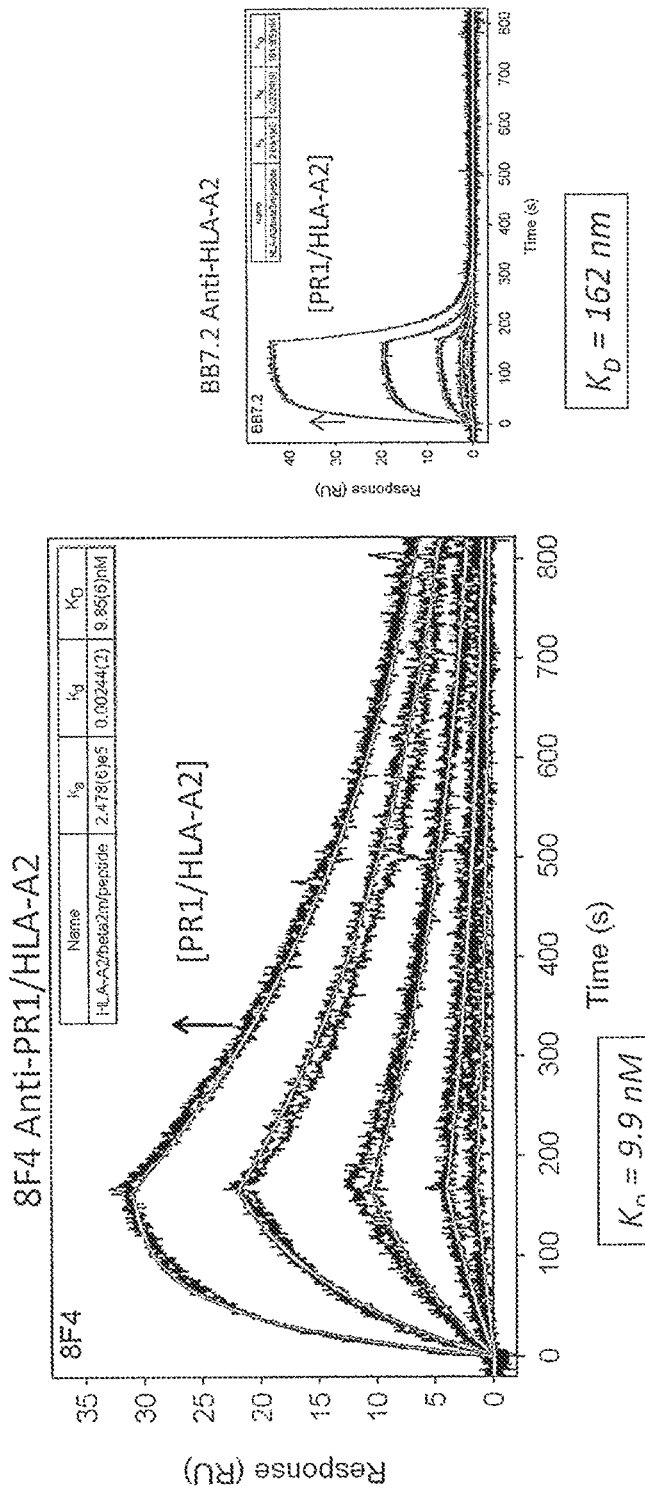
FIG. 2—Affinity of 8F4 monoclonal antibody to PR1/HLA-A2. Affinity measurements of peptide/HLA-A2 binding to 8F4 and bb7.2 antibodies was determined by surface plasmon resonance using the BIAcore 3000. The test antibodies were captured onto anti-mouse antibody-coated surfaces. The analyte, peptide/HLA-A2, was diluted to 100 nM and tested in duplicate for binding to the antibody-coated surfaces. The analysis was performed at 25 C using PBS, 0.005% Tween-20, 0.1 mg/ml BSA, pH 7.4 as the running buffer. To obtain the binding affinity the experimental data were fit to a first-order kinetic model (shown as orange lines in the figures) and $K_D$ for 8F4 and bb7.2 was subsequently determined.

The PR-1 self-peptide (VLQELNVTV; SEQ ID NO:45) has been shown to be recognized on leukemia cell membrane-expressed HLA-A*0201 by CD8+ cytotoxic T lymphocytes (CTL), and PR1-specific CTL specifically lyse myeloid leukemia but not normal bone marrow cells. Vaccination of HLA-A2+ patients with AML, CML, and MDS with PR1 peptide induced PR-1-CTL immunity in 58% of patients and objective clinical responses in 13 of 66 (20%) patients. While these results are encouraging, high tumor burden remains a barrier to successful vaccination.

Because PR1 peptide is expressed in sufficient quantity only on the surface of myeloid leukemia cells and not on normal bone marrow cells, the inventors sought to develop an antibody targeted to PR1/HLA-A*0201 that might be used therapeutically to treat patients with myeloid leukemia or that could be used to identify which patients might be susceptible to PR1-based immunotherapy, such as vaccines or adoptive T-cell transfer. Since HLA-A2+ is the most commonly expressed HLA allele (40% of the general Caucasian population), antibody-based therapy for a T-cell epitope therefore would be novel and it might be widely applied. By immunizing immune competent BALB/c mice with recombinant PR1/HLA-A*0201 monomers, they obtained an IgG2a-kappa monoclonal antibody (8F4) with specificity for the combined PR1/HLA-A*0201 epitope. The 8F4 antibody was shown to have high affinity for PR1/HLA-A*0201 ($K_D$=9.9 nanomolar) and it was shown to only recognize PR1-pulsed T2 target cells but not control peptide-pulsed cells. 8F4 binds to HLA-A2+ AML using both FACS and confocal microscopy to label the cells, but not to normal HLA-A2+ peripheral blood cells.

In addition, 8F4 induced dose-dependent complement-mediated cytotoxicity (CDC) of HLA-A2+ primary human leukemia but not normal bone marrow cells. Significantly, 8F4 antibody specifically prevented engraftment of human AML in an HLA-A2 transgenic NOD/SCID animal model with only a single exposure to antibody at the time of adoptive transfer into the animal. In addition, 8F4 delayed breast cancer tumor growth and prolonged survival despite the fact that P3 and NE are not expressed in breast cancer cells. Taken together, these results show that the creation of an antibody with specificity for the cell membrane-bound PR1/HLA-A*0201 epitope, an important T-cell target antigen, that specifically targets and eliminates human leukemias and solid tumors.

I. Definitions

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment.

"Major histocompatibility complex" or "MHC" is a cluster of genes that plays a role in control of the cellular interactions responsible for physiologic immune responses. In humans, the MHC complex is also known as the HLA complex. For a detailed description of the MHC and HLA complexes, see Paul (1993).

"Human leukocyte antigen" or "HLA" is a human class I or class II major histocompatibility complex (MHC) protein (see, e.g., Stites, 1994).

An "HLA supertype or family," as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like supertype molecules (where xx denotes a particular HLA type), are synonyms.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

"Abnormal cell" is any cell that is considered to have a characteristic a typical for that cell type, including atypical growth, typical growth in an atypical location or typical action against an atypical target. Such cells include cancer cells, benign hyperplastic or dysplastic cells, inflammatory cells or autoimmune cells.

II. PR-1 and HLA Restriction

A. PR-1

The PR-1 self-peptide (VLQELNVTV; SEQ ID NO:45) is derived from proteinase 3 (P3) and neutrophil elastase (NE), both aberrantly expressed in leukemia. It has been shown to be recognized on leukemia cell membrane-expressed HLA-A*0201 by CD8+ cytotoxic T lymphocytes (CTL). PR-1-specific CTL specifically lyse myeloid leukemia, including acute myelogenous leukemia (AML), chronic myelogenous leukemia (CML), and myelodysplastic syndrome (MDS) but not normal bone marrow cells. Previously, the inventors have shown that PR-1 vaccination of HLA-A2+ patients with AML, CML, and MDS with PR1 peptide in Montanide ISA-51 and GM-CSF induced PR-1-CTL immunity in 58% of patients and objective clinical responses in 13 of 66 (20%) patients.

B. HLA-A2

The human leukocyte antigen system (HLA) is the name of the major histocompatibility complex (MHC) in humans. The super locus contains a large number of genes related to immune system function in humans. This group of genes resides on chromosome 6, and encode cell-surface antigen-presenting proteins and many other genes. The proteins encoded by certain genes are also known as antigens, as a result of their historic discovery as factors in organ transplantations. The major HLA antigens are essential elements in immune function. Different classes have different functions.

HLA class I antigens (A, B & C) present peptides from inside the cell (including viral peptides if present). These peptides are produced from digested proteins that are broken down in the lysosomes. The peptides are generally small polymers, about 9 amino acids in length. Foreign antigens attract killer T-cells (also called CD8$^+$ cells) that destroy cells. HLA class II antigens (DR, DP & DQ) present antigens from outside of the cell to T-lymphocytes. These particular antigens stimulate T-helper cells to reproduce and these T-helper cells then stimulate antibody producing B-cells, self-antigens are suppressed by suppressor T-cells.

HLA-A2 (A2) is a human leukocyte antigen serotype within the HLA-A "A" serotype group. The serotype identifies the gene products of many HLA-A*02 alleles, including HLA-A*0201, *0202, *0203, *0206, and *0207 gene products. A*02 is globally common, but A*0201 is at high frequencies in Northern Asia and North America. A2 is the most diverse serotype, showing diversity in Eastern Africa and Southwest Asia. While the frequency of A*0201 in Northern Asia is high, its diversity is limited to A*0201 the less common Asian variants A*0203, A*0206.

The serotype is determined by the antibody recognition of $\alpha^2$ subset of HLA-A α-chains. For A2, the α "A" chain are encoded by the HLA-A*02 allele group and the β-chain are encoded by B2M locus. A2 and A*02 are almost synonymous in meaning. A2 is more common in Northern Asia and North America than elsewhere, and it is part of a several long haplotypes.

III. Antibodies

The present invention concerns the production and use of antibodies that bind to PR1 in the context of HLA-A2 presentation. Antibodies are capable of "specific binding" to a particular target or series of antigenically related targets. As used herein, an antibody is said to be capable of "specific binding" to a antigen if it discriminates from antigenically distinct molecules based on binding to the variable region of the antibody. Such interactions are in contrast to non-specific binding that involve classes of compounds, irrespective of their chemical structure (such as the binding of proteins to nitrocellulose, etc.). In particular, an antibody of the present invention can exhibit "highly specific binding" such that they will be incapable or substantially incapable of binding to even closely related molecules Monoclonal antibodies can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Successful fusions are then screened for production of appropriate antibodies.

In one embodiment, antibody molecules will comprise fragments (such as (F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule, or they may be capable of binding to an activated protein C epitope and a "non-activated protein C" epitope.

Where the antibodies or their fragments are intended for therapeutic purposes, it may desirable to "humanize" them in order to attenuate any immune reaction. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985; also incorporated herein by reference. "Humanized" antibodies can alternatively be produced by CDR or CEA substitution. Jones et al. (1986); Verhoeyan et al. (1988); Beidler et al. (1988); all of which references are incorporated herein by reference.

A. Variants

The following is a discussion based upon changing the amino acids of a protein to create a modified protein. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (–0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (–0.4); sulfur containing amino acids: cysteine (–1.0) and methionine (–1.3); hydrophobic, nonaromatic amino acids: valine (–1.5), leucine (–1.8), isoleucine (–1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present invention may also employ the use of peptide mimetics for the preparation of polypeptides (see e.g., Johnson, 1993) having many of the natural properties of an antibody, but with altered and/or improved characteristics. The underlying rationale behind the use of mimetics is that the peptide backbone of proteins exists chiefly to orient amino acid side chains in such a way as to facilitate molecular interactions, such as those of antibody and antigen. These principles may be used, in conjunction with the principles outline above, to engineer second generation molecules having many of the natural properties of an antibody but with altered and even improved characteristics.

It is contemplated that the present invention may further employ sequence variants such as insertional or deletion variants. Deletion variants lack one or more residues of the native protein. Insertional mutants typically involve the addition of material at a non-terminal point in the polypeptide. It also will be understood that insertional sequence variants may include N- or C-terminal amino acids, and yet still be essentially as set forth in one of the sequences disclosed herein, so long as the sequence meets the criteria set forth above, including the maintenance of biological activity.

The present invention also contemplates isotype modification. As discussed below, antibody 8F4 was determined to be an IgG2a-κ. By modifying the Fc region to have a different isotype, different functionalities can be achieved. For example, changing to IgG1 can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

B. Single Chain Antibody

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. The image to the right shows how this modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation. Table 3 illustrates several cross-linkers.

TABLE 3

HETERO-BIFUNCTIONAL CROSS-LINKERS

| linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |

TABLE 3-continued

HETERO-BIFUNCTIONAL CROSS-LINKERS

| linker | Reactive Toward | Advantages and Applications | Spacer Arm Length\after cross-linking |
|---|---|---|---|
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

C. Purification

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

D. Conjugation of Antibodies to Therapeutic or Diagnostic Agents

In one embodiment, the antibodies of the present invention may be linked to various reagents for use in diagnosis and therapy of disease. Linking may be performed using a variety of well known chemical reactions and agents, some of which are described elsewhere in this document.

1. Diagnostic Reagents

Many diagnostic/imaging agents are known in the art, as are methods for their attachment to proteins, including antibodies (see, e.g., U.S. Pat. Nos. 5,021,236; 4,938,948; and 4,472,509, each incorporated herein by reference). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$, $^{125}$I is often being preferred for use in certain embodiments, and technicium$^{99m}$ and/or indium$^{111}$ are also often preferred due to their low energy and suitability for long range detection. Radioactively labeled receptors of the present invention may be produced according to well-known methods in the art. For instance, receptors can be iodinated by contact with sodium and/or potassium iodide and a chemical oxidizing agent such as sodium hypochlorite, or an enzymatic oxidizing agent, such as lactoperoxidase. TcRs according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes, which exist as metallic ions to antibody are diethylenetriaminepentaacetic acid (DTPA) or ethylene diaminetetraacetic acid (EDTA).

Among the fluorescent labels contemplated for use as conjugates are Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

2. Therapeutic Reagents

A wide variety of therapeutic agents made linked to antibodies of the present invention. For example, the radioisotopes discussed above, though useful in diagnostic contexts, may be also be used as therapeutic agents. Chemotherapeutics may also be conjugated to antibodies, and include cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicamycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristine, vinblastine and methotrexate.

Another class of therapeutic agent is the toxins. Cholera toxin, botulism toxin, pertussis toxin, ricin A and B chains, as well as other natural or synthetic toxins are contemplated.

Cytokines and lymphokines are yet another class of therapeutic agents than can be coupled to the TcR of the present invention, and include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, TNFα, GM-CSF, INFα, IFNβ, and IFNγ.

In other embodiments, anti-inflammatory agents are contemplated as therapeutic agents that may be conjugated to antibodies. Anti-inflammatories include NSAIDs, steroids, rapamycin, infliximab, and ontak. Immunosuppressive agents include FK-506 and cyclosporine A.

TLR agonist may be linked to the antibody, e.g., through the Fc portion of the molecule. Agonists of TLRs are compounds that stimulate, or "turn on," the immune system. Natural agonists for TLR9 are components of DNA that are common to bacteria and viruses. Natural agonists for TLRs 7 and 8 are patterns of RNA found in viruses. Following recognition of their natural DNA and RNA agonists, TLRs 7, 8, and 9 each initiate a different cascade of protective immune responses. TLR agonists include oligodeoxynucleotides, hyaluronic acid fragments, imiquimod, lavendustin C, lipid A, loroxibine, LPS, monophosphoryl lipda A, myristicin, resiquimod, *S. typhimurium* flagellin, HKLM, PAM3CSK4, and polyI:C.

IV. Nucleic Acids and Expression

A. Antibody Encoding Nucleic Acids

One aspect of the invention, nucleic acid are provided that encode various portions of antibody heavy and light chain, variable and constant domains. A nucleic acid segment may be derived from genomic DNA, complementary DNA (cDNA) or synthetic DNA. Where incorporation into an expression vector is desired, the nucleic acid may also comprise a natural intron or an intron derived from another gene, as well as other non-coding (e.g., regulatory) and coding regions (e.g., linkers). As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein.

The term "recombinant" may be used in conjunction with a polypeptide or the name of a specific polypeptide, and generally refers to a polypeptide produced from a nucleic acid molecule that has been manipulated in vitro or that is the replicated product of such a molecule. Recombinant vectors and isolated nucleic acid segments may variously include the antibody-coding regions themselves, coding regions bearing selected alterations or modifications in the basic coding region, or they may encode larger polypeptides that include non-antibody regions.

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1,000, about 1100, about 1200, about 1300, about 1400, about 1500, about 1750, about 2000, about 2250, about 2500 or greater nucleotide residues in length.

It is contemplated that antibody may be encoded by any nucleic acid sequence that encodes the appropriate amino acid sequence, such as those in SEQ ID NOS: 3, 60, 5, 8, 9, 10 (heavy CDRs 1, 2 and 3; light CDRs 1 and 2, 3), and SEQ ID NO: 16, which includes the heavy CDRs and framework regions 1, 2 and 3, which flank upstream of heavy CDRs 1, 2 and 3, respectively, and SEQ ID NOS: 19 or 20, which includes the light CDRs and framework regions 1, 2 and 3, which flank upstream of light CDRs 1, 2 and 3, respectively. The design and production of nucleic acids encoding a desired amino acid sequence is well known to those of skill in the art, using standardized codon tables (Table 4). In particular embodiments, the codons selected for encoding each amino acid may be modified to optimize expression of the nucleic acid in the host cell of interest. The term "functionally equivalent codon" is used herein to refer to codons that encode the same amino acid, such as the six codons for arginine or serine, and also refers to codons that encode biologically equivalent amino acids. Codon preferences for various species of host cell are well known in the art. Codons preferred for use in humans, are well known to those of skill in the art (Wada et al., 1990). Codon preferences for other organisms also are well known to those of skill in the art (Wada et al., 1990, included herein in its entirety by reference).

TABLE 4

Codon Table

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

B. Nucleic Acid Expression

Prokaryote- and/or eukaryote-based systems can be used to produce nucleic acid sequences, or their cognate polypeptides, proteins and peptides. The present invention contemplates the use of such an expression system to produce the antibodies that bind PR-1/HLA-A2. One powerful expression technology employs the insect-cell/baculovirus system. The insect-cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC ® 2.0 from INVITROGEN® and BACPACK™ BACULOVIRUS EXPRESSION SYSTEM FROM CLONTECH®.

In addition, numerous other expression systems exists which are commercially and widely available. One example of such a system is the STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

1. Viral Vectors and Delivery

There are a number of ways in which expression vectors may be introduced into cells. Viruses provide powerful tools for expression of protein products encoded by nucleic acids. Thus, in certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986).

Adenoviral Vectors. A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

AAV Vectors. The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in the vaccines of the present invention (Muzyczka, 1992). AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors. Retroviruses have promise as gene delivery vectors in vaccines due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid (e.g., one encoding an antigen of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors. Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990). Lentiviruses also have been explored as vaccine vectors (VandenDriessche et al., 2002).

Delivery Using Modified Viruses. A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via asialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Non-Viral Nucleic Acid Delivery

Suitable non-viral methods for nucleic acid delivery to effect expression of compositions of the present invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538, 877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

V. Antibodies for Diagnosis of Cancer or Hyperplastic or Dysplastic Disorders

In an embodiment of the present invention, there are provided methods of diagnosing cancers such as leukemia (e.g., AML, CML, MDS), as well as myelodysplastic disorders. Myelodysplasias (MDS) refer to a group of disorders in which the bone marrow does not function normally and produces insufficient number of normal blood cells. MDS affects the production of any, and occasionally all, types of blood cells including red blood cells, platelets, and white blood cells (cytopenias). About 50% of pediatric myelodysplasia can be classified in five types of MDS: refractory anemia, refractory anemia with ring sideroblasts, refractory anemia with excess blasts, refractory anemia with excess blasts in transformation, and chronic myelomonocytic leukemia. The remaining 50% typically present with isolated or combined cytopenias such as anemia, leucopenia and/or thrombocytopenia (low platelet count). Although chronic, MDS progresses to become acute myeloid leukemia (AML) in about 30 percent of patients.

Also contemplated for diagnosis according to the present invention are solid tumor cancers. Such cancer lung cancer, head and neck cancer, breast cancer, pancreatic cancer, prostate cancer, renal cancer, bone cancer, testicular cancer, cervical cancer, gastrointestinal cancer, lymphomas, preneoplastic lesions in the lung, colon cancer, melanoma, and bladder cancer. Other hyperplastic, neoplastic and dysplastic diseases, including benign hyperproliferative diseases are also with the scope of the diagnostic procedures described herein.

A. Administration of Diagnostic Reagents

Administration of diagnostic reagents is well known in the art and will vary depending on diagnosis to be achieved. For example, where a discrete tumor mass or masses is/are to be imagined, local or regional administration (e.g., in the tumor vasculature, local lymph system or local arteries or veins) my be utilized. Alternatively, one may provide diagnostic reagents regionally or systemically. This may be the route of choice where imaging of an entire limb or organism is desired, where know specific tumor mass has been identified, or when metastasis is suspected.

B. Injectable Compositions and Formulations

One method for the delivery of a pharmaceutical according to the present invention is systemically. However, the pharmaceutical compositions disclosed herein may alternatively be administered parenterally, intravenously, intradermally, intramuscularly, transdermally or even intraperitoneally as described in U.S. Pat. Nos. 5,543,158; 5,641,515 and 5,399,363 (each specifically incorporated herein by reference in its entirety).

Injection of pharmaceuticals may be by syringe or any other method used for injection of a solution, as long as the agent can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1,000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

VI. Therapeutic Methods

A. Cancer and Hyperplastic/Dysplastic/Neoplastic Disease

The antibodies of the present invention may be used in the methods of treating hyperplastic/dysplastic/neoplastic diseases/conditions including cancer. Types of diseases/conditions contemplated to be treated with the peptides of the present invention include, but are not limited to leukemias such as, AML, MDS and CIVIL, as well as myelodysplasias. Other types of cancers may include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, bladder cancer and any other neoplastic diseases.

To kill cells, inhibit-cell growth, inhibit metastasis, decrease tumor/tissue size, tumor cell burden or otherwise reverse or reduce the malignant phenotype of tumor cells, using the methods and compositions of the present invention, one would generally contact a hyperplastic/neoplastic/cancer cell with the therapeutic compound such as a polypeptide or an expression construct encoding an antibody of the present invention, normally dispersed in a pharmaceutically acceptable buffer or carrier (see above in the discussion of diagnostic agents). The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation. Any of the formulations and routes of administration discussed with respect to the treatment or diagnosis of cancer may also be employed with respect to neoplastic diseases and conditions. Ex vivo embodiments, where tumor cells are treated/transduced outside a patient's body (either specifically or as part of a larger cell population) are contemplated.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml), while for tumors of <4 cm, a volume of about 1-3 ml will be used. Multiple injections delivered as single dose comprise about 0.1 to about 0.5 ml volumes. The viral particles may advantageously be contacted by administering multiple injections to the tumor, spaced at approximately 1 cm intervals.

In the case of surgical intervention, the present invention may be used may be used at the time of surgery, and/or thereafter, to treat residual or metastatic disease. For example, a resected tumor bed may be injected or perfused with a formulation comprising antibodies. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hr, to about 2-6 hr, to about 6-12 hr, to about 12-24 hr, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6-dose application over a two-week period. The two-week regimen may be repeated one, two, three, four, five, six or more times. During a course of treatment, the need to complete the planned dosings may be re-evaluated.

B. Combination Therapies

It also may prove advantageous to use combination therapies, where a second anti-cancer agent is included. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided with a therapy according to the present invention in a combined amount effective to kill or inhibit proliferation of the cell. This process may involve contacting the cells with the both agent(s) at the same time. This may be achieved by contacting the cell with a single composition or pharmacological formulation that includes both agents, or by contacting the cell with two distinct compositions or formulations at the same time.

Alternatively, the antibody therapy may precede or follow the other agent treatment by intervals ranging from minutes to weeks. In embodiments where the other agent and antibodies are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed; for example, the antibody therapy (with or without a conjugated therapeutic agent) is "A" and the secondary anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the therapeutic agents of the present invention to a patient will follow general protocols for the administration of that particular secondary therapy, taking into account the toxicity, if any, of the antibody treatment. It is expected that the treatment cycles would be repeated as necessary. It also is contemplated that various standard therapies, as well as surgical intervention, may be applied in combination with the described cancer therapies.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicamycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristine, vinblastine and methotrexate, Temozolomide (an aqueous form of DTIC), or any analog or derivative variant of the foregoing. The combination of chemotherapy with biological therapy is known as biochemotherapy. The present invention contemplates any chemotherapeutic agent that may be employed or known in the art for treating or preventing cancers.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T-cells and NK cells. The combination of therapeutic modalities, i.e., direct cytotoxic activity and inhibition or reduction of Fortalin would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. Nos. 5,801,005; 5,739,169; Hui and Hashimoto, 1998; Christodoulides et al., 1998), cytokine therapy (e.g., interferons, and; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the tumor-associated HLA-restricted peptide therapies described herein.

Adoptive Immunotherapy. In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders was few compared to those who did not respond.

Passive Immunotherapy. A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989). Possible therapeutic antibodies include anti-TNF, anti-CD25, anti-CD3, anti-CD20, CTLA-4-IG, and anti-CD28.

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

4. Gene Therapy

In yet another embodiment, the secondary treatment is a gene therapy in which a therapeutic polynucleotide is administered before, after, or at the same time as the tumor-associated HLA-restricted peptide is administered. Delivery of a vector encoding a the tumor-associated HLA-restricted peptide in conjunction with a second vector encoding one of the following gene products will have a combined anti-hyperproliferative effect on target tissues. Alternatively, a single vector encoding both genes may be used. A variety of proteins are encompassed within the invention, some of which are described below. Various genes that may be targeted for gene therapy of some form in combination with the present invention are will known to one of ordinary skill in the art and may comprise any gene involved in cancers.

Inducers of Cellular Proliferation. The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that antisense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity. The proteins Jun, Fos and Myc are proteins that directly exert their effects on nuclear functions as transcription factors.

Inhibitors of Cellular Proliferation. The tumor suppressor oncogenes function to inhibit excessive cellular proliferation. The inactivation of these genes destroys their inhibitory activity, resulting in unregulated proliferation. The most common tumor suppressors are Rb, p53, p21 and p16. Other genes that may be employed according to the present invention include APC, DCC, NF-1, NF-2, WT-1, MEN-I, MEN-II, zacl, p73, VHL, C-CAM, MMAC1/PTEN, DBCCR-1, FCC, rsk-3, p27, p27/p16 fusions, and p21/p27 fusions.

Regulators of Programmed Cell Death. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, Bcls, Mcl-1, A1, Bfl-1) or counteract Bcl-2 function and promote cell death (e.g., Bax, Bak, Bik, Bim, Bid, Bad, Harakiri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

C. Autoimmune Diseases

The present invention also contemplates the treatment of autoimmune disease using the antibodies of the present invention. PR1 is derived from myeloid self-proteins. Proteinase 3 (Pr3), which contains PR1, is the target of autoimmune attack in Wegener's granulomatosis. Myeloperoxidase (MPO) is the target antigen in small vessel vasculitis (Franssen et al., 1996; Brouwer et al., 1994; Molldrem et al., 1996), with evidence for both T-cell and antibody immunity in patients with these diseases. Wegener's granulomatosis is associated with production of cytoplasmic anti-neutrophil cytoplasmic antibodies (cANCA) with specificity for Pr3 (Molldrem et al., 1997), while microscopic polyangiitis and Churg-Strauss syndrome are associated with perinuclear ANCA (pANCA) with specificity for MPO (Molldrem et al., 1999; Savage et al., 1999). As such, inhibiting immune cell recognition of PR1 may be therapeutic for autoimmune disease.

Thus, antibodies of the present invention will be administered to subjects suffering from autoimmune disease to neutralize effects of other autoantibodies (e.g., pANCA against proteinase 3). Alternatively, an antibody will be engineered to be "bi-specific," i.e., to have immunologic specificity for two antigen, where one is PR1/HLA-A2, and the other is a dendritic cell surface antigens like DEC-205, LOX-1, RAGE, thereby blocking dendritic cell function in antigen presentation.

1. Vasculitis

Vasculitis is a process caused by inflammation of blood vessel walls and results in a variety of disorders. An accepted classification system for vasculitis has not emerged, although it may be categorized by the size or type of the involved blood vessel as large-, medium-, or small-vessel vasculitis. Small-vessel vasculitis is defined as vasculitis that affects vessels smaller than arteries (i.e., arterioles, venules, and capillaries); however, small-vessel vasculitis can also involve medium-sized arteries. Anti-neutrophil cytoplasmic antibodies (ANCA)-associated vasculitis is the most common cause of small-vessel vasculitis and includes microscopic polyangiitis, Wegener's granulomatosis, Churg-Strauss syndrome, and certain types of drug-induced vasculitis.

Wegener's Granulomatosis. Wegener's Granulomatosis is a rare disorder which causes inflammation of blood vessels in the upper respiratory tract (nose, sinuses, ears), lungs, and kidneys. Many other areas of the body may also be affected, with arthritis (joint inflammation) occurring in almost half of all cases. The eyes and skin may also be affected. The cause is unknown, but Wegener's Granulomatosis is thought to be an autoimmune disorder and is often classified as one of the rheumatic diseases. Destructive lesions develop in the upper and lower respiratory tract and the kidney. In the kidney, these lesions cause glomerulonephritis that may result in hematuria (blood in the urine) and kidney failure. It occurs most often between the ages of 30 and 50, and men are affected twice as often as women. It is rare in children, but has been seen in infants as young as 3 months old. The kidney disease can progress rapidly, with kidney failure occurring within months of the initial diagnosis. If untreated, kidney failure and death occur in more than 90% of all patients with Wegener's granulomatosis.

Early symptoms may include fatigue, malaise, fever, and a sense of discomfort around the nose and sinuses. Upper respiratory infections such as sinusitis or ear infections frequently precede the diagnosis of Wegener's Granulomatosis. Other upper respiratory symptoms include nose bleeds, pain, and sores around the opening of the nose. Persistent fever without an obvious cause (fever of undetermined origin—FUO) may be an initial symptom. Night sweats may accompany the fever. Loss of appetite and weight loss are common. Skin lesions are common, but there is no one characteristic lesion associated with the disease. Kidney disease is necessary to make the definitive diagnosis of Wegener's Granulomatosis. The urine may be bloody, which often first appears as red or smoky urine. There may be no symptoms, but is easily diagnosed with laboratory studies. Eye problems develop in a significant number of patients and may range from a mild conjunctivitis to severe inflammation of the eyeball and the tissues around the eyeball. Additional symptoms include weakness, loss of appetite, weight loss, bloody discharge from the nose, pain over the sinuses, sinusitis, lesions in and around the opening of the nose, cough, coughing up blood, bloody sputum, shortness of breath, wheezing, chest pain, blood in the urine, rashes, and joint pain.

Diagnosis as made by take a biopsy of abnormal tissue, which may include open lung biopsy, upper airway biopsy, nasal mucosal biopsy, bronchoscopy with transtracheal biopsy, kidney biopsy, urinalysis, chest x-ray, bone marrow aspiration, blood test (for autoantibodies). Treatment includes corticosteroids, cyclophosphamide, methotrexate, or azathioprine, which can produce long-term remission in over 90% of affected people.

Churg-Strauss Syndrome. Churg-Strauss Syndrome (CSS), also known as allergic granulomatosis, is a form of systemic vasculitis. CSS is similar to polyarteritis nodosa, but the abundance of eosinophils distinguished this disease. Most CSS patients are middle-aged, with a history of new or increased severity asthma—asthma being one of the cardinal features of CSS. The symptoms of asthma may begin long before the onset of vasculitis. Other early symptoms include nasal polyps and allergic rhinitis. The disease often transitions into eosinophilia, with counts reaching as high as 60%. The next phase of disease is overt vasculitis, which can involve the skin, lungs, nerves, kidneys, and other organs. Peripheral nerve involvement can be particularly debilitating and includes pain, numbness, or tingling in extremities (neuropathy/mononeuritis multiplex). Prior to the advent of therapies, CSS was often a fatal disease. The majority of patients died from rampant, uncontrolled disease.

The cause of CSS is not known, but it is like multifactorial. Though a genetic factor may exist, CSS is only rarely seen in two members of the same family. Thus, environmental factors and infections are more likely to be the cause, but there is no definitive evidence of this. Diagnosis is performed by a specific combination of symptoms and signs, the pattern of organ involvement, and the presence of certain abnormal blood tests (eosinophilia, in particular). In addition to a detailed patient history and physical examination, blood tests, chest X-rays and other types of imaging studies, nerve conduction tests, and tissue biopsies (lung, skin, or nerve) may be performed to aid in the diagnosis. In order to be classified as a CSS patient, a patient should have at least 4 of the following 6 criteria: 1) asthma; 2) eosinophilia [>10% on differential WBC count]; 3) mononeuropathy; 4) transient pulmonary infiltrates on chest X-rays; 5) paranasal sinus abnormalities; and 6) biopsy containing a blood vessel with extravascular eosinophils.

CSS usually responds to prednisone. Initially, high doses of oral prednisone are used, but after the first month or so, this high dose of prednisone is gradually tapered down over the ensuing months. Other immunosuppressive drugs, such as azathioprine, cellcept, methotrexate, or cyclophosphamide may be used in addition to prednisone. High doses of intravenous steroids may be useful for those patients with severe disease, or for those who are unresponsive to other treatments. With proper therapy, symptoms begin to resolve quickly, with gradual improvement in cardiac and renal function, as well as improvement in the pain that results from peripheral nerve involvement. Therapy may last for 1 to 2 years, depending on patient response and continuation of disease.

2. Crohn's Disease

Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective (reviewed in V. A. Botoman et al., 1998). Immunosuppression with cyclosporine is sometimes beneficial for patients resistant to or intolerant of corticosteroids (Brynskov et al., 1989).

Nevertheless, surgical correction is eventually required in 90% of patients; 50% undergo colonic resection (Leiper et al., 1998; Makowiec et al., 1998). The recurrence rate after surgery is high, with 50% requiring further surgery within 5 years (Leiper et al., 1998; Besnard et al., 1998).

One hypothesis for the etiology of Crohn's disease is that a failure of the intestinal mucosal barrier, possibly resulting from genetic susceptibilities and environmental factors (e.g., smoking), exposes the immune system to antigens from the intestinal lumen including bacterial and food antigens (e.g., Soderholm et al., 1999; Hollander et al., 1986; Hollander, 1992). Another hypothesis is that persistent intestinal infection by pathogens such as *Mycobacterium paratuberculosis*, *Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce (Sartor, 1997). The presence of IgA and IgG anti-*Sacccharomyces cerevisiae* antibodies (ASCA) in the serum was found to be highly diagnostic of pediatric Crohn's disease (Ruemmele et al., 1998; Hoffenberg et al., 1999).

In Crohn's disease, a dysregulated immune response is skewed toward cell-mediated immunopathology (Murch, 1998). But immunosuppressive drugs, such as cyclosporine, tacrolimus, and mesalamine have been used to treat corticosteroid-resistant cases of Crohn's disease with mixed success (Brynskov et al., 1989; Fellerman et al., 1998).

Recent efforts to develop diagnostic and treatment tools against Crohn's disease have focused on the central role of cytokines (Schreiber, 1998; van Hogezand & Verspaget, 1998). Cytokines are small, secreted proteins or factors (5 to 20 kD) that have specific effects on cell-to-cell interactions, intercellular communication, or the behavior of other cells. Cytokines are produced by lymphocytes, especially $T_H1$ and $T_H2$ lymphocytes, monocytes, intestinal macrophages, granulocytes, epithelial cells, and fibroblasts (reviewed in Rogler & Andus, 1998; Galley & Webster, 1996). Some cytokines are pro-inflammatory (e.g., TNF-α, IL-1(α and β), IL-6, IL-8, IL-12, or leukemia inhibitory factor (LIF)); others are anti-inflammatory (e.g., IL-1 receptor antagonist, IL-4, IL-10, IL-11, and TGF-β). However, there may be overlap and functional redundancy in their effects under certain inflammatory conditions.

In active cases of Crohn's disease, elevated concentrations of TNF-α and IL-6 are secreted into the blood circulation, and TNF-α, IL-1, IL-6, and IL-8 are produced in excess locally by mucosal cells (Funakoshi et al., 1998). These cytokines can have far-ranging effects on physiological systems including bone development, hematopoiesis, and liver, thyroid, and neuropsychiatric function. Also, an imbalance of the IL-1β/IL-1ra ratio, in favor of pro-inflammatory IL-1β, has been observed in patients with Crohn's disease (Rogler & Andus, 1998; Saiki et al., 1998; Dionne et al., 1998; but see S. Kuboyama, 1998). One study suggested that cytokine profiles in stool samples could be a useful diagnostic tool for Crohn's disease (Saiki et al., 1998).

Treatments that have been proposed for Crohn's disease include the use of various cytokine antagonists (e.g., IL-1ra), inhibitors (e.g., of IL-1β converting enzyme and antioxidants) and anti-cytokine antibodies (Rogler and Andus, 1998; van Hogezand & Verspaget, 1998; Reimund et al., 1998; N. Lugering et al., 1998; McAlindon et al., 1998). In particular, monoclonal antibodies against TNF-α have been tried with some success in the treatment of Crohn's disease (Targan et al., 1997; Stack et al., 1997; van Dullemen et al., 1995). These compounds can be used in combination therapy with compounds of the present invention.

Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species (U.S. Pat. No. 5,443,826). However, there has been no known cause of Crohn's disease to which diagnosis and/or treatment could be directed.

3. Rheumatoid Arthritis

The exact etiology of RA remains unknown, but it is clear that it has autoimmune aspects. The first signs of joint disease appear in the synovial lining layer, with proliferation of synovial fibroblasts and their attachment to the articular surface at the joint margin (Lipsky, 1998). Subsequently, macrophages, T-cells and other inflammatory cells are recruited into the joint, where they produce a number of mediators, including the cytokines interleukin-1 (IL-1), which contributes to the chronic sequelae leading to bone and cartilage destruction, and tumour necrosis factor (TNF-α), which plays a role in inflammation (Dinarello, 1998; Burger & Dayer, 1995; van den Berg, 2001). The concentration of IL-1 in plasma is significantly higher in patients with RA than in healthy individuals and, notably, plasma IL-1 levels correlate with RA disease activity (Eastgate et al., 1988). Moreover, synovial fluid levels of IL-1 are correlated with various radiographic and histologic features of RA (Kahle et al., 1992; Rooney et al., 1990).

In normal joints, the effects of these and other proinflammatory cytokines are balanced by a variety of anti-inflammatory cytokines and regulatory factors (Burger & Dayer, 1995). The significance of this cytokine balance is illustrated in juvenile RA patients, who have cyclical increases in fever throughout the day (Prieur et al., 1987). After each peak in fever, a factor that blocks the effects of IL-1 is found in serum and urine. This factor has been isolated, cloned and identified as IL-1 receptor antagonist (IL-1ra), a member of the IL-1 gene family (Hannum et al., 1990). IL-1ra, as its name indicates, is a natural receptor antagonist that competes with IL-1 for binding to type I IL-1 receptors and, as a result, blocks the effects of IL-1 (Arend et al., 1998). A 10- to 100-fold excess of IL-1ra may be needed to block IL-1 effectively; however, synovial cells isolated from patients with RA do not appear to produce enough IL-1ra to counteract the effects of IL-1 (Firestein et al., 1994; Fujikawa et al., 1995).

4. Systemic Lupus Erythematosus

Systemic lupus erythematosus (SLE) is an autoimmune rheumatic disease characterized by deposition in tissues of autoantibodies and immune complexes leading to tissue injury (Kotzin, 1996). In contrast to autoimmune diseases such as MS and type 1 diabetes mellitus, SLE potentially involves multiple organ systems directly, and its clinical manifestations are diverse and variable (reviewed by Kotzin & O'Dell, 1995). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (G N) (Hahn & Tsao, 1993; Ohnishi et al., 1994). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

The mechanisms by which autoantibodies are induced in these autoimmune diseases remain unclear. As there has been no known cause of SLE, to which diagnosis and/or treatment could be directed, treatment has been directed to suppressing immune responses, for example with macrolide antibiotics, rather than to an underlying cause. (e.g., U.S. Pat. No. 4,843,092).

5. Juvenile Rheumatoid Arthritis

Juvenile rheumatoid arthritis (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe.

Jarvis (1998) and others (Arend, 2001) have proposed that the pathogenesis of rheumatoid disease in adults and children involves complex interactions between innate and adaptive immunity. This complexity lies at the core of the difficulty of unraveling disease pathogenesis.

Both innate and adaptive immune systems use multiple cell types, a vast array of cell surface and secreted proteins, and interconnected networks of positive and negative feedback (Lo et al., 1999). Furthermore, while separable in thought, the innate and adaptive wings of the immune system are functionally intersected (Fearon & Locksley, 1996), and pathologic events occurring at these intersecting points are likely to be highly relevant to the inventors' understanding of pathogenesis of adult and childhood forms of chronic arthritis (Warrington, et al., 2001).

Polyarticular JRA is a distinct clinical subtype characterized by inflammation and synovial proliferation in multiple joints (four or more), including the small joints of the hands (Jarvis, 2002). This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease (Jarvis, 1998).

6. Sjögren's Syndrome

Primary Sjögren's syndrome (SS) is a chronic, slowly progressive, systemic autoimmune disease, which affects predominantly middle-aged women (female-to-male ratio 9:1), although it can be seen in all ages including childhood (Jonsson et al., 2002). It is characterized by lymphocytic infiltration and destruction of the exocrine glands, which are infiltrated by mononuclear cells including CD4+, CD8+ lymphocytes and B-cells (Jonsson et al., 2002). In addition, extraglandular (systemic) manifestations are seen in one-third of patients (Jonsson et al., 2001).

The glandular lymphocytic infiltration is a progressive feature (Jonsson et al., 1993), which, when extensive, may replace large portions of the organs. Interestingly, the glandular infiltrates in some patients closely resemble ectopic lymphoid microstructures in the salivary glands (denoted as ectopic germinal centers) (Salomonsson et al., 2002; Xanthou & Polihronis, 2001). In SS, ectopic GCs are defined as T and B cell aggregates of proliferating cells with a network of follicular dendritic cells and activated endothelial cells. These GC-like structures formed within the target tissue also portray functional properties with production of autoantibodies (anti-Ro/SSA and anti-La/SSB) (Salomonsson &, Jonsson, 2003).

In other systemic autoimmune diseases, such as RA, factors critical for ectopic GCs have been identified. Rheumatoid synovial tissues with GCs were shown to produce chemokines CXCL13, CCL21 and lymphotoxin (LT)-β (detected on follicular center and mantle zone B cells). Multivariate regression analysis of these analytes identified CXCL13 and LT-β as the solitary cytokines predicting GCs in rheumatoid synovitis (Weyand & Goronzy, 2003). Recently CXCL13 and CXCR5 in salivary glands has been shown to play an essential role in the inflammatory process by recruiting B and T-cells, therefore contributing to lymphoid neogenesis and ectopic GC formation in SS (Salomonsson & Larsson, 2002).

7. Psoriasis

Psoriasis is a chronic skin disease of scaling and inflammation that affects 2 to 2.6 percent of the United States population, or between 5.8 and 7.5 million people. Although the disease occurs in all age groups, it primarily affects adults. It appears about equally in males and females. Psoriasis occurs when skin cells quickly rise from their origin below the surface of the skin and pile up on the surface before they have a chance to mature. Usually this movement (also called turnover) takes about a month, but in psoriasis it may occur in only a few days. In its typical form, psoriasis results in patches of thick, red (inflamed) skin covered with silvery scales. These patches, which are sometimes referred to as plaques, usually itch or feel sore. They most often occur on the elbows, knees, other parts of the legs, scalp, lower back, face, palms, and soles of the feet, but they can occur on skin anywhere on the body. The disease may also affect the fingernails, the toenails, and the soft tissues of the genitals and inside the mouth. While it is not unusual for the skin around affected joints to crack, approximately 1 million people with psoriasis experience joint inflammation that produces symptoms of arthritis. This condition is called psoriatic arthritis.

Psoriasis is a skin disorder driven by the immune system, especially involving T-cells. In psoriasis, T-cells are put into action by mistake and become so active that they trigger other immune responses, which lead to inflammation and to rapid turnover of skin cells. In about one-third of the cases, there is a family history of psoriasis. Researchers have studied a large number of families affected by psoriasis and identified genes linked to the disease. People with psoriasis may notice that there are times when their skin worsens, then improves. Conditions that may cause flare-ups include infections, stress, and changes in climate that dry the skin. Also, certain medicines, including lithium and beta blockers, which are prescribed for high blood pressure, may trigger an outbreak or worsen the disease.

8. Multiple Sclerosis

Multiple sclerosis (MS) continues to be a serious health problem that afflicts hundreds of thousands each year in the US alone, and millions worldwide. It is one of the most common diseases of the central nervous system (brain and spinal cord). MS is an inflammatory condition associated with demyelination, or loss of the myelin sheath. Myelin, a fatty material that insulates nerves, acts as insulator in allowing nerves to transmit impulses from one point to another. In MS, the loss of myelin is accompanied by a disruption in the ability of the nerves to conduct electrical impulses to and from the brain and this produces the various symptoms of MS, such as impairments in vision, muscle coordination, strength, sensation, speech and swallowing, bladder control, sexuality and cognitive function. The plaques or lesions where myelin is lost appear as hardened, scar-like areas. These scars appear at different times and in different areas of the brain and spinal cord, hence the term "multiple" sclerosis, literally meaning many scars.

Currently, there is no single laboratory test, symptom, or physical finding that provides a conclusive diagnosis of MS. To complicate matters, symptoms of MS can easily be confused with a wide variety of other diseases such as acute disseminated encephalomyelitis, Lyme disease, HIV-associated myelopathy, HTLV-I-associated myelopathy, neurosyphilis, progressive multifocal leukoencephalopathy, systemic lupus erythematosus, polyarteritis nodosa, Sjögren's syndrome, Behçet's disease, sarcoidosis, paraneoplastic syndromes, subacute combined degeneration of cord, subacute myelo-optic neuropathy, adrenomyeloneuropathy, spinocerebellar syndromes, hereditary spastic paraparesis/primary lateral sclerosis, strokes, tumors, arteriovenous malformations, arachnoid cysts, Arnold-Chiari malformations, and cervical spondylosis. Consequently, the diagnosis of MS must be made by a process that demonstrates findings consistent with MS, and also rules out other causes.

Generally, the diagnosis of MS relies on two criteria. First, there must have been two attacks at least one month apart. An attack, also known as an exacerbation, flare, or relapse, is a sudden appearance of or worsening of an MS symptom or symptoms which lasts at least 24 hours. Second, there must be more than one area of damage to central nervous system myelin sheath. Damage to sheath must have occurred at more than one point in time and not have been caused by any other disease that can cause demyelination or similar neurologic symptoms. MM (magnetic resonance imaging) currently is the preferred method of imaging the brain to detect the presence of plaques or scarring caused by MS.

The diagnosis of MS cannot be made, however, solely on the basis of MM. Other diseases can cause comparable lesions in the brain that resemble those caused by MS. Furthermore, the appearance of brain lesions by MM can be quite heterogeneous in different patients, even resembling brain or spinal cord tumors in some. In addition, a normal MM scan does not rule out a diagnosis of MS, as a small number of patients with confirmed MS do not show any lesions in the brain on MM. These individuals often have spinal cord lesions or lesions which cannot be detected by MRI. As a result, it is critical that a thorough clinical exam also include a patient history and functional testing. This should cover mental, emotional, and language functions, movement and coordination, vision, balance, and the functions of the five senses. Sex, birthplace, family history, and age of the person when symptoms first began are also important considerations. Other tests, including evoked potentials (electrical diagnostic studies that may reveal delays in central nervous system conduction times), cerebrospinal fluid (seeking the presence of clonally-expanded immunoglobulin genes, referred to as oligoclonal bands), and blood (to rule out other causes), may be required in certain cases.

D. Combination Therapy

Combination therapies for the immune disorders listed above is also contemplated. Such therapies would include standard therapies such as anti-inflammatories and immunosuppressive agents, used in conjunction with the therapeutic methods of the present invention. Such standard therapies would be capable of negatively affecting an immune cell causing disease in a subject or to alleviate the symptoms of such disease. This process may involve contacting the cells or subject with the both agent(s) at the same time. This may be achieved with a single composition or pharmacological formulation that includes both agents, or with two distinct compositions or formulations at the same time. Alternatively, the antibody therapy may precede or follow the other agent treatment by intervals ranging from minutes to weeks.

Various combinations may be employed; for example, the antibody therapy (with or without a conjugated therapeutic agent) is "A" and the secondary immune disease therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the therapeutic agents of the present invention to a patient will follow general protocols for the administration of that particular secondary therapy, taking into account the toxicity, if any, of the antibody therapy. It is expected that the treatment cycles would be repeated as necessary. It also is contemplated that various standard therapies, as well as surgical intervention, may be applied in combination with the described therapies.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Antibody production. To obtain an antibody against the combined PR1/HLA-A*0201 epitope, the inventors immunized BALB/c mice with recombinant PR1/HLA-A*0201 monomers via subcutaneous (SQ) and intraperitoneal (IP) routes, three times spaced two weeks apart. Splenocytes were isolated from the immunized animal and B cells were fused with HGPRT negative, immortalized myeloma cells using polyethylene glycol (PEG). Hybridoma cells were then selected with pp65/HLA-A*0201 and PR1/HLA-A*0201 monomers and placed into 96-well plates for single cell cloning.

Antibody Screening and Characterization. Monoclonal cell lines (~20,000) were screened with PR1/HLA-A*0201 monomers by ELISA to identify a positive antibody-secreting hybridoma. The 8F4 hybridoma was identified by ELISA with specificity for PR1/HLA-A*0201 and was characterized using isotype-specific antibodies and immunoglobulin light chain antibodies.

Antibody Cloning, Sequence Analysis and Binding Studies. 8F4 heavy chain was cloned from hybridoma cDNA and primary sequence was obtained. Epitope mapping was performed by folding altered PR1 peptides, containing an Ala substitution at each P1 to P9 position, with the HLA-A*0201 heavy chain plus β-2 micro globulin. Binding affinity of 8F4 to PR1/HLA-A*0201 was determined by surface Plasmon resonance on a Biacore instrument with immobilized 8F4 and increasing concentration of soluble PR1/HLA-A*0201. FACS analysis and confocal imaging were utilized to study the binding of 8F4 to normal and abnormal cells.

Antibody Activity. To determine whether binding of 8F4 to AML triggers cell lysis, antibody-dependent cellular cytotoxicity (ADCC) and complement-dependent cytotoxicity (CDC) assays were performed. AML cells from patient material that was shown to be sensitive to 8F4 CDC-mediated lysis were incubated in the presence or absence of 8F4 or isotype control and then transferred into irradiated (200 cGy) immunodeficient HLA-A2 transgenic NOD/SCID mice. At two weeks the animals were sacrificed and splenocytes and bone marrow were analyzed by FACS.

Total RNA isolation. Qiagen RNEASY® kit with minelut columns were used. RNA loading buffer was made as follows: add 1 µl ethidium bromide (EtBr) (10 mg/ml) to 100 µl, 10× DNA loading dye, 1% agarose in 1× TAE, RNAse free $H_2O$ (in kit). Instructions are "Frozen vial of hybridoma cells or 1-5×10$^6$ live cells. If active cultures are available, pellet 1-5×10$^6$ live cells in 15 ml conical tube as in step 4 and proceed to step 5. If only frozen cells are available, thaw 1 vial hybridoma cells at 37° C., remove from water bath promptly after thaw, mix gently. Wipe vial with 70% Ethanol and unscrew cap taking care to avoid touching threads. Transfer content of vial to 15 ml conical tube containing 15 ml complete media. Centrifuge 100×g (~1,000 rpm for low speed Sorvall centrifuge) for 5 min. During spin, add β-mercaptoethanol to small aliquot of RLT buffer. Carefully remove all the media from cells with 10 ml pipette. Lyse cell pellet in buffer RLT using QIASHREDDER® and follow Qiagen protocol for RNA isolation. Elute RNA from minelut column with 2× of 15 µl RNAse free $dH_2O$ depending on starting cell amount (if from 6-well, elute with 1×13 µl). RNA should remain on ICE throughout following procedures. Pour 1% agarose minigel containing 1 µg/ml EtBr and during 15 min solidification time quantitate RNA. Quantitate 2 µl RNA using spectrophotometer, using same RNAse free $H_2O$ above as a blank. Calculate RNA concentration: $(A_{260})(40)$—µg/ml. A260/280 ratio should be >1.6. Check quality of RNA by running 1 µg on 1% agarose minigel in 10 µl total volume of 1× RNA loading buffer. Run ~1 inch into the gel. Analyze gel on photo documentation system. The banding pattern of high quality RNA is characterized by distinct 28s and 18s ribosomal RNA bands at an ideal ratio of 2:1 in intensity. A 1:1 ratio may be acceptable; however no bands or a smear at the bottom of the gel is indicative of RNA degradation and indicates that this RNA should not be used."

Isolation and sequence analysis of rearranged Ig variable region (V) genes from hybridoma. To obtain DNA sequences from V heavy chain (VH) and V light chain (VL) genes, the rapid amplification of cDNA ends (RACE) PCR in combination with human heavy chain constant region primers or light chain constant region primers was used. 5'RACE cDNA amplification was performed with the BD SMART™ RACE cDNA amplification kit (BD Bioscience) and followed the instructions provided therewith. PFU ULTRA® (Stratagene), Universal primer A mix (UPM) and gene specific primers (GSP) for human IgG H&L constant region were utilized.

Cloning and DNA sequencing of 5' RACE PCR products used the TOPO® cloning kit (Invitrogen) and gel extraction kit (Qiagen). For IgG L, 8 colonies were isolated for miniprep and screen by EcoRI digest. Six positive clones were sequenced with M13 rev and T7 primers. For IgG, 8 colonies were isolated for miniprep and screen by EcoRI digest. Six positive clones were sequenced with M13 rev and T7 primers.

Example 2

Results

Antibody production. To obtain an antibody against the combined PR1/HLA-A*0201 epitope, the inventors immunized BALB/c mice with recombinant PR1/HLA-A*0201 monomers via subcutaneous (SQ) and intraperitoneal (IP) routes, three times spaced two weeks apart. Splenocytes were isolated from the immunized animal and B cells were fused with HGPRT negative, immortalized myeloma cells using polyethylene glycol (PEG). Hybridoma cells were then selected with pp65/HLA-A*0201 and PR1/HLA-A*0201 monomers and placed into 96-well plates for single cell cloning.

Antibody Screening and Characterization. Monoclonal cell lines were screened with PR1/HLA-A*0201 monomers by ELISA to identify a positive antibody-secreting hybridoma. Nearly 2,000 hybridomas were screened and one, dubbed 8F4, was identified by ELISA with specificity for PR1/HLA-A*0201. The 8F4 hybridoma was characterized using isotype-specific antibodies and immunoglobulin light chain antibodies and shown to secrete a single IgG2a-κ PR1/HLA-A*0201-specific antibody.

Figure 3:
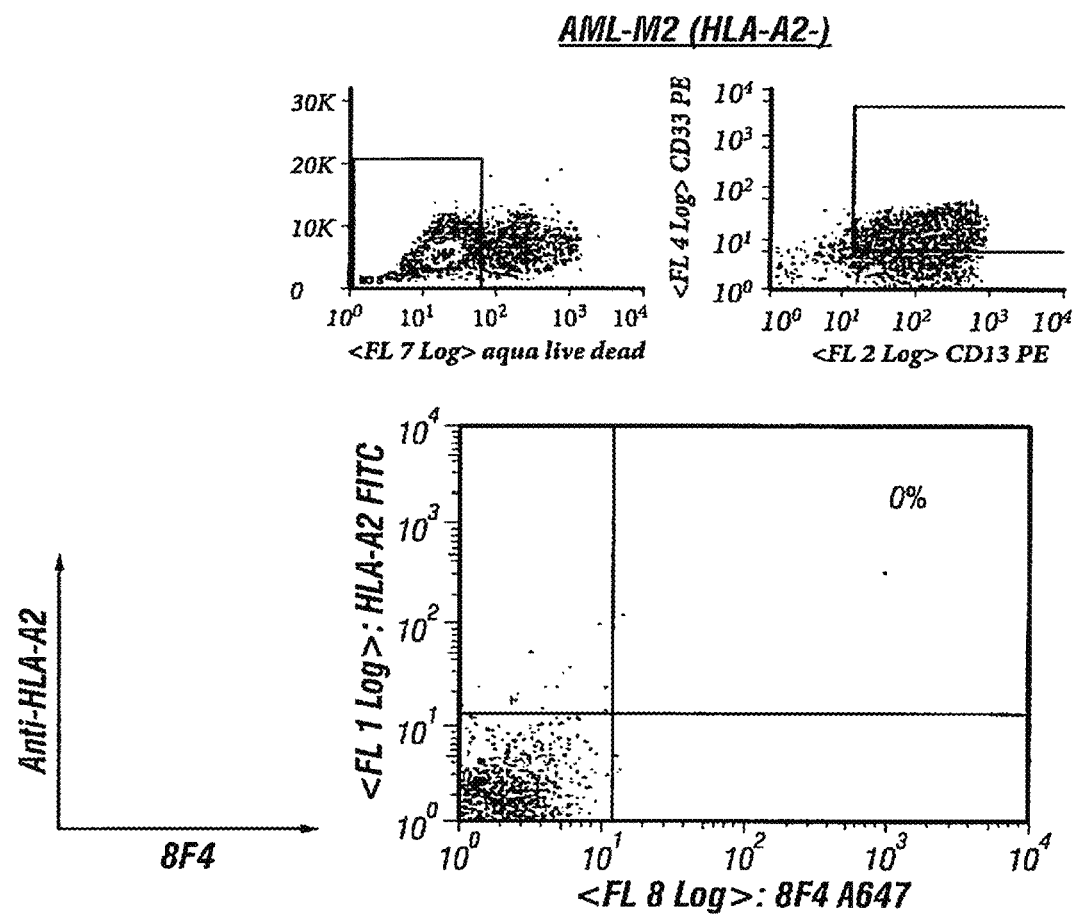
FIG. 3—Specificity of 8F4 for HLA-A2+ AML. Multiparameter flow cytometry of leukemia and normal PBMC with 8F4 and cell surface antibodies. PBMC from AML patients and normal donors were gated on live cells using aqua and then stained with 8F4 (conjugated with ALEXA Fluor 647), bb7.2 (conjugated with FITC), and surface phenotype antibodies for CD13 and CD33, and analyzed by flow cytometry. The following gating strategy was used: first, aqua-live cells were analyzed for CD13 and CD33 expression, and double positive cells were analyzed for expression of PR1/HLA-A2 (8F4) and total HLA-A2 expression (bb7.2). Negative quadrant gating was established using HLA-A2-negative AML control cells.
Figure 3:
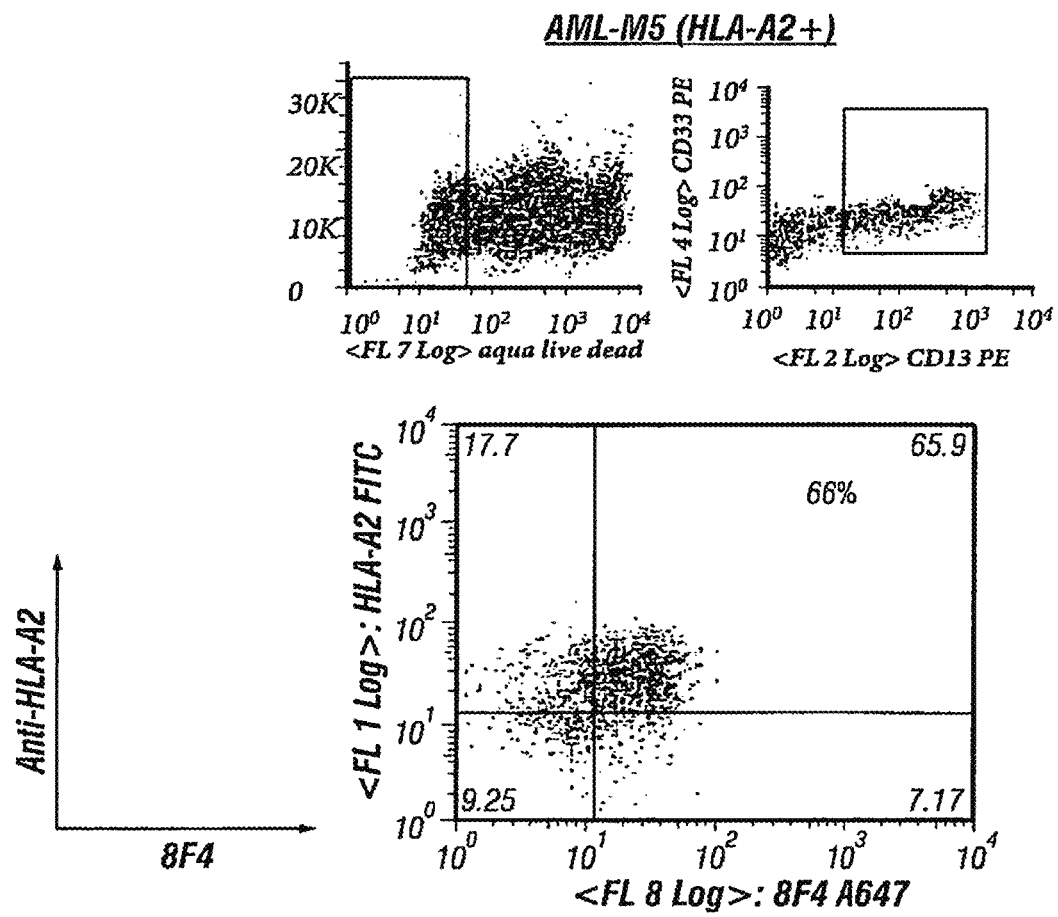
Figure 3:
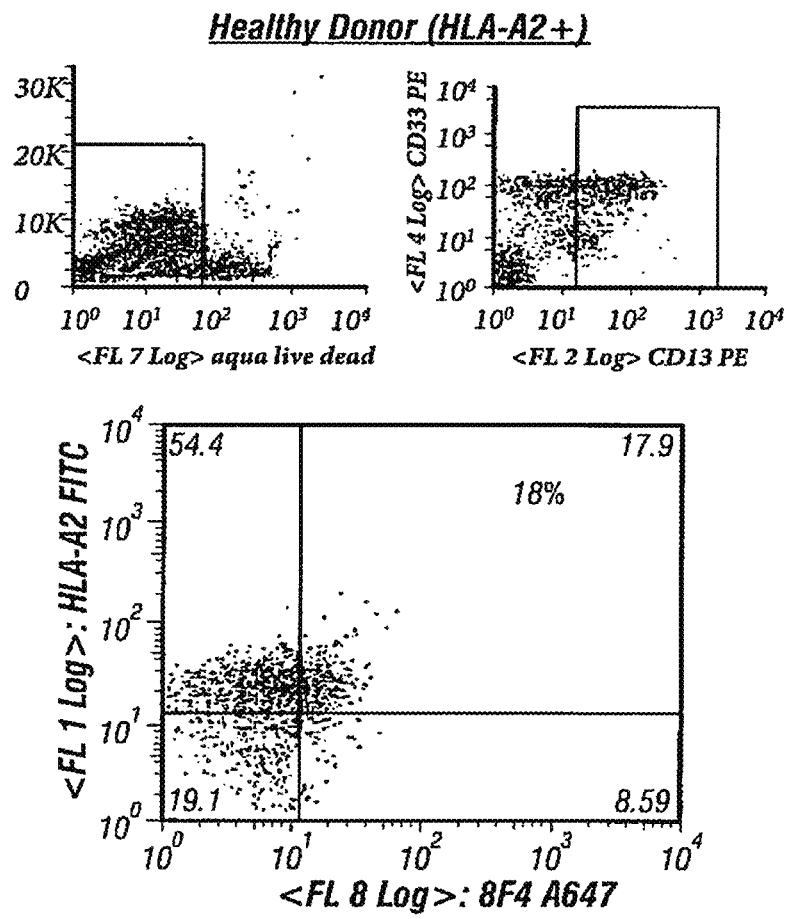
Figure 3:
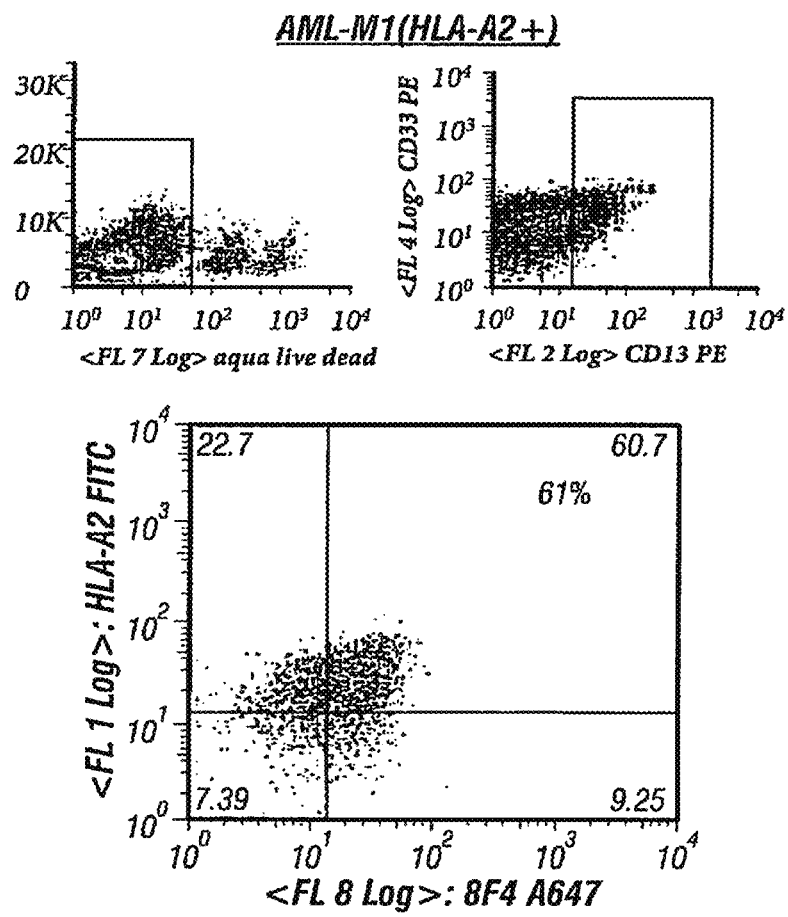
Figure 5:
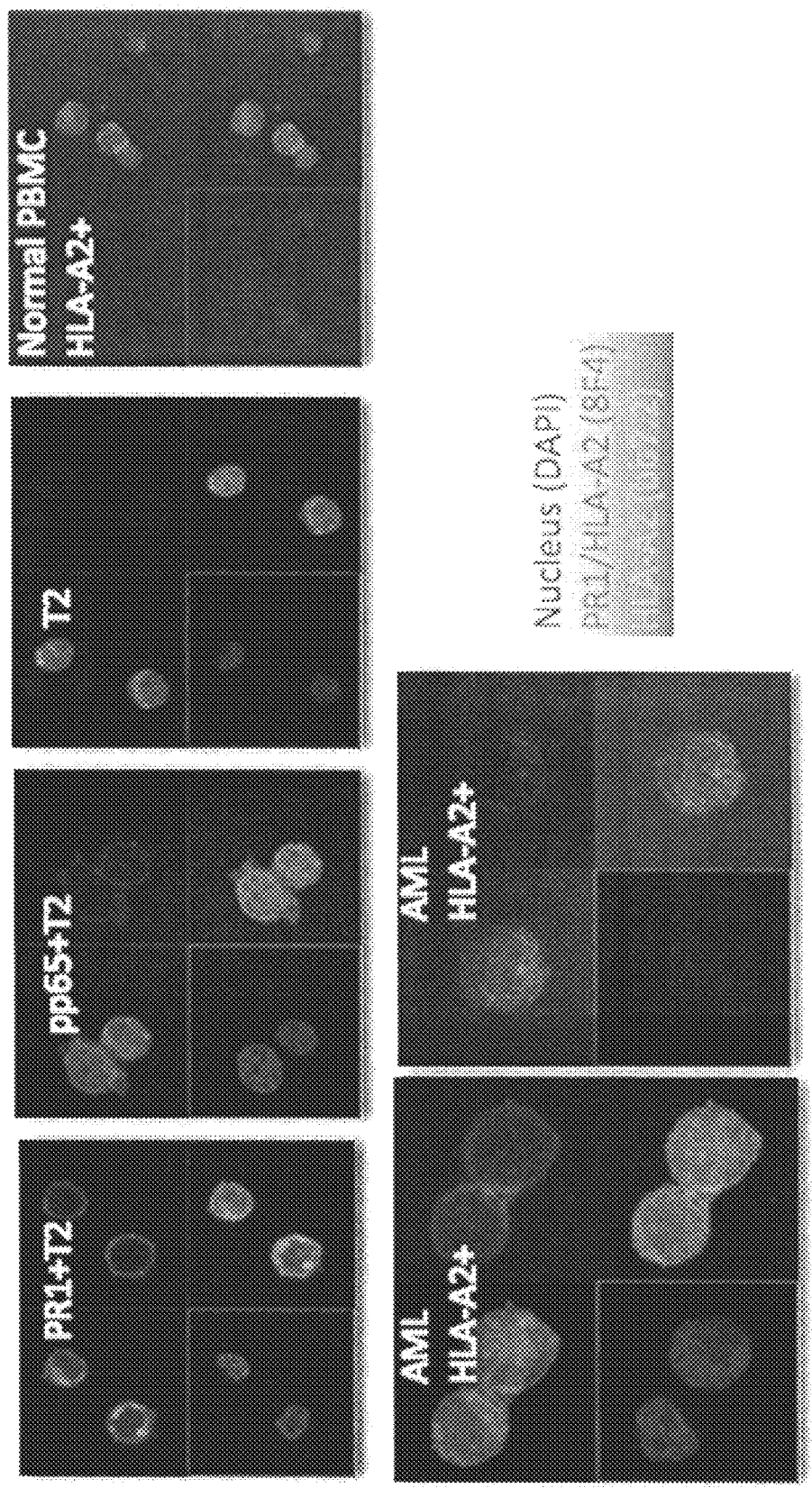
FIG. 5—Specificity of 8F4 for AML But Not Normal PBMC. Surface staining of AML, PBMC, and T2 cell for PR1 and HLA-A2. Cells were stained with anti-PR1/HLA-A2 antibody (8F4)-alexa-647 (red) and anti-HLA-A2-FITC conjugated (green), fixed with 1% paraformaldehyde, and then studied using confocal microscopy. T2 cells were pulsed with PR1 peptide (20 µg/ml) as a positive control and with the CMV peptide pp65 (20 µg/ml) as a negative control peptide. PR1/HLA-A2 expression is evident on the cell surface of AML and PR1-pulsed T2 cells, but not on HLA-A2+ PBMC or on the pp65-pulsed T2 cells. Dapi-blue was used for nuclear staining.

Antibody Binding Assessment. Epitope mapping was performed by folding altered PR1 peptides, containing an Ala substitution at each P1 to P9 position, with the HLA-A*0201 heavy chain plus β2 microglobulin. P1 turned out to be most critical for 8F4 binding, although alteration of all amino acid positions disrupted binding (FIG. 1). Binding affinity of 8F4 to PR1/HLA-A*0201 was determined by surface Plasmon resonance on a Biacore instrument with immobilized 8F4 and increasing concentration of soluble PR1/HLA-A*0201, as shown in FIG. 2. 8F4 $K_D$ is 9.9 nM, compared to $K_D$ of 162 nM for a commercially available BB7.2 murine monoclonal antibody that recognizes a distinct allele-specific site on HLA-A*0201. Using confocal microscopy, direct fluorescence conjugates of 8F4 only bound to PR1 peptide-pulsed T2 cells (that express HLA-A*0201), but not to irrelevant pp65-pulsed or to non-pulsed T2 cells. Taken together, 8F4 specificity for, and high 8F4 binding affinity to the combined PR1/HLA-A*0201 was confirmed. Using both FACS analysis and confocal imaging (again with 8F4, FITC-conjugated BB7.2 anti-HLA-A*0201 antibody, and DAPI), 8F4 was shown to bind to circulating blasts from HLA-A2+ patients with AML but not to PBMC from HLA-A2+ healthy donors nor to HLA-A2 negative AML blasts (FIGS. 3 and 5).

Cloning and sequencing of mouse 8F4 variable region genes. Mouse 8F4 hybridoma cells were grown in RPMI-1640 media (HyClone, Logan, Utah) containing 10% fetal bovine serum (FBS; HyClone) and 1 mM sodium pyruvate at 37° C. in a 7.5% $CO_2$ incubator. Total RNA was extracted from approximately $10^7$ hybridoma cells using TRIzol reagent (Invitrogen, Carlsbad, Calif.) according to the supplier's protocol. Oligo dT-primed cDNA was synthesized using the SMARTer RACE cDNA Amplification Kit (Clontech, Mountain View, Calif.) following the supplier's protocol. The variable region cDNAs for 8F4 heavy and light chains were amplified by polymerase chain reaction (PCR) with PHUSION® DNA polymerase (New England Biolabs, Beverly, Mass.) using 3' primers that anneal respectively to the mouse γ-2a and κ chain constant regions, and a Universal Primer A Mix or Nested Universal Primer A provided in the SMARTer® RACE cDNA Amplification Kit as a 5' primer. For PCR amplification of heavy chain variable region (VH), the 3' primer has the sequence 5'-GCCAGTGGATAGACC-GATGG-3' (SEQ ID NO:46). For PCR amplification of light chain variable region (VL), the 3' primer has the sequence 5'-GATGGATACAGTTGGTGCAGC-3' (SEQ ID NO:47). The amplified VH and VL cDNAs were cloned into the pCR4Blunt-TOPO vector (Invitrogen) for sequence determination. DNA sequencing of the variable regions was carried out at Tocore (Menlo Park, Calif.). Several heavy and light chain clones were sequenced and unique sequences homologous to typical mouse heavy and light chain variable regions were identified. The consensus cDNA sequences along with deduced amino acid sequences of 8F4 VH and VL are shown in FIGS. 1 and 2, respectively. No unusual features were noticed in the mature 8F4 VH and VL amino acid sequences.

Figure 11:
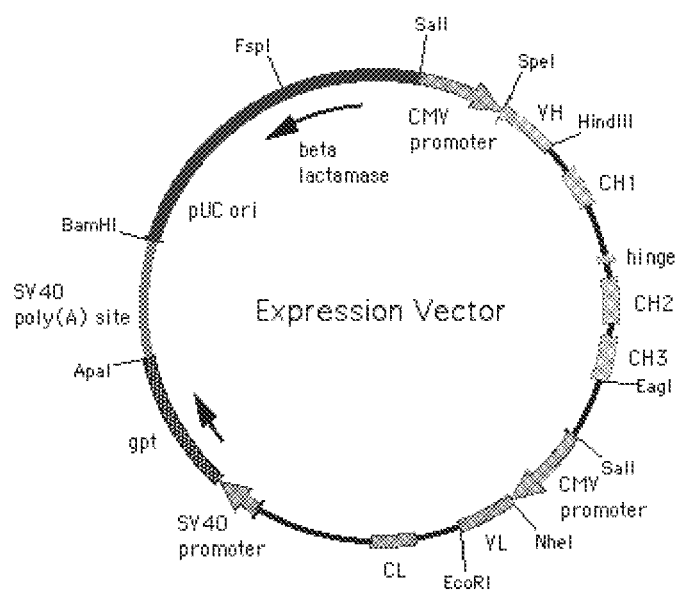
FIG. 11. Schematic structure of pCh8F4, pHu8F4-1, pHu8F4-2 and pHu8F4-2-AA (collectively Expression Vector). Proceeding clockwise from the SalI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human kappa chain constant region exon (CL) with part of the intron preceding it, and the polyadenylation site following the CL exon. The light chain gene is then followed by the SV40 early promoter (SV40 promoter), the *E. coli* xanthine guanine phosphoribosyl transferase gene (gpt), and a segment containing the SV40 polyadenylation site (SV40 poly(A) site). Finally, the plasmid contains a part of the plasmid pUC19, comprising the bacterial origin of replication (pUC ori) and beta-lactamase gene ((β-lactamase).

Construction of chimeric 8F4 IgG1/κ antibody. A gene encoding 8F4 VH was generated as an exon including a splice donor signal and appropriate flanking restriction enzyme sites by PCR using 8F4 VH cDNA as a template, 5'-GCAACTAGTACCACCATGAACTTCGGGCTCAGC-3' (SEQ ID NO:48; SpeI site is underlined) as a 5' primer, and 5'-CGAAAGCTTGAAGTTAGGACT-CACCTGCAGAGAGAGTGACCAGAG-3' (SEQ ID NO:49; HindIII site is underlined) as a 3' primer. Likewise, a gene encoding 8F4 VL was generated as an exon including a splice donor signal and appropriate flanking restriction enzyme sites by PCR using 8F4 VL cDNA as a template, 5'-GCAGCTAGCACCACCATGGAGTCACAGATTCAG-3' (SEQ ID NO:50; NheI site is underlined) as a 5' primer, and 5'-CGAGAATTCTTTGGATTCTACTTACGTTTGAT-TTCCAGCTTGGTG-3' (SEQ ID NO:51; EcoRI site is underlined) as a 3' primer. The splice donor signals of the 8F4 VH and VL exons were derived from the mouse germline JH3 and Jκ1 sequences, respectively. PCR-amplified fragments were gel-purified using NUCLEOSPIN® Extraction II Kit (Macherey-Nagel, Bethlehem, Pa.) and cloned into the pCR4Blunt-TOPO vector (Invitrogen) for sequence confirmation. The correct V fragments were digested with SpeI and HindIII (for VH) or NheI and EcoRI (for VL), gel-purified and cloned into a mammalian expression vector carrying human γ-1 and κ constant regions for production of chimeric 8F4 IgG1/κ antibody. The schematic structure of the resulting expression vector, pCh8F4, is shown in FIG. 11.

Generation of humanized 8F4 VH and VL genes. Designing of humanized 8F4 VH and VL amino acid sequences was carried out as follows. First, a three-dimensional molecular model of the 8F4 variable regions was constructed using JN Biosciences' proprietary algorithm. Next, the framework amino acid residues important for the formation of the CDR structure were identified using the molecular model. In parallel, cDNA-derived human VH and VL amino acid sequences with high homology to 8F4 VH and VL, respectively, were selected. Finally, CDR sequences together with framework amino acid residues important for maintaining the CDR structure were grafted from 8F4 VH and VL into the corresponding selected human framework sequences.

Human VH sequences homologous to the 8F4 VH frameworks were searched for within the GenBank database, and the VH sequence encoded by the human U96282 cDNA (U96282 VH) (GenBank accession number; Rassenti and Kipps, J. Exp. Med. 185: 1435, 1997) was chosen as an acceptor for humanization. The CDR sequences of 8F4 VH were first transferred to the corresponding positions of U96282 VH. No substitution of human framework amino acids was predicted to be necessary to maintain the CDR structure. The amino acid sequence of the resulting humanized VH, Hu8F4 VH, alongside with 8F4 and U96282 VH sequences, is shown in FIG. 12.

Based on the homology search with the 8F4 VL framework sequences, the human Vκ region encoded by the AY043146 cDNA (AY043146 VL) (GenBank accession number; Ghiotto et al., submitted to GenBank on Jun. 29, 2001) was chosen as an acceptor for humanization. CDR sequences of 8F4 VL were first transferred to the corresponding positions of AY043146 VL. Next, at framework position 70, where the analysis of the three-dimensional model of the 8F4 variable regions indicated contact with the CDRs, an amino acid residue from mouse 8F4 VL was substituted for the corresponding human residue. The amino acid sequence of the resulting humanized VL, Hu8F4 VL1, is shown alongside with 8F4 and AY043146 VL sequences in FIG. 13.

While Val at position 70 in mouse 8F4 VL is located at a framework position important for the formation of the CDR structure, detailed analysis of the molecular model of the 8F4 variable regions suggested a possibility that an amino acid residue at position 70 in Hu8F4 VL1 could be replaced with the human corresponding residue, Asp, in AY043146 VL without losing the antigen-binding affinity. In order to further reduce potential immunogenicity of humanized 8F4 antibody, a second humanized VL (Hu8F4 VL2) was designed, in which Val at position 70 in Hu8F4 VL1 was replaced with Asp. The amino acid sequence of Hu8F4 VL2 is shown in FIG. 13.

A gene encoding Hu8F4 VH was designed as an exon including a signal peptide, a splice donor signal, and appropriate restriction enzyme sites for subsequent cloning into a mammalian expression vector. The splice donor signal of the Hu8F4 VH exon was derived from the human germline JH3 sequence. The signal peptide sequence in the humanized Hu8F4 VH exon was derived from the corresponding mouse 8F4 VH sequence.

Each of the genes encoding Hu8F4 VL1 and VL2 was designed as an exon including a signal peptide, a splice donor signal, and appropriate restriction enzyme sites for subsequent cloning into a mammalian expression vector. The splice donor signal of the Hu8F4 VL1 and VL2 exons was derived from the human germline Jκ4 sequence. The signal peptide sequence in the humanized Hu8F4 VL1 and VL2 exons was derived from the corresponding mouse 8F4 VL sequence.

The Hu8F4 VH, VL1 and VL2 genes were constructed by GENSCRIPT® USA (Piscataway, N.J.) under a confidentiality non-disclosure agreement. After digestion with SpeI and HindIII (for VH) or NheI and EcoRI (for VL), Hu8F4 VH, VL1 and VL2 genes were subcloned into corresponding sites in a mammalian expression vector for production in the human IgG1/κ form. The resulting expression vector, pHu8F4-1, expresses humanized 8F4 IgG1/κ antibody containing Hu8F4 VH and VL1 (Hu8F4-1). Likewise, pHu8F4-2 expresses humanized 8F4 IgG1/κ antibody containing Hu8F4 VH and VL2 (Hu8F4-2). The schematic structure of pHu8F4-1 and pHu8F4-2 is shown in FIG. 11. The nucleotide sequences of the Hu8F4 VH, VL1 and VL2 genes along with deduced amino acid sequences are shown as SEQ ID NOS: 22/23, 24/25 and 26/27, respectively.

The Hu8F4 VH and VL2 genes were also cloned into another mammalian expression vector for production of a variant human IgG1/κ form termed IgG1-AA. The IgG1-AA form carries two amino acid substitutions in the γ-1 heavy chain from Leu to Ala at position 234 and Leu to Ala at position 235 (Eu numbering; Kabat et al., 1991), resulting in severely reduced binding to Fc γ receptors (U.S. Pat. No. 6,491,916). The schematic structure of the resultant plasmid, pHu8F4-2-AA, is shown in FIG. 11.

Generation of NS0 stable transfectants producing chimeric and humanized 8F4 IgG1/κ antibodies. To obtain cell lines stably producing Ch8F4, Hu8F4-1, Hu8F4-2 and Hu8F4-2-AA IgG1/κ antibodies, the expression vectors pCh8F4, pHu8F4-1, pHu8F4-2 and pHu8F4-2-AA, respectively, were introduced into the chromosome of a mouse myeloma cell line NS0 (European Collection of Animal Cell Cultures, Salisbury, Wiltshire, UK). NS0 cells were grown in DME medium containing 10% FBS at 37° C. in a 7.5% $CO_2$ incubator. Stable transfection into NS0 was carried out by electroporation as described in Bebbington et al. (*Bio/Technology* 10: 169-175, 1992). Before transfection, each expression vector was linearized using FspI. Approximately $10^7$ cells were transfected with 20 µg of linearized plasmid, suspended in DME medium containing 10% FBS, and plated into several 96-well plates. After 48 hr, selection media (DME medium containing 10% FBS, HT media supplement (Sigma, St. Louis, Mo.), 0.25 mg/ml xanthine and 1 µg/ml mycophenolic acid) was applied. Approximately 10 days after the initiation of selection, culture supernatants were assayed for antibody production.

Expression of chimeric and humanized 8F4 IgG1/κ antibodies was measured by sandwich ELISA. In typical experiments, an ELISA plate was coated overnight at 4° C. with 100 µl/well of 1/2,000-diluted goat anti-human IgG Fcγ-chain-specific polyclonal antibody (Sigma) in PBS, washed with Wash Buffer (PBS containing 0.05% Tween 20), and blocked for 0.5 hr at room temperature with 300 µl/well of Block Buffer (PBS containing 2% Skim Milk and 0.05% Tween 20). After washing with Wash Buffer, 100 µl/well of samples appropriately diluted in ELISA Buffer (PBS containing 1% Skim Milk and 0.025% Tween 20) were applied to the ELISA plate. An appropriate humanized IgG1/κ antibody was used as a standard. After incubating the ELISA plate for 1 hr at room temperature and washing with Wash Buffer, bound antibodies were detected using 100 µl/well of 1/2,000-diluted HRP-conjugated goat anti-human kappa chain polyclonal antibody (Southern Biotech). After incubating for 0.5 hr at room temperature and washing with Wash Buffer, color development was performed by adding 100 µl/well of ABTS substrate (bioWORLD, Dublin, Ohio). Color development was stopped by adding 100 µl/well of 2% oxalic acid. Absorbance was read at 405 nm. NS0 stable transfectants producing a high level of Ch8F4, Hu8F4-1, Hu8F4-2 and Hu8F4-2-AA antibodies (NS0-Ch8F4 1-G8, NS0-Hu8F4-1 1-D2, NS0-Hu8F4-2 1-F5 and NS0-Hu8F4-2-AA 1D3, respectively) were adapted to growth in serum-free media using Hybridoma-SFM (Invitrogen). Testing with the PCR Mycoplasma Detection Set (Takara Bio USA, Madison, Wis.) indicated that NS0-Ch8F4 1-G8, NS0-Hu8F4-1 1-D2, NS0-Hu8F4-2 1-F5 and NS0-Hu8F4-2-AA 1D3, were negative for the presence of mycoplasma.

The authenticity of heavy and light chains produced in NS0-Ch8F4 1-G8, NS0-Hu8F4-1 1-D2, NS0-Hu8F4-2 1-F5 and NS0-Hu8F4-2-AA 1D3 was confirmed by cDNA sequencing. Total RNA was extracted from cells using TRIzol® reagent (Invitrogen) and oligo dT-primed cDNA was synthesized using the SUPERSCRIPT III® First-Strand Synthesis System for RT-PCR (Invitrogen) following supplier's protocols. The coding region of γ-1 heavy chain was amplified by PCR using CMV2 and JNT098 as primers (FIG. 11) and PHUSION® DNA polymerase. PCR fragments were gel-purified and subjected to sequencing with CMV2, JNT082, JNT097 and JNT098 as primers shown as SEQ ID NOS: 28 and 30-32. Similarly, the coding region of κ light chain was amplified using CMV2 and JNT026 (SEQ ID NOS: 28 and 29). Gel-purified DNA fragments were subjected to sequencing with CMV2 and JNT026 as primers. The obtained nucleotide sequence of the coding region for each of Ch8F4 heavy chain (SEQ ID NO: 33), Ch8F4 light chain (SEQ ID NO: 35), Hu8F4-1 heavy chain (SEQ ID NO: 37), Hu8F4-1 light chain (SEQ ID NO: 39), Hu8F4-2 heavy chain (SEQ ID NO: 37), Hu8F4-2 light chain (SEQ ID NO: 41), Hu8F4-2-AA heavy chain (SEQ ID NO: 43), and Hu8F4-2-AA light chain (SEQ ID NO: 41) matched perfectly with the corresponding sequence in the pCh8F4, pHu8F4-1, pHu8F4-2 or pHu8F4-2-AA vector.

Purification of 8F4-4, Ch8F4, Hu8F4-1, Hu8F4-2 and Hu8F4-2-AA antibodies. Hybridoma 8F4-4 (provided by Dr. Molldrem) was cultured in RPMI media (Hyclone) containing 10% FBS, and adapted to growth in Hybridoma-SFM. 8F4-4, NS0-Ch8F4 1-G8, NS0-Hu8F4-1 1-D2, NS0-Hu8F4-2 1-F5 and NS0-Hu8F4-2-AA 1D3 cells were grown in Hybridoma-SFM in a roller bottle to the density of about $10^6$/ml, fed with $\frac{1}{10}^{th}$ volume of 60 mg/ml of Ultrafiltered Soy Hydrolysate (Irvine Scientific, Santa Ana, Calif.) dissolved in SFM4MAb media (HyClone), and grown further until the cell viability became less than 50%. After centrifugation and filtration, culture supernatant was loaded onto a Protein-A Sepharose column (HITRAP MABSELECT SURE®, GE Healthcare, Piscataway, N.J.). The column was washed with PBS before the antibody was eluted with 0.1 M glycine-HCl (pH 3.0). After neutralization with 1 M Tris-HCl (pH 8), the buffer of eluted antibody was changed to PBS by dialysis. Antibody concentration was determined by measuring absorbance at 280 nm (1 mg/ml=1.4 OD). Purification and yield of each batch of 8F4-4, Ch8F4, Hu8F4-1, Hu8F4-2 and Hu8F4-2-AA is summarized in Table 5.

TABLE 5

| Antibody | Lot | Yields |
| --- | --- | --- |
| 8F4-4 | Jan. 27, 2011 | 30 mg from 1 L culture |
| Ch8F4 | Aug. 10, 2010 | 7 mg from 500 mL culture |
| Hu8F4-1 | Sep. 8, 2010 | 6.5 mg from 1 L culture |
| Hu8F4-2 | Sep. 9, 2010 | 11 mg from 1 L culture |
| Hu8F4-2 | Jan. 23, 2011 | 21 mg from 1 L culture |
| Hu8F4-2-AA | Mar. 15, 2011 | 10 mg from 500 mL culture |

Various purification lots and yields of 8F4-4, Ch8F4, Hu8F4-1, Hu8F4-2 and Hu8F4-2-AA.

Figure 14:
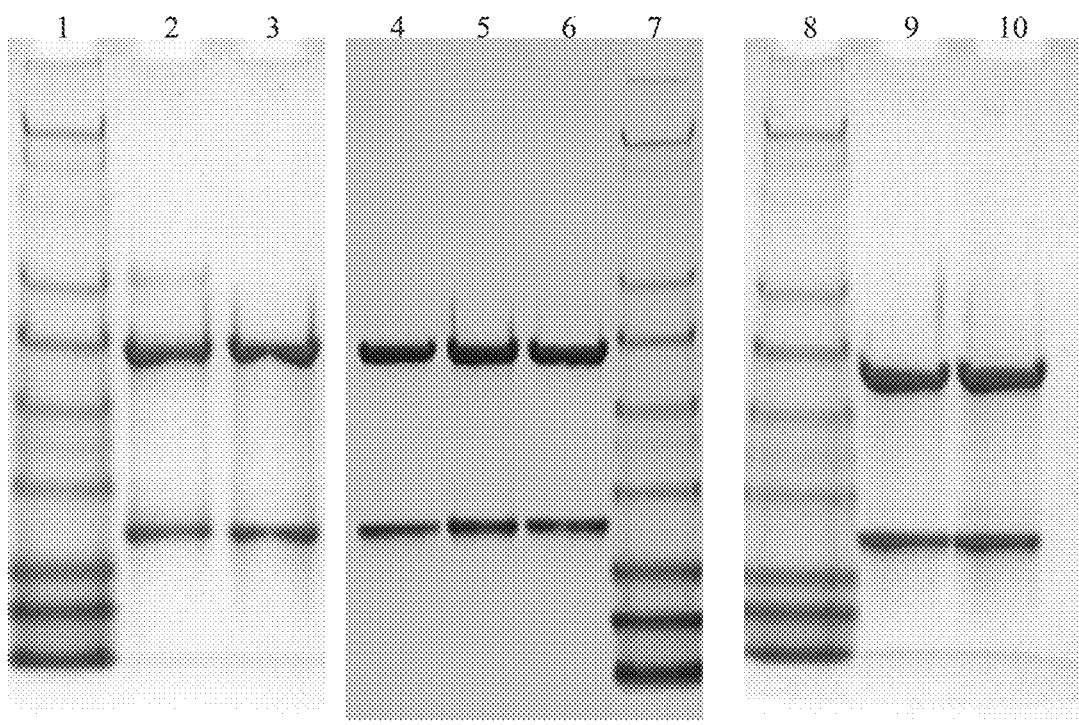
FIG. 14. SDS PAGE analysis of purified 8F4 antibodies. Antibodies (5 µg each) were run on a 4-20% SDS PAGE gel under reducing conditions. Invitrogen's SEEBLUEPLUS2® Prestained Standard (Cat #LC5925) was used as molecular weight standards (lanes 1, 7 and 8). Samples: 8F4.3.3 (lane 2), 8F4-4 (lane 3), Ch8F4 (lane 4), Hu8F4-1 (lane 5), Hu8F4-2 lot 9/9/10 (lane 6), Hu8F4-2 lot 1/23/11 (lane 9) and Hu8F4-2-AA (lane 10).

Purified 8F4-4, Ch8F4, Hu8F4-1, Hu8F4-2 and Hu8F4-2-AA were characterized by SDS-PAGE according to standard procedures. Analysis under reducing conditions indicated that each of the antibodies is comprised of a heavy chain with a molecular weight of about 50 kDa and a light chain with a molecular weight of about 25 kDa (FIG. 14). The purity of each antibody appeared to be more than 95%.

Figure 15:
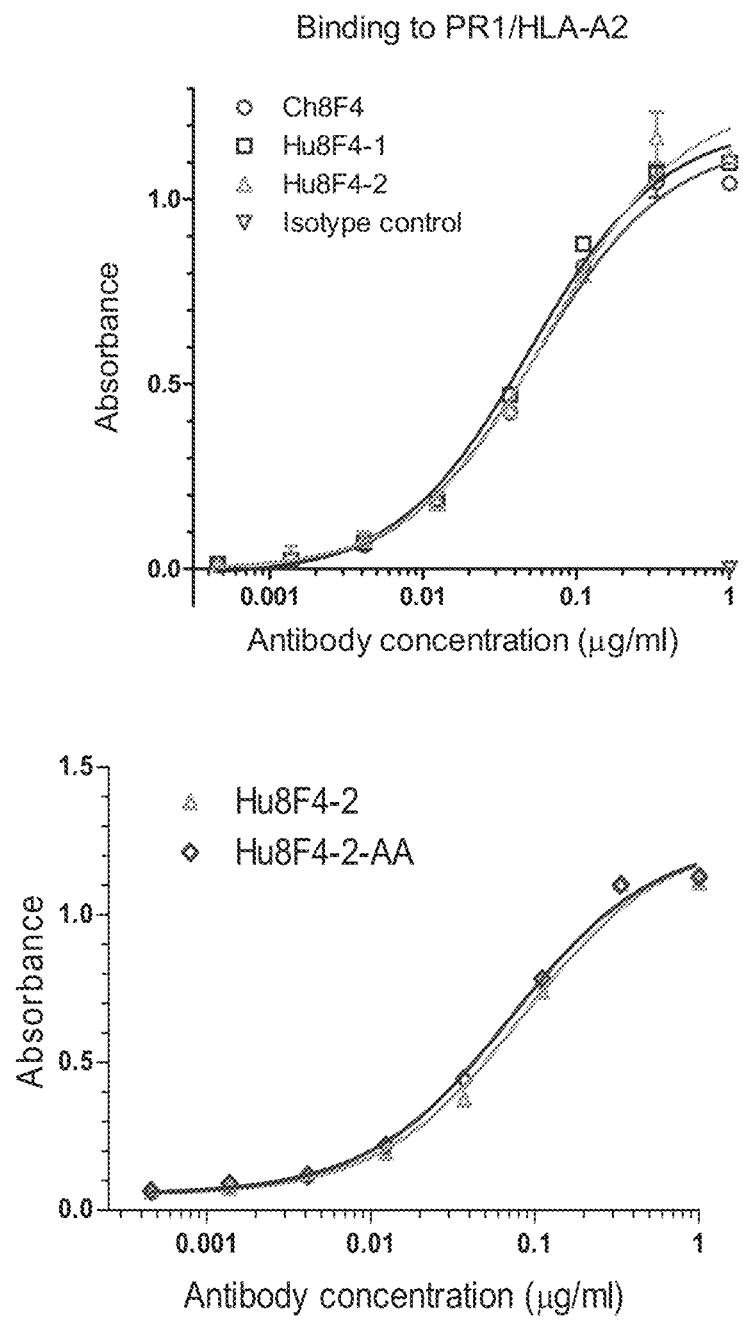
FIG. 15. ELISA analysis of the binding of Ch8F4, Hu8F4-1, Hu8F4-2 and Hu8F4-2-AA to PR-1/HLA-A2. Ch8F4, Hu8F-1, Hu8F4-2 and Hu8F-2-AA were tested at various concentrations, starting at 1 µg/ml and serial 3-fold dilutions, for binding to PR-1/HLA-A2.

Characterization of Ch8F4 and Hu8F4 antibodies. Antigen binding of Ch8F4, Hu8F4-1, Hu8F4-2 and Hu8F4-2-AA was examined by ELISA using the complex of PR1 peptide (VLQELNVTV (SEQ ID NO:45)) with HLA-A2 (PR1/HLA-A2). An ELISA plate was first coated with 100 µl/well of 5 µg/ml streptavidin (Jackson ImmunoResearch, West Grove, Pa.) in PBS. After washing wells with Wash Buffer (PBS containing 0.05% Tween 20) and blocking with Block Buffer, 50 µl/well of 2 µg/ml biotinylated PR1/HLA-A2, which had been provided by Dr. Molldrem, was added. After 30 min incubation at room temperature, the ELISA plate was washed with Wash Buffer. Ch8F4, Hu8F4-1, Hu8F4-2 and Hu8F4-2-AA antibodies were added, starting at 1 µg/ml and serial 3-fold dilutions in ELISA Buffer, for binding to PR1/HLA-A2. After incubating the ELISA plate for 1 hr at room temperature and washing with Wash Buffer, bound antibodies were detected using 100 µl/well of 1/2,000-diluted HRP-conjugated goat anti-human kappa chain polyclonal antibody. After incubating for 30 min at room temperature and washing with Wash Buffer, color development was performed by adding 100 µl/well of ABTS substrate. Color development was stopped by adding 100 µl/well of 2% oxalic acid. Absorbance was read at 405 nm. The data is shown in FIG. 15. $EC_{50}$ values calculated using GraphPad Prism (GraphPad Software, San Diego, Calif.) were 0.054 µg/ml for Ch8F4, 0.050 µg/ml for Hu8F4-1, 0.07 µg/ml for Hu8F4-2, and 0.07 µg/ml for Hu8F4-2-AA. This result indicates that Hu8F4-1, Hu8F4-2 and Hu8F4-2-AA all retain the antigen binding affinity of mouse 8F4 antibody.

Figure 4:
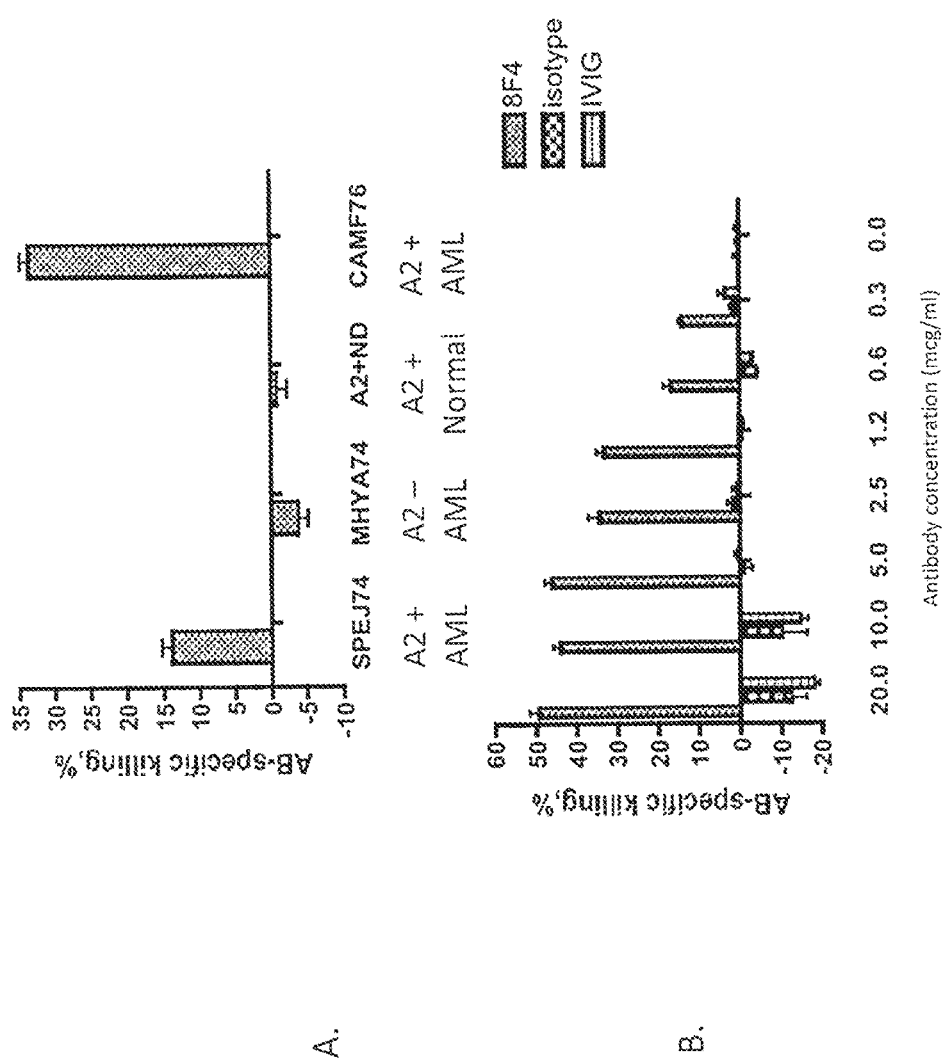
Figure 6:
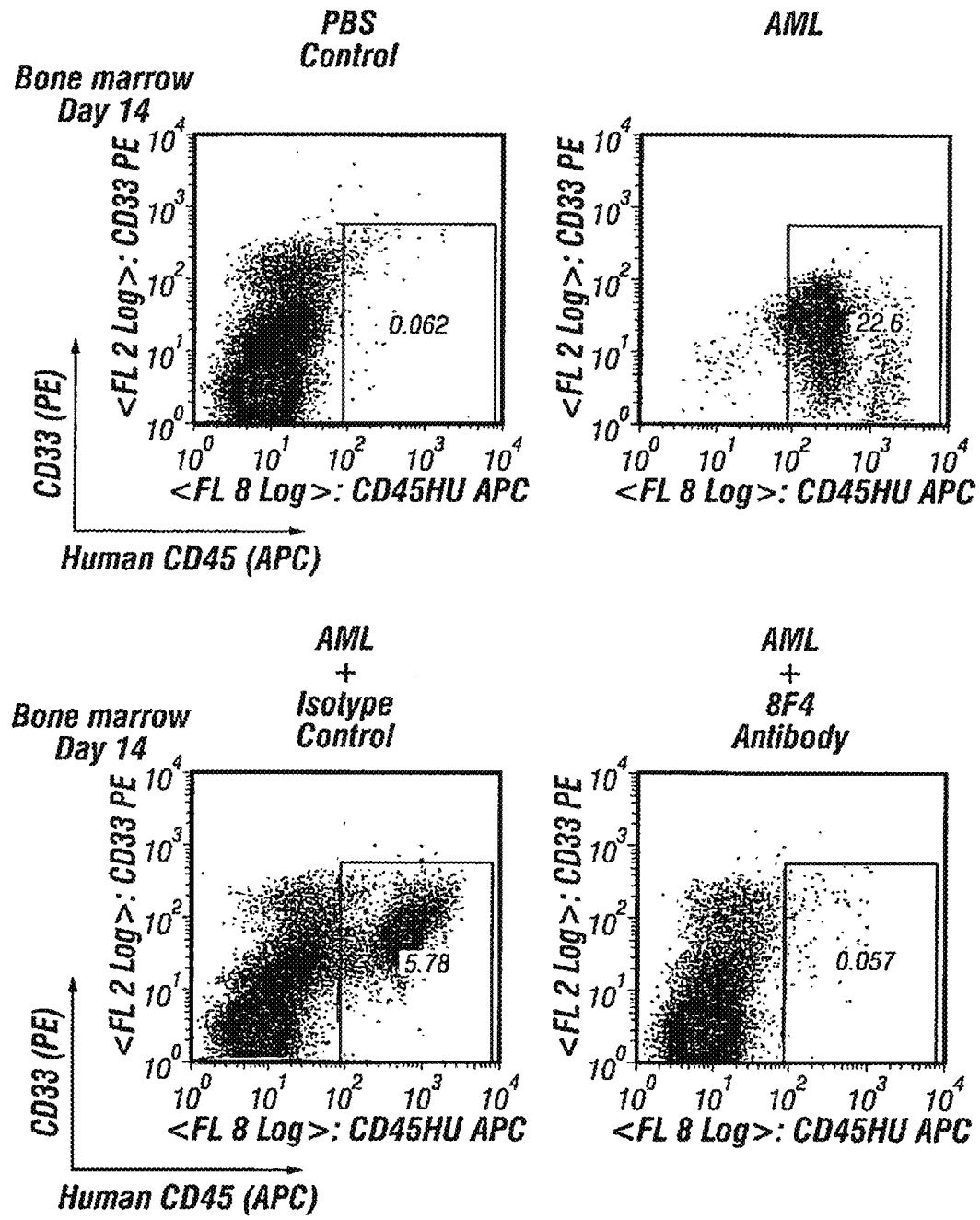
Figure 7:
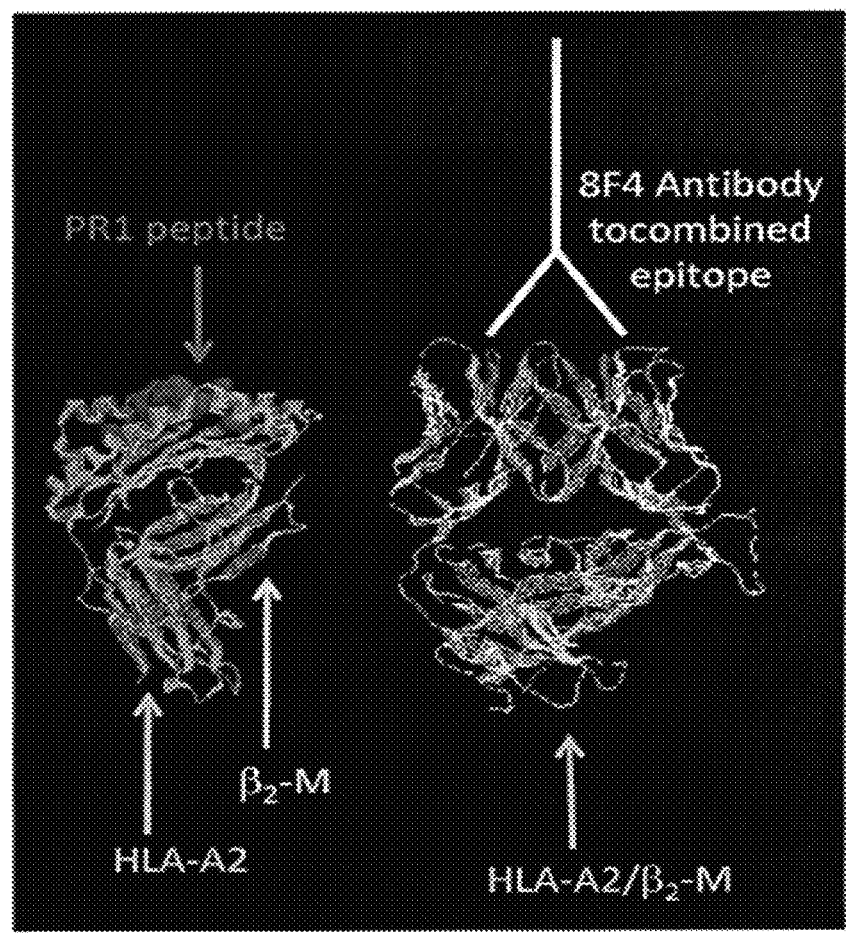
FIG. 7—Immunization Strategy to Obtain Anti-PR1/HLA-A2 Antibody. Schematic representation of MHC class I molecule. MHC class consists of heavy chain and a β2 microglobulin chain. Peptide antigen binds into the groove of the MHC-I, flanked by α1 and α2 helical domains of the chain.

Antibody Action Against Target Cells. To determine whether binding of 8F4 to AML triggers cell lysis, antibody-dependent cellular cytotoxicity (ADCC) and complement-dependent cytotoxicity (CDC) assays were performed. CDC-mediated lysis of HLA-A2+ AML by 8F4, but not HLA-A2 negative AML or HLA-A2+ healthy donor control PBMC, was shown to be antibody dose-dependent (FIG. 4). AML cells from patient material that was shown to be sensitive to 8F4 CDC-mediated lysis were incubated in the presence or absence of 8F4 or isotype control and then transferred into irradiated (200 cGy) immunodeficient HLA-A2 transgenic NOD/SCID mice. At two weeks the animals were sacrificed and splenocytes and bone marrow were analyzed by FACS. At necropsy, AML was identified only in the IgG2a isotype control-treated animal but not in the 8F4-treated animal (FIG. 6). There was no apparent toxicity in the mice that received 8F4 alone compared to the isotype-treated mice. In total, these data support the conclusion that 8F4 monoclonal antibody: (1) specifically binds with high affinity to the combined PR1/HLA-A*0201 epitope; (2) specifically binds to, and can be used to identify PR1 peptide-occupied HLA-A*0201 molecules on the surface of human cells, including myeloid leukemia; (3) causes specific lysis of HLA-A2+ AML in the presence of complement; (4) can prevent engraftment of AML in an immunodeficient mouse model.

Figure 8A:
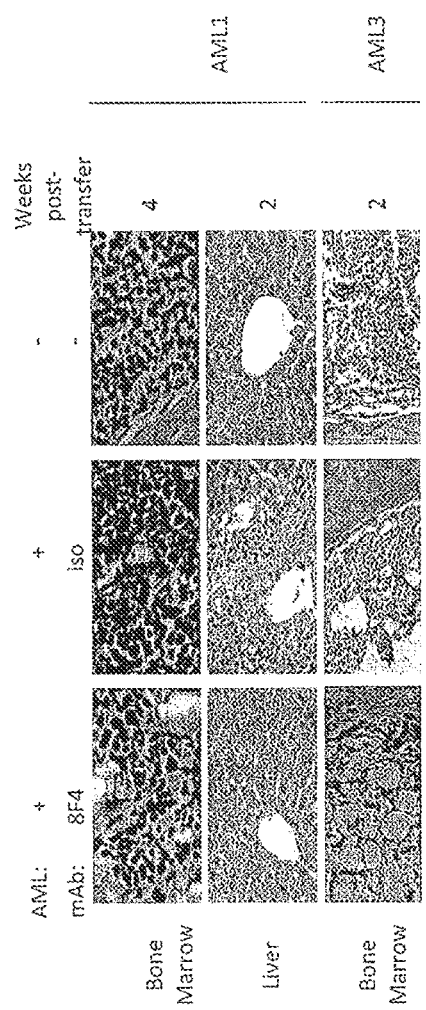
Figure 8B:
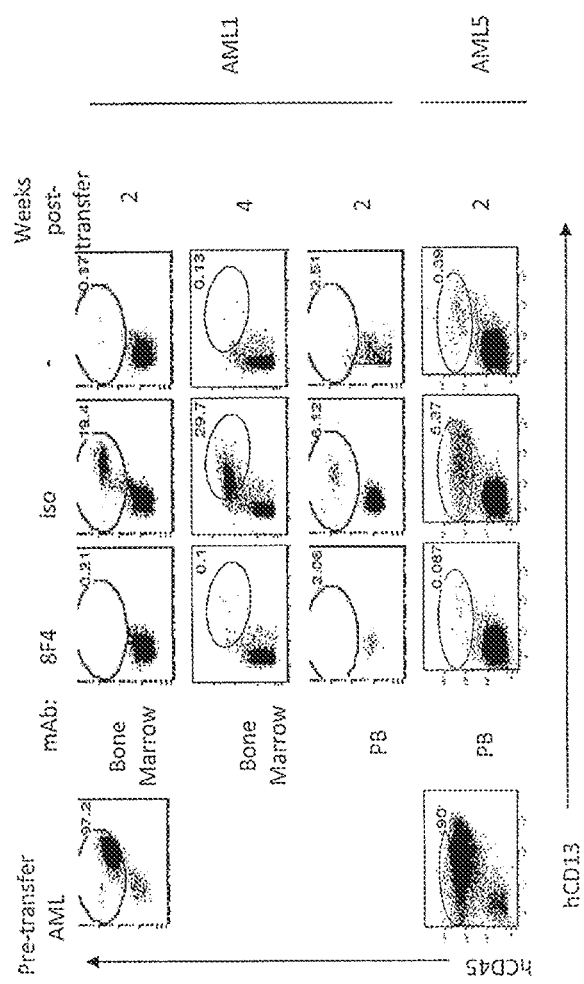

Prevention of Tumor Engraftment. AML infiltration in tissues of experimental mice following injection with AML cells plus 8F4 was measured and is shown in FIGS. 8A-B.

AML cells were not detected in the bone marrow and peripheral blood of no transfer control and experimental 8F4-treated mice. Mice that received AML cells mixed with isotype matched control antibody (iso) showed engraftment of AML1 and AML5 two or four weeks after AML transfer. An extended panel, including a mouse cell specific marker (mCD45), 3-6 human markers (CD45, CD13, CD33, CD34, CD38, HLA-DR), and Live/Dead Fixable Aqua (Invitrogen) was used for flow cytometric analysis of AML engraftment. All plots show viable mCD45-cells.

Figure 9A:
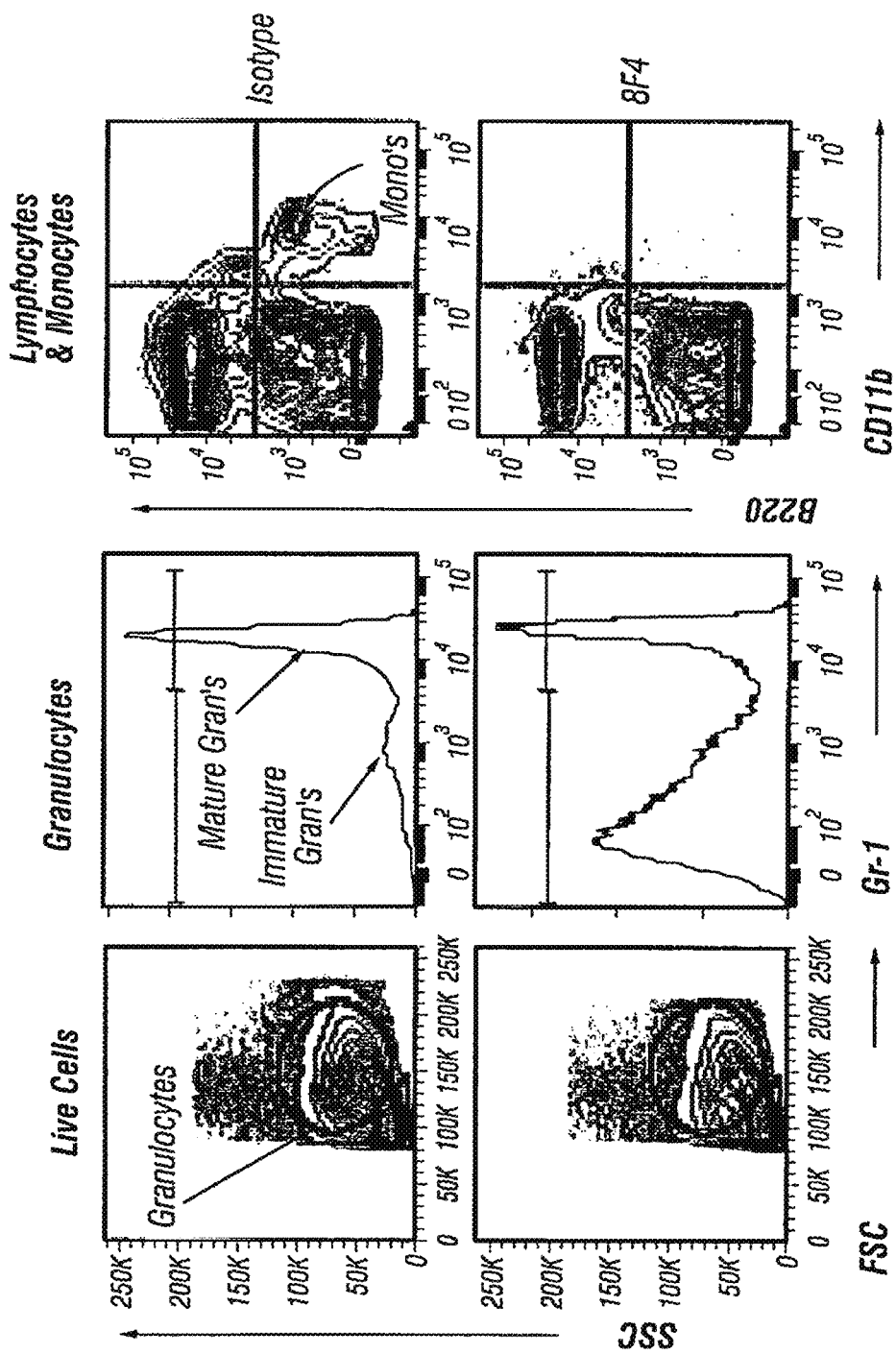
Figure 9B:
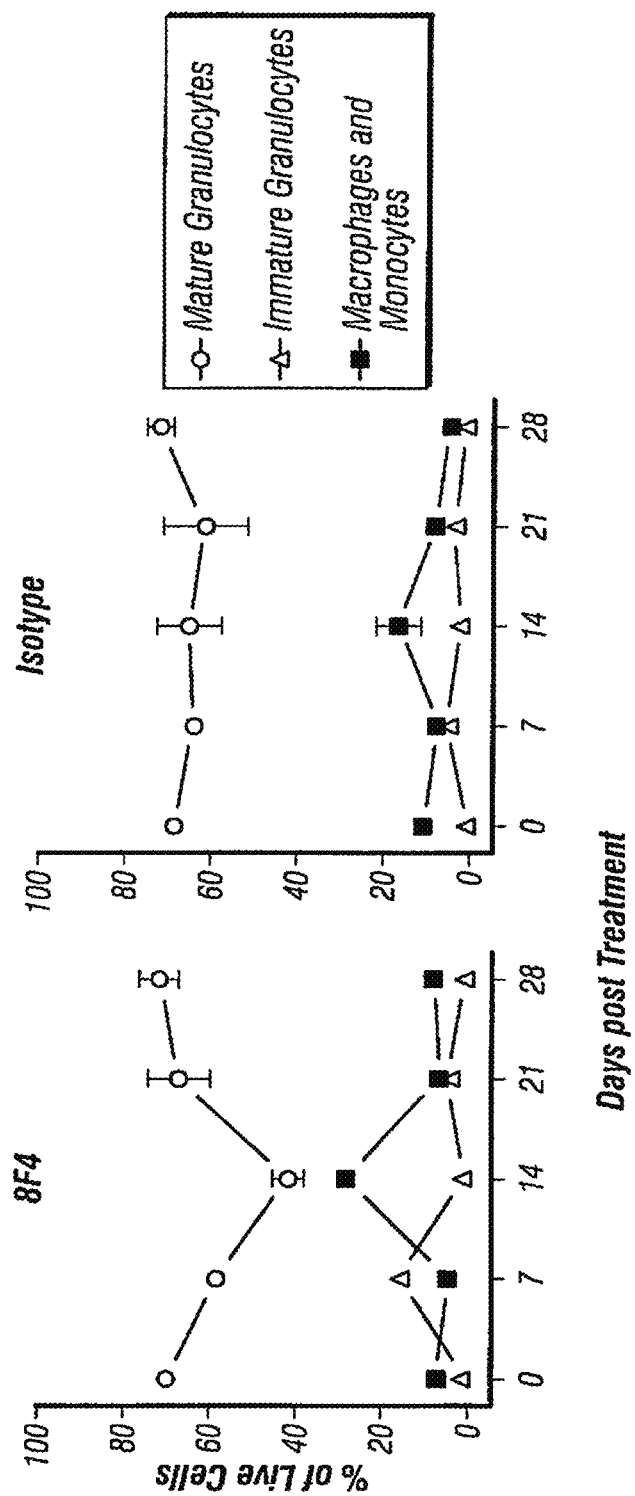

8F4 Induces Transient Neutropenia in HLA-A2 Transgenic NOD/SCID. HLA-A2 Tg NOD/SCID, shown to present endogenous PR1, were injected with 8F4 or control Ab. Bone marrow cells were harvested and stained with mAb directed to mouse antigens. Reduced granulocytes were evident in scatter profiles of bone marrow (FIG. 9A; left panels). Gr-1lo immature neutrophils were present, but Gr-1hi mature neutrophils were less numerous in the bone marrow of 8F4-treated mice (FIG. 9A; center panels). Additionally, monocytes (SSClo CD11b+; FIG. 9A; lower right gate of right panels) were reduced in 8F4-treated animals. Intravenous injection of 8F4 induced transient reduction in absolute numbers of circulating mature granulocytes, macrophages and monocytes in HLA-A2 Tg NOD/SCID mice (FIG. 9B). Three weeks after treatment, all populations remain. No significant pathological changes were evident in liver, lung, spleen, kidney, heart or brains of HLA-A2 Tg NOD/SCID mice 7 days after injection of 200 µg (10 mg/kg) 8F4 (FIG. 9C).

8F4 Induces Transient Leukopenia of Established Human Hematopoietic Cells. Peripheral blood from mice was taken to monitor cord blood engraftment, and 9-12 weeks after transfer mice were injected with 8F4. Mice were subsequently sacrificed and blood, spleen and bone marrow were analyzed for engraftment of human cells (FIG. 10B). As can be seen, the antibody injection transiently reduces the % engraftment of transferred cells (FIG. 10A).

Figure 16A:
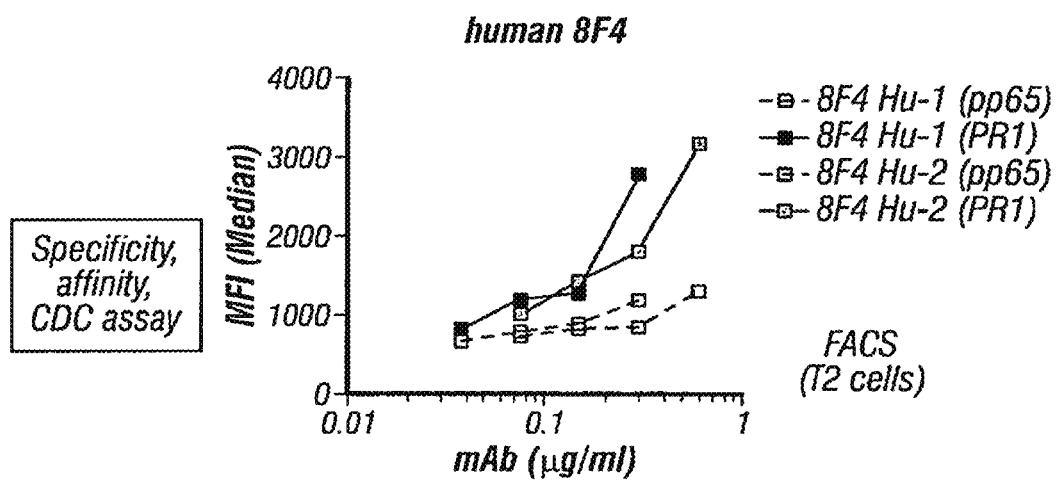
FIGS. 16A-C. Hu8F4 binding specificity and mechanism of action.
Figure 16B:
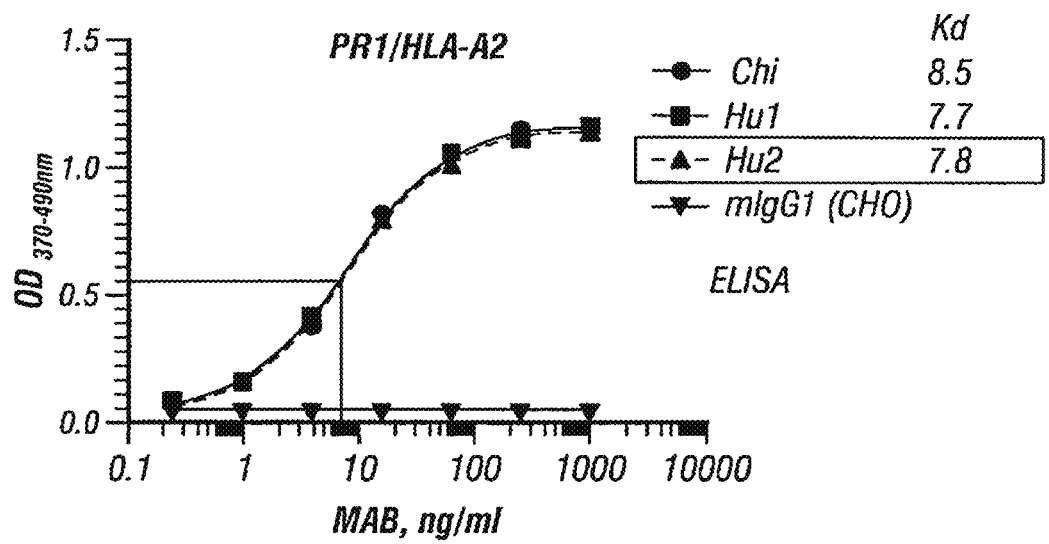

Binding specificity, affinity, and activity of humanized 8F4 antibodies against human AML. To characterize the binding specificity of Hu8F4, the inventors conducted a FACS-based assay to show that Hu8F4 binds only to PR1-pulsed T2 cells (FIG. 16A), but not to pp65-pulsed T2 cells. To characterize the binding affinity of Hu8F4, the inventors used an ELISA comparing the binding of two forms of the humanized antibodies, Hu8F4-1 (Hu1) and Hu8F4-2 (Hu2) with mouse 8F4 and isotype control (rhIgG1). The inventors used recombinant PR1/HLA-A2 monomer-coated plates to capture the antibody, and anti-human antibodies were used in a colorimetric assay to determine the bound fraction by optical density (OD). As shown in FIG. 16B, Hu1 and Hu2 showed $K_D$ of 7.7 and 7.8 nM, respectively, which was similar to mouse 8F4 ($K_D$=9.9 nM). Therefore, the two humanized antibodies have identical ligand specificity and binding affinity compared to the parent mouse antibody. This data establish the biochemical justification for using the Hu8F4 antibodies in further experiments to determine spectrum of activity in the pre-clinical animal models.

Figure 16C:
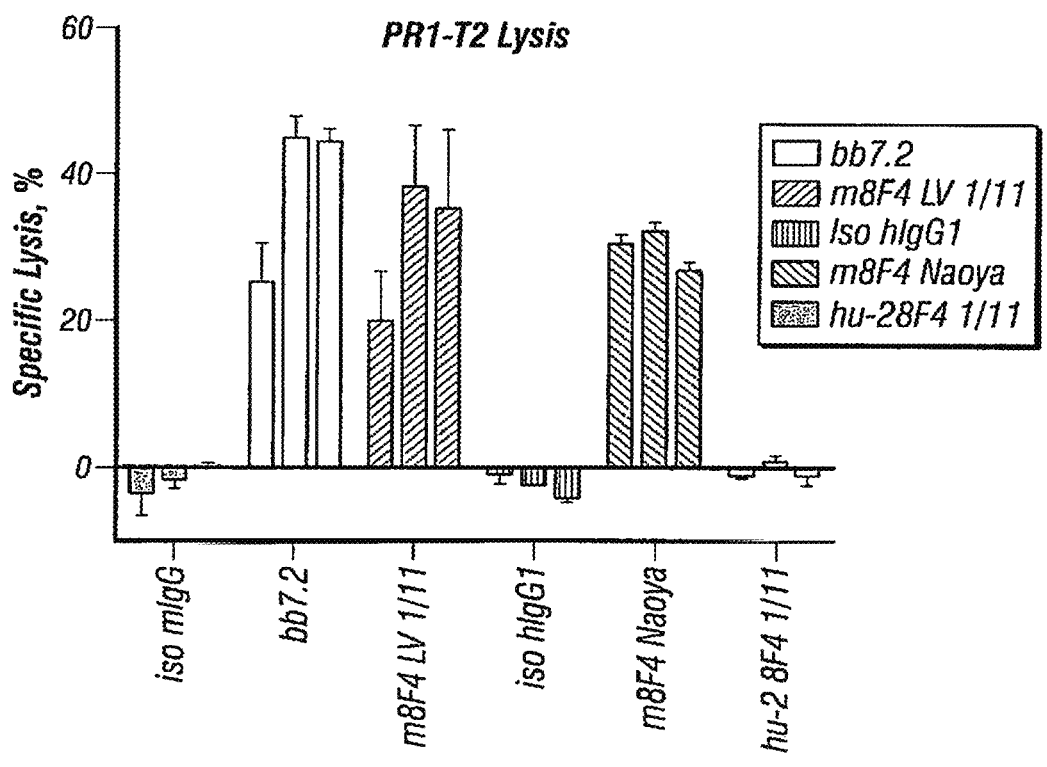

To address a potential mechanism of action of Hu8F4, the inventors treated PR1-pulsed T2 target cells with Hu8F4 or isotype control antibody (IgG1) in the presence of rabbit complement and determined complement-mediated lysis using a standard assay. As shown in FIG. 16C, neither Hu8F4 nor the chimeric Ch8F4 (human Fc from IgG1 and mouse F(ab)$_2$ from 8F4) mediated complement-dependent cytotoxicity (CDC). Therefore, unlike mouse 8F4 (IgG2), Hu8F4 does not lyse target cells by complement fixation. The inventors is conducting further studies to determine whether Hu8F4 mediates ADCC, direct apoptosis, or suppression of mitosis and proliferation in ongoing experiments.

Figure 17:
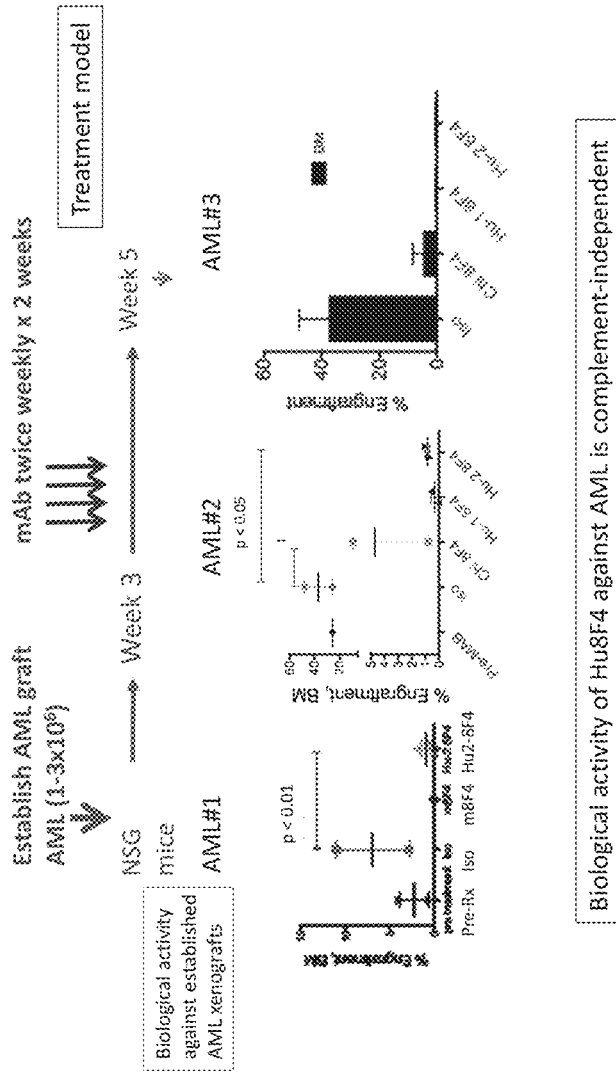
FIG. 17. Treatment with Hu8F4 eliminates established AML. Assay measures percent engraftment of AML graft given 3 weeks prior to antibody treatment.

Next, the inventors used Hu8F4 to treat established primary human AML xenografts in NSG mice. Mice were first engrafted with AML for two weeks and then treated with Hu8F4, Ch8F4, or isotype IgG1 3×/week for 2 weeks with 10 mg/kg of antibody. BM and peripheral blood chimerism were analyzed after treatment. As shown in FIG. 17, three separate experiments with 3 different AML specimens were either eliminated or their growth was significantly inhibited by Hu8F4 and Ch8F4 compared to isotype control. Therefore, these data establish that Hu8F4 is highly biologically active against primary human AML from patients with treatment-refractory relapsed disease, and that the mechanism of action of Hu8F4 is complement-independent because NSG mice lack expression of key complement proteins.

Figure 18:
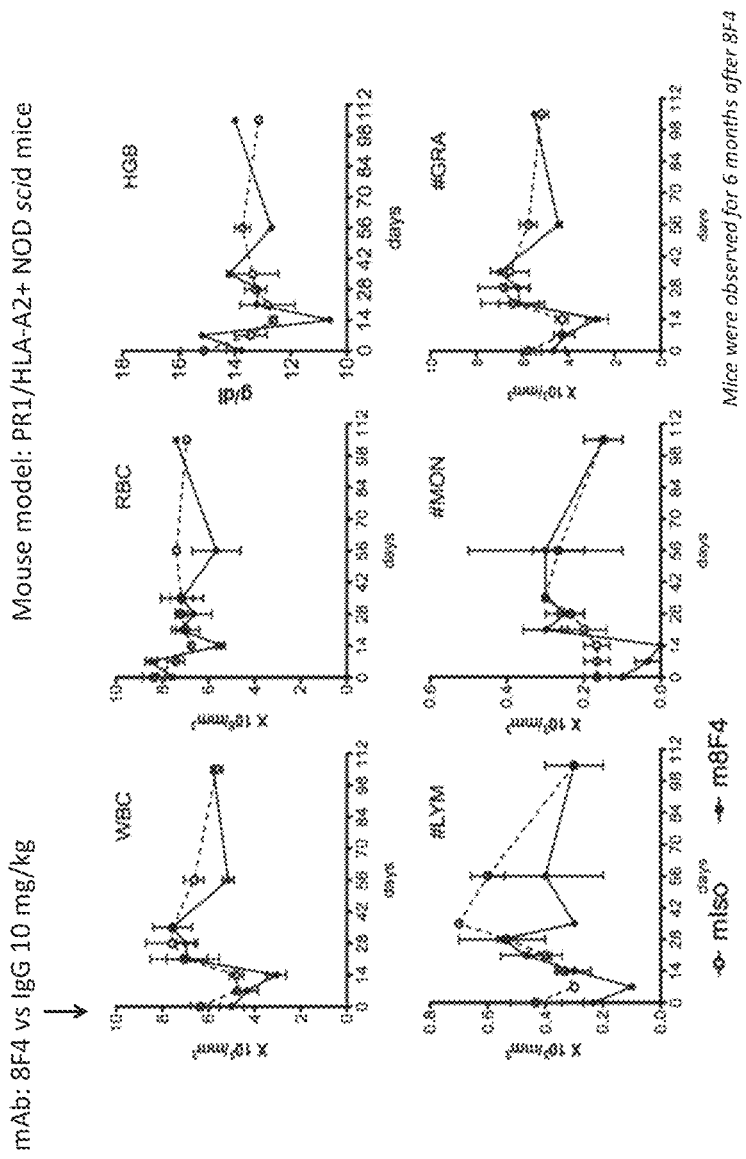
FIG. 18. 8F4 causes reversible pancytopenia: effects on normal hematopoietic progenitor cells in SCID mice.
Figure 19:
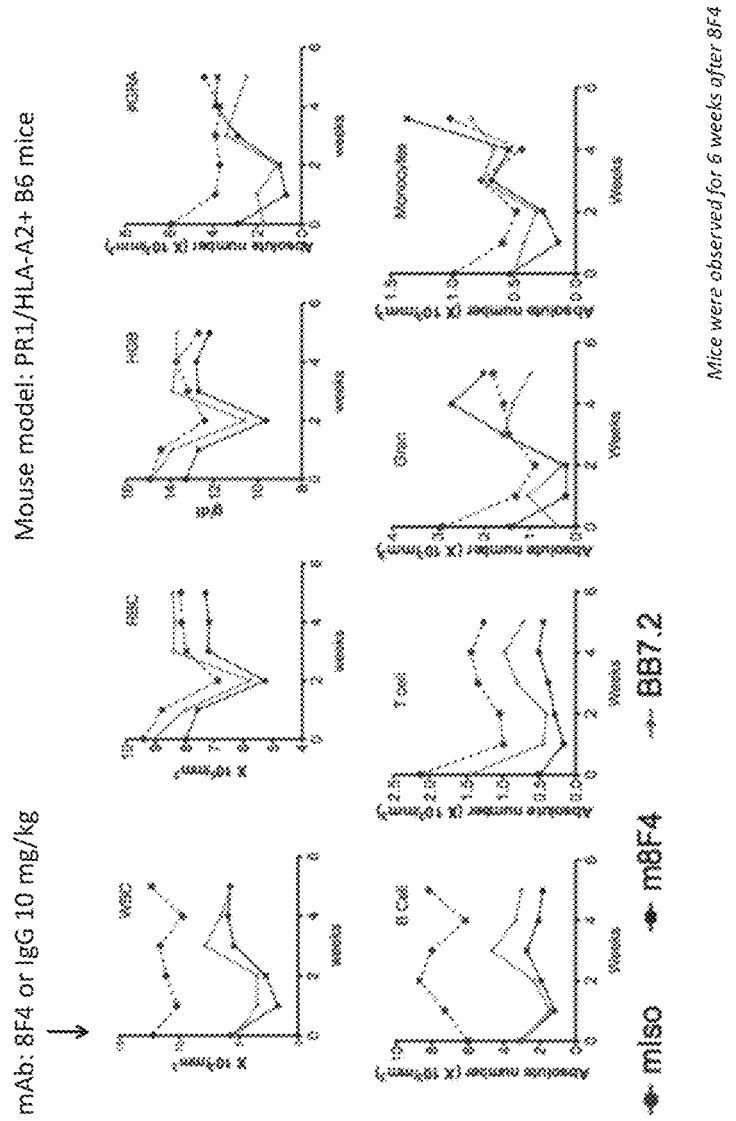
FIG. 19. 8F4 causes reversible pancytopenia: effects on normal blood cells in immune competent mice.

Biological safety data of 8F4 in HLA-A2 transgenic immune-competent (B6) and immune-deficient (NOD/scid) mice. The inventors have established three mouse models for pre-clinical studies of Hu8F4: HLA-A2 transgenic B6 immune-competent mice, HLA-A2 transgenic NOD/scid mice, and NSG (lacking the IL-2 common γ chain) mice. To determine potential toxicity, the inventors first showed that PR1 is expressed on HLA-A2 on 5 and 6% of hematopoietic stem cells and granulocytes, respectively, of the HLA-A2 transgenic animals. Next, the inventors showed that a single IV administration of high-dose 8F4 (10 mg/kg) induces transient and completely reversible cytopenia in both of the HLA-A2 transgenic mice (FIGS. 18-19). NSG mice have been engrafted with CD34-selected human cord blood to establish long-term stable human chimerism, which will be treated with single and multiple doses of Hu8F4 to determine effects of the mAb against PR1/HLA-A2+ human hematopoietic stem cells.

H8F4, an anti-PR1/HLA-A2 mAb, delays tumor growth of triple-negative breast cancer xenografts and prolongs survival. In addition to the above-noted work on leukemias, the inventors have shown that the PR1 9-mer peptide, derived from the hematopoietic-restricted serine proteases neutrophil elastase (NE) and proteinase 3 (P3), can also be cross-presented on HLA-A2 on many non-hematopoietic tumors that do not express endogenous P3 or NE, including melanoma, non-small cell lung cancer, and breast cancer (Alatrash et al., 2012). The triple-negative breast cancer cell line MB-MDA-231 (referred to as 231 cells) does not express P3 and NE but does express HLA-A2. However, these cells take up soluble P3 and NE and cross-present PR1, which subsequently makes the 231 cells susceptible to 8F4-mediated lysis. Importantly, PR1/HLA-A2 is expressed on breast cancer cells from patient biopsies (Alatrash et al., 2012), including patients with triple-negative breast cancer (TNBC). Therefore, PR1/HLA-A2 might be a target antigen on breast cancer and the inventors reasoned that 8F4 might have biological activity against HLA-A2+ breast cancer.

Figure 20A:
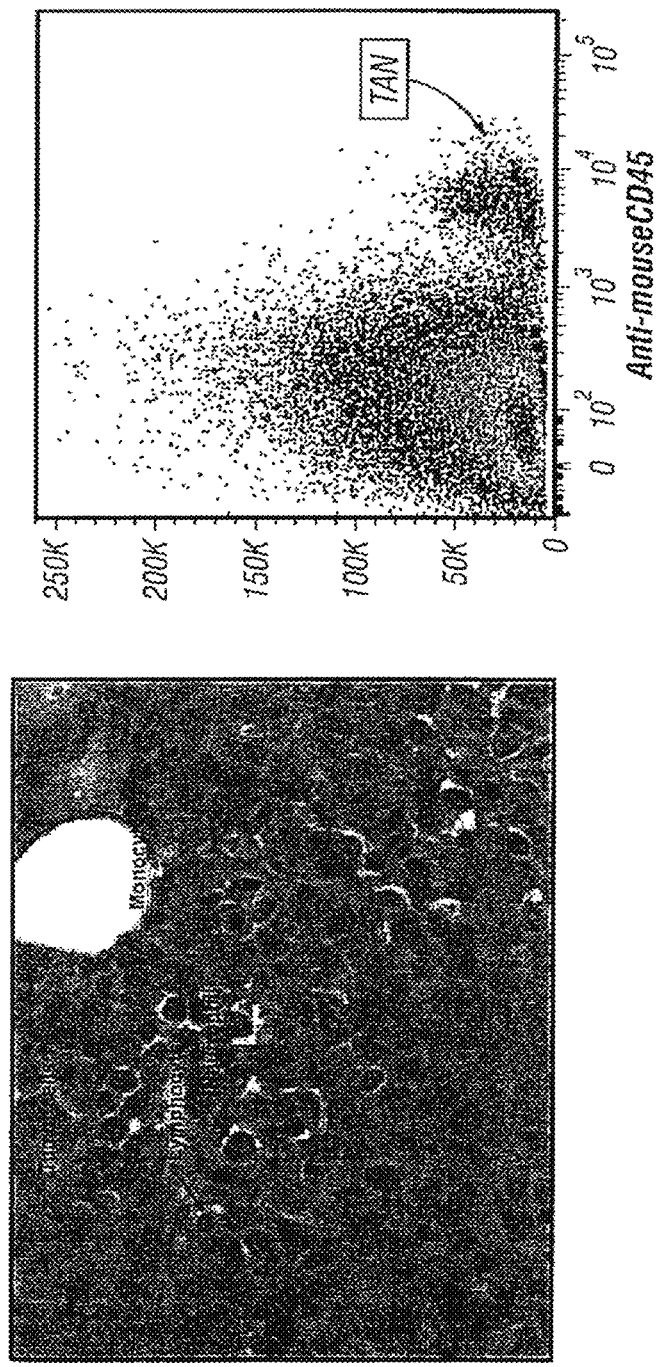
FIGS. 20A-C. 8F4 delays breast cancer tumor growth and prolongs survival.
Figure 20B:
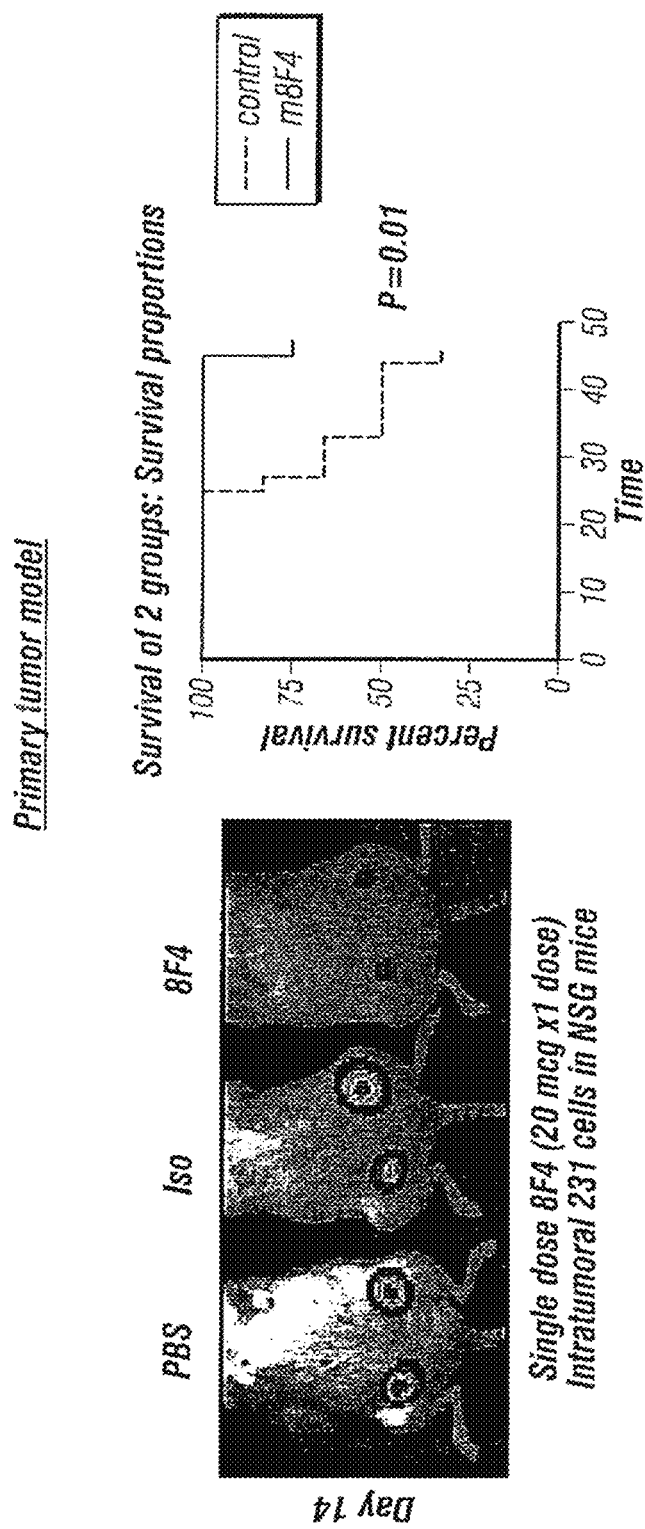

To test this hypothesis, the inventors studied the effects of h8F4 in (a) a primary tumor and (b) a metastatic tumor xenograft model in NSG mice. In the primary tumor model, 231 TNBC cells were injected into the mammary fat pad of NSG mice, followed by injection of a single dose of h8F4, isotype control antibody, or PBS. 231 cells were transfected with the ffluc gene so that tumor growth could be monitored over time with bioluminescence imaging (BLI). H&E stains of tumor site biopsies 1-2 days after implantation showed tumor infiltration by neutrophils and macrophages, which are cells that naturally express P3 and NE (FIG. 20A). As shown in FIG. 20B, tumor growth was delayed in the mice that received h8F4 compared to mice that received either isotype control or PBS. In addition, h8F4 prolonged survival compared to control mice (p<0.01).

Figure 20C:
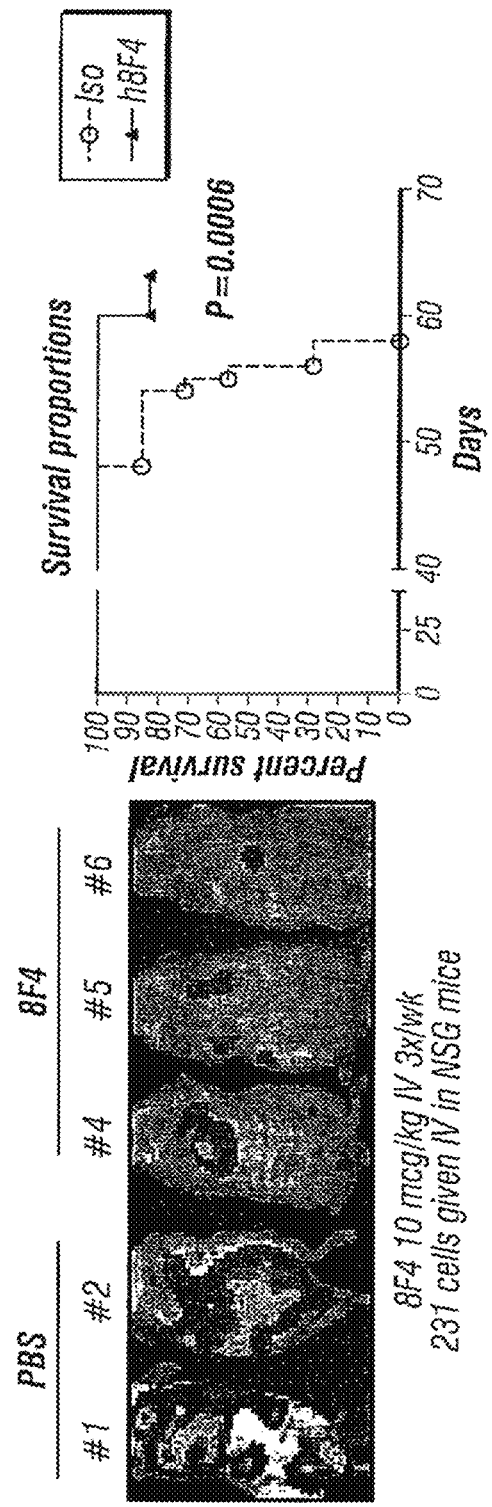

In the second model, ffluc gene modified 231 cells ($2\times10^5$) were injected into the tail vein of NSG mice and on day 7 mice received 10 mg/kg of h8F4 or isotype control antibody 3×/week. In untreated NSG mice, 231 cells injected IV rapidly metastasize to the lungs (confirmed with BLI) and subsequently to other tissues, including the spleen, GI tract, and liver. As shown in FIG. 20C, h8F4 significantly delayed metastatic tumor growth of 231 cells and significantly increased survival compared to isotype-treated mice (p=0.0006). These result suggest that P3 and NE from tumor-associated neutrophils and macrophages is taken up by 231 cells in vivo and PR1 is cross-presented on HLA-A2, which causes the growth of TNBC cells to be inhibited by h8F4 treatment. Therefore, h8F4 is biologically active against TNBC and our results strongly suggest that h8F4 mAb has potential as a therapeutic mAb to treat nonhematopoietic HLA-A2+ tumors, including breast cancer.

Example 3

Methods

Patient tissues, cells, and cell culture. Patient breast cancer frozen tissue blocks were purchased from Origene. Patient and healthy donor samples were collected after informed consent was obtained to participate in a study approved by the institutional review board at MDAnderson Cancer Center (Houston, Tex.).MDA-MB-231, MCF-7, MDAMB-453, and T47D breast cancer cell lines, and SW-620 (colorectal adenocarcinoma), OVCAR-3 (ovarian adenocarcinoma), MIA PaCa-2 (pancreatic carcinoma), Jurkat (acute T cell leukemia), T2 (B-cell/T-cell hybridoma), HL-60 (acute promyelocytic leukemia), and U-937 (histiocytic leukemia) cell lines were obtained from American Type Culture Collection. MCF-HER-18 cell line was provided by M. C. Hung (MD Anderson Cancer Center). Mel 526, Mel 624, MT 2019, and MT 2333 melanoma cell lines were provided by L. Radvanyi (MD Anderson Cancer Center). Cell lines were authenticated by DNA fingerprinting at MD Anderson Cancer Center within 6 mo of use in experiments.

Breast cancer cells were grown in DMEM with 2.5 mM 1-glutamine (HyClone) supplemented with 10% FBS (Gemini Bio-Products) and 100 U/ml penicillin/100 mg/ml streptomycin (Cellgro). G418 (Lonza) (0.5 mg/ml) was added to the MCF-7-HER18 cell cultures as a selective agent. RPMI 1640 with 25 mM HEPES plus 1-glutamine (HyClone) was used in place of DMEM for leukemia cell line cultures. All cell lines were cultured in 5% $CO_2$ at 37° C. Healthy donor and patient PBMCs and polymorphonuclear neutrophils (PMNs) were enriched using standard HISTOPAQUE® 1077 and 1119 (Sigma-Aldrich) gradient centrifugation, respectively.

RT-PCR. mRNA was extracted from cell lines and laser capture microdissection (LCM) samples using RNA STAT® 60 kit (TelTest). Synthesis of cDNA was performed using the GENE AMP® RNA kit (PerkinElmer). The following primers were used: P3, forward primer, 59-GACCCCAC-CATGGCTCAC-39 [SEQ ID NO: 52] and reverse primer, 59-ATGGGAAGGACAGACAGGAG-39 [SEQ ID NO: 53]; mammaglobin-1, forward primer, 59-AGCACTGC-TACGCAGGCTCT-39 [SEQ ID NO: 54] and reverse primer, 59-ATAAGAAAGAGAAGGTGTGG-39 [SEQ ID NO: 55]; actin, forward primer, 59-CCAGAGCAAGAGAGGCTATCC-39 [SEQ ID NO: 56] and reverse primer, 59-CTGTGGTGGTGAAGCTGTAG-39 [SEQ ID NO: 57]; and GAPDH, forward primer, 59-TA-GACGGGAAGCTCACTGGC-39 [SEQ ID NO: 58] and reverse primer, 59-AGGTCCACCACCCTGTTGCT-39 [SEQ ID NO: 59]. Following denaturation for 5 min at 95° C., samples were amplified for 35 cycles using an iCY-CLER® (Bio-Rad). Samples were run on 1.5% agarose gel. Bands were imaged using GELDOC2000® (Bio-Rad) and analyzed by QUANTITYONE® software (Bio-Rad).

Western blotting. Whole-cell lysates (WCL) were generated by suspending cell pellets in lysis buffer (10 mM/L HEPES [pH 7.9], 10 mM/L KCl, 0.1 mM/L EGTA, 0.1 mM/L EDTA, and 1 mM/L DTT) containing protease inhibitors and subsequent freeze-thaw cycles for 15 min. WCL were separated by electrophoresis on 10% SDS gels under reducing conditions, transferred onto polyvinylidene difluoride membranes, blocked with 5% milk, and stained with anti-NE (Santa Cruz Biotechnology), anti-P3 (NeoMarkers), antitubulin (Sigma-Aldrich), or anti-GAPDH (Sigma-Aldrich) Abs. Chemiluminescence was captured on Kodak film.

Ag cross-presentation. To determine protein uptake, cells were pulsed in reduced serum medium (0.5% FBS) containing 10 mg/ml P3, NE (both from Athens Research & Technology), EndoGrade OVA (Hyglos), or irradiated (7500 cGy) PMNs or PBMCs at a ratio of 1:1 (breast cancer: irradiated cell). Cells were then permeabilized (BD Biosciences) and stained with Alexa-488 or 647 directly conjugated anti-P3 (clone MCPR3-2; Thermo Scientific) or anti-NE (Santa Cruz Biotechnology) and analyzed by flow cytometry. To determine cross-presentation, cells were surface stained with fluorescently conjugated 8F4, as previously described (Sergeeva et al., 2011). Alexa-488 or 647 kits (Invitrogen) were used to directly conjugate anti-P3, anti-NE, and anti-PR1/HLA-A2 (8F4) Abs. Aqua live/dead stain (Invitrogen) was used to assess viability. For all flow cytometry experiments, light scatter was used to establish the initial gating, followed by aqua live/dead stain. To inhibit cross-presentation, cells were coincubated with the endoplasmic reticulum (ER) to Golgi antegrade inhibitor brefeldin A (Sigma-Aldrich) or the proteasome inhibitor lactacystin (Sigma-Aldrich) (Francois et al., 2009, Kovacsovics-Bankowski and Rock 1995 and Mukai et al., 2009).

Confocal imaging to show intracellular P3 localization was performed using Leica Microsystems SP2 SE confocal microscope (Leica) with 310/25 air, 363/1.4 oil objectives and analyzed using Leica LCS software (version 2.61). FITC-conjugated lysosome-associated membrane protein-2 (LAMP-2; eBioscience) was used to stain for lysosomes and late endosomes (Kuronita et al., 2002). Flow cytometry was performed using the CYTOMATION® CyAn flow cytometer (Dako). Data were analyzed using FLOWJO® software (Tree Star).

Immunohistochemistry. Cryopreserved breast and melanoma tumor tissues (Origene) were formalin fixed and then paraffin embedded for immunohistochemistry. Prior to staining, tissue sections were deparaffinized in xylene, rehydrated, and quenched for endogenous peroxidase activity. Sections were blocked with 10% normal horse serum and then incubated with primary WGM2 anti-P3 mAb clone (1:10) (Abcam) or anti-NE (Santa Cruz Biotechnology) for 30 min at room temperature. Melanoma slides were costained with anti-microphthalmia-associated transcription factor (MITF) Ab (Thermo Scientific). Slides were then washed and incubated with secondary anti-mouse IgG-biotin Ab (1:200) (Vector Laboratories), followed by avidin-biotin peroxidase (1:100) (Vector Laboratories). Chromogen 3,39-diaminobenzidine (Dako) was used for staining visualization. All slides were counterstained with hematoxylin. PMN staining of normal tonsil tissue was used as a positive control. Negative controls were stained as above after deletion of primary Abs.

Peptide-specific CTL lines. PR1-specific CTLs were expanded by stimulating PBMCs from healthy HLA-A2 donors with PR1 peptide in vitro, as previously described (Molldrem et al., 2000 and Molldrem et al., 1999). Briefly, T2 cells were washed in serum-free RPMI 1640 medium and incubated with PR1 peptide at 20 mg/ml for 90 min at 37° C. Peptide-loaded T2 cells were irradiated with 7500 cGy, washed, and cultured with freshly isolated PBMCs at a 1:1 ratio in RPMI 1640 medium supplemented with 10% human AB serum. Cultures were restimulated with peptide-pulsed T2 cells on days 7, 14, and 21, and, on the following day, 20 IU/ml human rIL-2 (BioSource International) was added.

Cell-mediated cytotoxicity assay. A standard cytotoxicity assay was used to determine specific lysis, as described previously (Molldrem et al., 1996 and Molldrem et al., 1997). Briefly, 1,000 target cells in 10 ml (1.0 3 $10^5$ cells/ml) were stained with calcein-AM (Invitrogen) for 90 min at 37° C., washed three times with RPMI 1640, and then coincubated with 10 ml peptide-specific CTLs at varying E:T ratios. After a 4-h incubation period at 37° C. in 5% $CO_2$, 5 ml trypan blue was added to each well and fluorescence was measured using an automated CYTOFLUOR® II plate reader (PerSeptive Biosystems). Percent specific cytotoxicity was calculated as follows: ([fluorescence$_{target+effector}$ fluorescence$_{media}$]/[fluorescence$_{target\ alone}$ fluoresecence$_{media}$])×100.

Complement-mediated cytotoxicity assay. To determine whether cross-presentation increases breast cancer susceptibility to 8F4, we performed complement-mediated cytotoxicity assay, as previously described (Sergeeva et al., 2011 and Prang et al., 2005). MDA-MB-231 cells were cultured in NE (10 mg/ml) or P3 (10 mg/ml) containing media for 24 h. Cells were incubated with calcein-AM (Invitrogen), washed three times, and resuspended in serum-free RPMI 1640. One million cells were mixed with increasing doses of 8F4 Ab (0.624, 1.25, 2.5, 5, and 10 mg/ml) or isotype Ab (negative control) at a final concentration of 10 mg/ml and incubated for 10 min at 37° C. Standard rabbit complement (5 ml; Cedarlane Laboratories) was then added, and cells were incubated for 60 min at 37° C. Supernatant from BB7.2 hybridoma (source for anti-HLA-A2) and digitonin (Promega) were used as positive controls. Fluorescence was measured, and specific killing was calculated, as described above.

LCM and RNA extraction from breast tumor tissue. LCM was performed to isolate breast cancer cells from breast tumor biopsy tissue with an Arcturus PixCell laser capture microscope with an IR diode laser (Life Technologies, Applied Biosystems). Tissue was sectioned (5 mm thickness), placed on noncharged glass slides, and fixed in 75% ethanol and diethyl pyrocarbonate water. Hematoxylin was used to stain nuclei after tissue hydration. Samples were stored in xylene after graded alcohol dehydration until ready for LCM. The areas used for microdissection were identified using H&E staining. Tissue was pulsed with a laser beam with power adjusted between 30 and 70 mW to maintain a 10 mm diameter. Approximately 5,000 breast cancer cells were captured in ARCTURUS CAPSURE® HS LCM caps (Life Technologies, Applied Biosystems). Total RNA was extracted and purified using the ARCTURUS PICOPURE® RNA Isolation Kit (Life Technologies, Applied Biosystems). RNA integrity and quantity were determined with a NANO DROP® ND-1,000 Spectrophotometer (Thermo Scientific). Arcturus RiboAmp RNA Amplification Kit was used to amplify RNA using two rounds of T7-based amplification. This yielded 2.5 mg amplified RNA. cDNA was synthesized from 1 mg amplified RNA using the Roche TRANSCRIPTOR® First Strand cDNA Synthesis Kit (Roche Applied Science), per manufacturer instructions.

Staining for PR1-CTLs in breast cancer patients. PBMC from patients were stained with the following fluorescent Abs: CD8 allophycocyanin-H7 (BD Biosciences), CD3 PE Cy7 (BD Biosciences), CD4 pacific orange (Invitrogen), PE-conjugated PR1/HLA-A2-dextramer (Immudex), and the following pacific blue-conjugated lineage Abs: CD14 (BD Biosciences), CD16 (BD Biosciences), and CD19 (BioLegend). Aqua live/dead stain (Invitrogen) was used to exclude dead cells. Samples were fixed with 4% paraformaldehyde. Data were acquired on CANTO® flow cytometer (BD Biosciences) and analyzed using FLOWJO® software (Tree Star). The frequency of PR1-CTLs was determined as the percentage of live cells that were lineage$^-$, CD4$^-$, CD3+, CD8+, and PR1-dextramer$^+$.

Confocal imaging of patient tissues. Cryopreserved tissue sections were fixed with cold acetone. Breast cancer tissues were stained with the breast cancer marker Alexa-488-conjugated mouse anti-cytokeratin-7 (CK7) Ab (Abcam) and Alexa-647-conjugated 8F4 Ab (Sergeeva et al., 2011). To confirm that the PR1/HLA-A2 expression is by breast cancer cells and not by the infiltrating leukocytes, consecutive breast cancer tissue sections were also stained with Alexa-647-conjugated mouse anti-CD45 Ab (Invitrogen) as a leukocyte marker. Human tonsil tissue sections (Origene) were used as positive staining control for CD45. For melanoma, tissue sections were fixed with cold acetone, permeabilized with 0.5% Triton X-100 (Sigma-Aldrich) for 15 min, and blocked with 5% normal goat serum (Jackson ImmunoResearch Laboratories). Sections were then incubated with the melanoma marker mouse anti-MITF (Thermo Scientific) for 1 h, washed with PBS, and then incubated with Alexa-488-conjugated goat anti-mouse IgG (Jackson ImmunoResearch Laboratories). Slides were then washed, blocked with 5% normal mouse serum (Jackson ImmunoResearch Laboratories), and incubated with Alexa-647-conjugated 8F4 Ab. ProLong Gold antifade reagent with DAPI (Invitrogen) was added. Confocal imaging was performed using Leica Microsystems SP2 SE confocal microscope with 310/25 air, 363/1.4 oil objectives. Leica LCS software (version 2.61) was used for image analysis.

Example 4

Results

Solid tumors take up NE and P3. To determine whether uptake of NE and P3 is a ubiquitous phenomenon, the inventors cocultured multiple solid tumor cell lines with 10 mg/ml NE or P3 and then used flow cytometry to assess for intracellular uptake. The inventors showed that not all tumor types take up NE and P3, and, furthermore, the degree of uptake varies among different tumor types (FIG. 21). In addition, NE uptake appears to plateau over time and is much lower than P3 uptake, indicating different uptake mechanisms and suggesting a receptor-mediated process that may be involved in NE uptake.

P3 is absent in breast cancer. Because the inventors have previously shown that NE is absent in breast cancer and is taken up by breast cancer cells (Mittendorf et al., 2012) and to differentiate P3 uptake from endogenous expression, we analyzed breast cancer cell lines and primary tumor tissues for P3 expression at the mRNA and protein levels. PCR shows that the breast cancer cell lines MDA-MB-231, MCF-7, MCF-7-HER18 (HER18), and MDAMB-453 all lack P3 mRNA (FIG. 22A). Similarly, breast cancer cells extracted from three different breast tumors (FIG. 22B, Table 6) also lack P3 mRNA. Immunoblots of WCL from cell lines confirmed the absence of P3 protein in breast cancer cells (FIG. 22C). Immunohistochemistry staining of primary breast cancer detected P3 in breast cancer tissue, but the P3 was limited to the inflammatory component within the breast tumor, and not in the breast tumor cells (FIG. 22D). These data are consistent with previous reports showing P3 in breast cancer (Desmedt et al., 2006), although our data suggest that the source of P3 is inflammatory cells within the tumor, and not the breast cancer cells.

TABLE 6

Pathologic characteristics of breast and melanoma tumor tissues used for LCM and confocalmicroscopy

| Patient | Histology | ER/PR/HER2 Status | TNM Staging | HLA-A2 Status |
|---|---|---|---|---|
| Breast 1 | IDC | ER2−/PR2−/HER22− | T1cNXMX | Positive |
| Breast 2 | IDC | ER2−/PR2−/HER2+ | T2N1bMX | N/D |
| Breast 3 | IDC/ILC | ER+/HER2+ | T2N1aMX | Negative |
| Breast 4 | IDC | ER2−/HER22− | T3N0MX | Positive |
| Melanoma 1 | Nodular | N/A | T3N2M1c | Positive |
| Melanoma 2 | N/D | N/A | T3N2M1b | Negative |

ER, Estrogen receptor; HER2, HER2/neu; IDC, invasive ductal carcinoma; ILC, invasive lobular carcinoma; N/D, not determined; PR, progesterone receptor; TNM, tumor/node/metastasis classification of malignant tumors.

P3 is taken up by breast cancer cells. Because we showed that P3 is not expressed endogenously by breast cancer cells, the inventors hypothesized that P3 may be taken up by breast cancer cells, as they have previously shown for NE (Mittendorf et al., 2012). The HLA-A2-positive cell lines MDA-MB-231, MCF-7, and HER18 were cocultured with 10 mg P3 at 1, 4, and 24 h and then analyzed using flow cytometry for intracellular uptake of P3 (FIG. 23A). The inventors detected a time-dependent increase in P3 uptake in all three cell lines. They also demonstrated a dose-dependent uptake of P3 that does not appear to plateau, suggesting a nonreceptor-mediated process for P3 uptake (FIG. 23B). To further characterize P3 uptake as it relates to Ag cross-presentation, which occurs in distinct cellular compartments (Cresswell et al., 2005), the inventors performed laser confocal microscopy and showed that, following uptake, P3 localizes within lysosomes, as shown by P3 costaining with LAMP-2 (FIG. 23C). Uptake into lysosomal compartments occurred at early time points (1-4 h) and may be the initial step in Ag degradation as it is being processed for cross-presentation on HLA class-I molecules (Basha et al., 2008).

Because different cellular pathways are involved in uptake and processing of soluble and cell-associated proteins, which can determine whether they are cross-presented (Burgdorf et al., 2006), and because neutrophils were reported in tumor tissues including breast cancer (Queen et al., 2005 and Jensen et al., 2009), the inventors evaluated whether there was difference in the uptake of soluble and cell-associated P3 by breast cancer cells. To examine this, MDA-MB-231 cells were cocultured for 4 h with soluble P3 (10 mg/ml) or with irradiated PMNs or PBMCs at a 1:1 ratio (FIG. 24A; data not shown). Data demonstrated that breast cancer cells can take up both soluble P3 as well as cell-associated P3. In fact, uptake from cell-associated P3 appears to be more efficient compared with uptake of soluble protein (median fluorescence intensity [MFI]=12,292 versus 1,356; p, 0.05), which may be due to the association of P3 with other proteins that could facilitate uptake.

P3 and NE are cross-presented by breast cancer cells. Because the inventors have shown that NE is also taken up by breast cancer (Mittendorf et al., 2012) and because PR1 is derived from both of the neutrophil azurophil granule proteases NE and P3, they investigated whether NE and P3 are cross-presented by breast cancer cells following uptake. The HLA-A2$_+$ MDA-MB-231 cells were cocultured with soluble P3 or NE at increasing time points and subsequently analyzed for PR1/HLA-A2 expression using the mouse anti-PR1/HLA-A2 Ab 8F4 (Sergeeva et al., 2011). These data show that breast cancer cells can cross-present PR1 from both NE and P3. Significant PR1 cross-presentation was primarily seen at 24 h (FIG. 24B) with a 2.5- and 3.0-fold increase in PR1/HLA-A2 on breast cancer cell surface following culture with NE and P3, respectively, compared with unpulsed cells. There was no significant increase in HLA-A2 expression on the cell surface (data not shown).

Furthermore, to investigate the intracellular mechanisms that are involved in NE and P3 cross-presentation, the inventors studied whether the proteasome and the ER/Golgi are involved in NE and P3 cross presentation, as was previously shown for other Ags (Francois et al., 2009, Kovacsovics-Bankowski et al., 1995 and Mukai et al., 2009). Our data show that the ER/Golgi and proteasome are both involved in NE and P3 cross-presentation, because incubation of cells with brefeldin A, which inhibits ER to Golgi antegrade transport, and with lactacystin, a proteasome inhibitor, both decreased PR1/HLA-A2 expression by MDA-MB-231 breast cancer cells after coculturing with NE or P3 (FIGS. 24C, 24D). This is similar to the inventors' previous results demonstrating proteasome and ER/Golgi involvement in NE and P3 cross-presentation by APCs (Alatrash et al., 2012).

PR1 cross-presentation renders breast cancer susceptible to PR1-targeting therapies. Because PR1 has been effectively targeted in leukemia using a PR1 peptide vaccine (Rezvani et al., 2008), PR1-CTLs (Rezvani et al., 2007 and Ma et al., 2010), and anti-PR1/HLA-A2 Ab (8F4) (Sergeeva et al., 2011), the inventors investigated whether PR1/HLA-A2 expression on breast cancer cells following cross-presentation would render these cells susceptible to killing by PR1-CTLs and 8F4 Ab. The HLA-A2+ MDA-MB-231 cells were cultured in media containing 10 mg/ml NE or P3 for 24 h and then incubated with healthy donor-expanded PR1-CTLs for 4 h in a standard calcein-AM cytotoxicity assay (Molldrem et al., 1996; Jiang et al., 1996) (FIG. 24E). The data demonstrate that cross-presentation of NE and P3 increased the susceptibility of MDA-MB-231 cells to killing by PR1-CTLs after NE or P3 pulsing, in comparison with unpulsed MDA-MB-231 cells. Similarly, using 8F4 Ab in a complement-dependent cytotoxicity assay (FIG. 24F) (Sergeeva et al., 2011), the inventors observed a dose-dependent killing of MDA-MB-231 cells following NE or P3 cross-presentation in comparison with unpulsed cells. The greatest killing was noted at the highest dose of 8F4 Ab (10 mg/ml).

PR1/HLA-A2 and PR1-CTL are detected in patients with breast cancer. Because the inventors showed that cultured breast cancer cell lines and tumor tissues lack endogenous NE and P3, and because they observed in vitro evidence of NE and P3 cross-presentation by breast cancer cells and subsequent susceptibility to PR1-targeting therapies, the inventors investigated whether PR1 could be detected in primary beast cancer patient tissues and whether PR1-CTLs could be detected in peripheral blood from patients with breast cancer. Laser confocal microscopy of two HLA-A2-positive breast cancer tissues demonstrated 8F4 in both tumor tissues (FIG. 25A). The 8F4 staining was absent in HLA-A2-negative tissue (data not shown). Moreover, to verify that the expression of PR1/HLA-A2 is by breast cancer cells and not by infiltrating leukocytes, the inventors stained consecutive breast cancer tissue sections with the leukocyte marker CD45. The inventors showed the absence of CD45 staining in the areas of the breast cancer tissue that costained with 8F4 and CK7, further confirming that the PR1/HLA-A2 expression was by breast cancer cells, not by adjacent inflammatory cells (FIG. 25B).

To determine whether PR1-CTL could be detected in breast cancer patients, we used PR1/HLA-A2 dextramer staining of 11 peripheral blood samples from early-stage breast cancer patients (FIG. 25C). The median frequency of PR1-CTLs in these HLA-A2$_+$ patients was 0.05% of CD8$_+$ T cells (range, 0.02-0.2%), slightly higher than the frequency of PR1-CTLs in healthy donors (1/15,000 to 1/350,000 CD8$_+$ cells) (Molldrem et al., 1997). Taken together, these in vivo data suggest that the serine proteases NE and P3 present in the tumor microenvironment can be taken up and cross-presented by breast cancer cells, which may contribute to an adaptive immune response against the NE- and P3-derived epitope PR1.

PR1/HLA-A2 and PR1-CTL in melanoma patients. Because melanoma tissues were also shown to have inflammatory cells that may be a source for NE and P3 (Jensen et al., 2012), and because melanoma is known to be susceptible to immunotherapy (Dudley et al., 2002 and Schwartzentruber et al., 2011), the inventors next investigated whether cross-presentation of NE and P3 could also be detected in melanoma. To determine whether PR1-CTL are also detected in melanoma, the inventors stained PBMC from melanoma patients with PR1/HLA-A2 dextramer and detected PR1-CTLs in all seven patients at a median frequency of 0.014% of CD8+ T cells (range, 0.0053-0.019%) (FIG. 25C), similar to what was seen in blood from normal donors. The inventors also detected PR1/HLA-A2 expression in one HLA-A2$_+$ (melanoma 1), but not HLA-A2$_2$ (melanoma 2) melanoma tissue (FIG. 25D).

Cross-presentation of NE and P3 by melanoma increases susceptibility to PR1-CTL. To determine whether melanoma expresses NE and P3, the inventors stained melanoma tissue obtained from patients for NE and P3 and showed the absence of NE and P3 (FIGS. 26A, 26B). The inventors also analyzed NE and P3 expression in four melanoma cell lines, MEL526, MEL624, MT2019, and MT2333. Western blot analysis shows absence of NE and P3 in melanoma cell lines (FIG. 26C). Similar to breast cancer, the inventors demonstrate uptake and cross-presentation of NE and P3 by the HLA-A2+ Mel 526 cell line (FIGS. 26D, 26E). Because 8F4 Ab binds to the HLA-A2 molecule (Sergeeva et al., 2011 and Porgador et al., 1997), which composes a significant portion of the conformational PR1/HLA-A2 epitope, Mel 526 cells do show staining with 8F4 prior to coculture with NE or P3 (data not shown). However, staining with 8F4 increases after coculture with NE or P3, without an increase in HLA-A2 surface staining (data not shown), indicating an increase in PR1/HLA-A2 expression on the cell surface. Furthermore, cross-presentation of NE and P3 increased the susceptibility of the HLA-A2+ Mel 526 cell line to killing by PR1-CTL, with the highest killing noted at the highest E:T ratio (FIG. 26F).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 4,196,265
U.S. Pat. No. 4,472,509
U.S. Pat. No. 4,554,101
U.S. Pat. No. 4,680,338
U.S. Pat. No. 4,684,611
U.S. Pat. No. 4,797,368
U.S. Pat. No. 4,843,092
U.S. Pat. No. 4,879,236
U.S. Pat. No. 4,938,948
U.S. Pat. No. 4,952,500
U.S. Pat. No. 5,021,236
U.S. Pat. No. 5,302,523
U.S. Pat. No. 5,322,783
U.S. Pat. No. 5,384,253
U.S. Pat. No. 5,399,363
U.S. Pat. No. 5,443,826
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,563,250
U.S. Pat. No. 5,580,859
U.S. Pat. No. 5,589,466
U.S. Pat. No. 5,599,795
U.S. Pat. No. 5,610,042
U.S. Pat. No. 5,641,515
U.S. Pat. No. 5,656,610
U.S. Pat. No. 5,702,932
U.S. Pat. No. 5,736,524
U.S. Pat. No. 5,739,169
U.S. Pat. No. 5,780,448
U.S. Pat. No. 5,789,215
U.S. Pat. No. 5,801,005
U.S. Pat. No. 5,824,311
U.S. Pat. No. 5,830,880
U.S. Pat. No. 5,846,233
U.S. Pat. No. 5,846,945
U.S. Pat. No. 5,856,456
U.S. Pat. No. 5,871,986
U.S. Pat. No. 5,880,270
U.S. Pat. No. 5,945,100
U.S. Pat. No. 5,981,274
U.S. Pat. No. 5,994,136

U.S. Pat. No. 5,994,624
U.S. Pat. No. 6,013,516
Alatrash et al., *J. Immunol.*, 35: 309-320, 2012
Antin, *Blood*, 82:2273-2277, 1993.
Arend et al., *Annu. Rev. Immunol.*, 16:27-55, 1998.
Arend, Semin. *Arthritis Rheum.*, 30(5):1-6, 2001.
Austin-Ward and Villaseca, *Rev. Med. Chil.*, 126(7):838-45, 1998.
Baichwal and Sugden, In: *Gene Transfer*, Kucherlapati (Ed.), NY, Plenum Press, 117-148, 1986.
Bajorin et al., *J. Clin. Oncol.*, 6(5):786-92, 1988.
Bakhshi et al., *Cell*, 41(3):899-906, 1985.
Basha et al., *Plos One*, 3:e3247, 2008.
Beidler et al., *J. Immunol.*, 141(11):4053-4060, 1988.
Besnard et al., *Gut.*, 43(5):634-638, 1998.
Blomer et al., *J. Virol.*, 71(9):6641-6649, 1997.
Brouwer et al., *Clin. Exp. Immunol.*, 98:448-453, 1994.
Brynskov et al., *N. Engl. J. Med.*, 321(13):845-850, 1989.
Bukowski et al., *Clin. Cancer Res.*, 4(10):2337-47, 1998.
Burchert et al., *Blood*, 02:659, 2002.
Burgdorf et al., *J. Immunol.*, 176:6770-6776, 2006.
Burger and Dayer, *Neurology*, 45(6S-6):S39-43, 1995.
Capaldi et al., *Biochem. Biophys. Res. Comm.*, 74(2):425-433, 1977.
Chen and Okayama, *Mol. Cell Biol.*, 7(8):2745-2752, 1987.
Christodoulides et al., *Microbiology*, 144(Pt 11):3027-37, 1998.
Cleary and Sklar, *Proc. Natl. Acad. Sci. USA*, (21):7439-7443, 1985.
Cleary et al., *J. Exp. Med.*, 164(1):315-320, 1986.
Cotten et al., *Proc. Natl. Acad. Sci. USA*, 89(13):6094-6098, 1992.
Coupar et al., *Gene*, 68:1-10, 1988.
Cresswell et al., *Immunol. Rev.*, 207:145-157, 2005.
Curiel, *Nat. Immun.*, 13(2-3):141-164, 1994.
Davidson et al., *J. Immunother* 21(5):389-98, 1998.
Desmedt et al., *Int. J. Cancer*, 119: 2539-2545, 2006.
Dillman, *Cancer. Biother. Radiopharm.*, 14(1):5-10, 1999.
Dinarello, *Int. Rev. Immunol.*, 16:457-499, 1998.
Dionne et al., *Clin. Exp. Imunol.*, 112(3):435-442, 1998.
Dudley et al., *Science*, 298: 850-854, 2002.
Eastgate et al., *Lancet*, 2:706-709, 1988.
EP Application 125,023
EP Application 171,496
EP Application 173,494
EP Application 184,187
Fechheimer et al., *Proc. Natl. Acad. Sci. USA*, 84:8463-8467, 1987.
Fellerman et al., *Am. J. Gastroenterol.*, 93(10):1860-1866, 1998.
Firestein et al., *Arthritis Rheum.*, 37:644-652, 1994.
Fraley et al., *Proc. Natl. Acad. Sci. USA*, 76:3348-3352, 1979.
Francois et al., *Blood*, 114: 2632-2638, 2009.
Franssen et al., *Lancet.*, 347:116, 1996.
Friedmann, *Science*, 244:1275-1281, 1989.
Fujikawa et al., *Ann. Rheum. Dis.*, 54:318-320, 1995.
Funakoshi et al., *Digestion*, 59(1):73-78, 1998.
Giralt and Kolb, *Curr. Opin. Oncol.*, 8:96-102, 1996.
Gopal, *Mol. Cell Biol.*, 5:1188-1190, 1985.
Graham and Van Der Eb, *Virology*, 52:456-467, 1973.
Grunhaus and Horwitz, *Seminar in Virology*, 3:237-252, 1992.
Hanibuchi et al., *Int. J. Cancer*, 78(4):480-485, 1998.
Hannum et al., *Nature*, 343:336-340, 1990.
Harland and Weintraub, *J. Cell Biol.*, 101:1094-1099, 1985.
Hellstrand et al., *Acta Oncol.*, 37(4):347-353, 1998.
Hoffenberg et al., *J. Pediatr* 134(4):447-452, 1999.
Hollander et al., *Ann. Intern. Med.*, 105:883-885, 1986.
Hollander, *Scand. J. Gastroenterol.*, 27:721-726, 1992.
Horwich et al. *J. Virol.*, 64:642-650, 1990.
Hui and Hashimoto, *Infect. Immun.*, 66(11):5329-36, 1998.
Irie et al., *Lancet.*, 1(8641):786-787, 1989.
Jarvis, Curr. *Opin. Rheumatol.*, 10(5):459-467, 1998.
Jarvis, *Pediatr. Ann.*, 31(7):437-446, 2002.
Jensen et al., *J. Clin. Oncol.*, 27:4709-4717, 2009.
Jensen et al., *Cancer*, 118: 2476-2485, 2012.
Jiang et al., *Br. J. Haematol.*, 93:606-612, 1996.
Johnson et al., In: *Biotechnology And Pharmacy*, Pezzuto et al. (Eds.), Chapman and Hall, N.Y., 1993.
Jones et al., *Nature*, 321:522-525, 1986.
Jonsson et al., *Br. J. Rheumatol.*, 32(7):578-581 1993.
Jonsson et al., *Oral Dis.*, 8(3):130-140, 2002.
Jonsson et al., *Trends Immunol.*, 22(12):653-654, 2001.
Kaeppler et al., *PlanT-cell Reports*, 9:415-418, 1990.
Kahle et al., *Ann. Rheum. Dis.*, 51:731-734, 1992.
Kaneda et al., *Science*, 243:375-378, 1989.
Kato et al, *J. Biol. Chem.*, 266:3361-3364, 1991.
Kelleher and Vos, *Biotechniques*, 17(6):1110-7, 1994.
Kerr et al., *Br. J. Cancer*, 26(4):239-257, 1972.
Kolb and Holler, *Curr. Opin. Oncol.*, 9:139-145, 1997.
Kolb et al., *Blood*, 86:2041-2050, 1995.
Kolb et al., *Bone Marrow Transplant*, 17:449-452, 1996.
Kotzin, *Cell*, 85:303-306, 1996.
Kovacsovics-Bankowski and Rock, *Science*, 267: 243-246, 1995.
Kuboyama, *Kurume Med. J.*, 45(1):33-37, 1998.
Kuronita, *J. Cell Sci.*, 115:4117-4131, 2002.
Kyte and Doolittle, *J. Mol. Biol.*, 57(1):105-32, 1982.
Laughlin et al., *J. Virol.*, 60(2):515-524, 1986.
Lebkowski et al., *Mol. Cell. Biol.*, 8(10):3988-3996, 1988.
Leiper et al., *Baillieres Clin. Gastroenterol.*, 12(1):179-199, 1998.
Lipsky, In: *Harrison's principles of internal medicine*, Fauci et al. (Eds.), 14$^{th}$ Ed., N.Y., McGraw-Hill, 1880-1888, 1998.
Lugering et al., *Ital. J. Gastroenterol. Hepatol.*, 30(3):338-344, 1998.
Makowiec et al., *Z. Gastroenterol.*, 36(8):619-624, 1998.
Mann et al., *Cell*, 33:153-159, 1983.
McAlindon et al., *Gut*, 42(2):214-219, 1998.
McLaughlin et al., *J. Virol.*, 62(6):1963-1973, 1988.
Miller et al., *Am. J. Clin. Oncol.*, 15(3):216-221, 1992.
Mittendorf et al., *Cancer Res.*, 72:3153-3162, 2012.
Molldrem et al., *Blood*, 88:2450-2457, 1996.
Molldrem et al., *Blood*, 90:2529-2534, 1997.
Molldrem et al., *Cancer Res.*, 59:2675-2681, 1999.
Molldrem et al., *Nat. Med.*, 6:1018-1023, 2000.
Molldrem et al., *J. Clin. Invest.*, 111:639-647, 2003.
Morrison, *Science*, 229(4719):1202-1207, 1985.
Mukai, et al., *J. Immunol.*, 183:6561-6568, 2009.
Murch, *Nutrition*, 14:780-783, 1998.
Muzyczka, *Curr. Topics Microbiol. Immunol.*, 158:97-129, 1992.
Naldini et al., *Science*, 272(5259):263-267, 1996.
Nicolau and Sene, *Biochim. Biophys. Acta*, 721:185-190, 1982.
Nicolau et al., *Methods Enzymol.*, 149:157-176, 1987.
Ohnishi et al., *Int. Immunol.*, 6:817-830, 1994.
Omirulleh et al., *Plant Mol. Biol.*, 21(3):415-28, 1993.
Paskind et al., *Virology*, 67:242-248, 1975.
Paul, Immunogenetics, 37(6):442-448, 1993.
Pietras et al., *Oncogene*, 17(17):2235-49, 1998.
Porgador et al., *Immunity* 6: 715-726, 1997.

Potrykus et al., *Mol. Gen. Genet.*, 199:183-188, 1985.
Prang et al., *Br. J Cancer,* 92:342-349, 2005.
Prieur et al., *Lancet.,* 2:1240-1242, 1987.
Qin et al., *Proc. Natl. Acad. Sci. USA,* 95(24):14411-14416, 1998.
Queen et al., *Cancer Res.,* 65:8896-8904, 2005.
Reimund et al., *Eur. J Clin. Invest.,* 28(2):145-150, 1998.
Remington's Pharmaceutical Sciences, 15$^{th}$ ed., pages 1035-1038 and 1570-1580, Mack Publishing Company, Easton, Pa., 1980.
Rezvani et al., *Cytotherapy* 9: 245-251, 2007.
Rezvani et al., *Blood,* 111:236-242, 2008.
Ridgeway, In: Vectors: *A survey of molecular cloning vectors and their uses,* Rodriguez and Denhardt (Eds.), Stoneham:Butterworth, 467-492, 1988.
Rippe et al., *Mol. Cell Biol.,* 10:689-695, 1990.
Rogler and Andus, *World J. Surg.,* 22(4):382-389, 1998.
Rooney et al., *Rheumatol. Int.,* 10:217-219, 1990.
Rosenberg et al., *Ann. Surg.* 210(4):474-548, 1989.
Rosenberg et al., *N. Engl. J. Med.,* 319:1676, 1988.
Roux et al., *Proc. Natl. Acad. Sci. USA,* 86:9079-9083, 1989.
Ruemmele et al., *Gastroenterol.,* 115(4):822-829, 1998.
Saiki et al., *Scand. J. Gastroenterol.,* 33(6):616-622, 1998.
Salomonsson et al., *Scand. J. Immunol.,* 55(4):336-342, 2002.
Sartor, *Am. J. Gastroenterol.,* 92(12):5S-11S, 1997.
Savage et al., *Immunity,* 10:485-492, 1999.
Scheibenbogen et al., *Blood,* 100:2132-2137, 2002.
Schreiber, *Neth. J. Med.,* 53(6):524-31, 1998.
Schwartzentruber, et al., *N. Engl. J. Med.,* 364: 2119-2127, 2011.
Sergeeva, et al., *Blood,* 117: 4262-4272, 2011.
Shaw et al., *J. Natl. Cancer Inst.,* 80(19):1553-1559, 1988.
Soderholm et al., *Gastroenterol.,* 117:65-72, 1999.
Stack et al., *Lancet,* 349(9051):521-524, 1997.
Stites, *J. Mol. Biol.,* 235(1):27-32, 1994.
Sun et al., *J. Steroid Biochem.,* 26(1):83-92, 1987.
Targan et al., *N. Engl. J. Med.,* 337(15):1029-1035, 1997.
Temin, In: *Gene Transfer,* Kucherlapati (Ed.), NY, Plenum Press, 149-188, 1986.
Tratschin et al., *Mol. Cell. Biol.,* 4:2072-2081, 1984.
Tsujimoto and Croce, *Proc. Natl. Acad. Sci. USA,* 83(14): 5214-5218, 1986.
Tsujimoto et al., *Science,* 228(4706):1440-1443, 1985.
van den Berg, *Semin. Arthritis Rheum.,* 30(55-2):7-16, 2001.
van Dullemen et al., *Gastroenterol.,* 109(1):129-135, 1995.
VandenDriessche et al., *Blood,* 100(3) 813-822, 2002.
Wada et al., *Nucleic Acids Res.* 18:2367-2411, 1990.
Warrington et al., *Arthritis and Rheumatism,* 44:13-20, 2001.
Wong et al., *Gene,* 10:87-94, 1980.
Wood et al., *J. Clin. Lab. Immunol.,* 17(4):167-171, 1985.
Xanthou et al., *Arthritis Rheum.,* 44(2):408-418, 2001.
Zufferey et al., *Nat. Biotechnol.,* 15(9):871-875, 1997.

The invention claimed is:

1. A method of treating a subject with a myeloid leukemia comprising administering to said subject an antibody, wherein the antibody binds to VLQELNVTV (SEQ ID NO:45) when bound by an HLA-A2 receptor, said antibody comprises a heavy chain variable region comprising CDRs consisting of amino acid sequences SEQ ID NOS: 3, 60 and 5 respectively, and a light chain variable region comprising CDRs consisting of amino acid sequences SEQ ID NOS: 8, 9 and 10 respectively, wherein said myeloid leukemia expresses a complex of HLA-A2 and peptide VLQELNVTV, (SEQ ID NO: 45), wherein said antibody comprises a constant region capable of complement-dependent cytotoxicity or antibody-dependent cellular cytotoxicity.

2. The method of claim 1, wherein said antibody comprises a heavy chain variable region consisting of amino acid sequence SEQ ID NO: 16, and a light chain variable region consisting of amino acid sequence SEQ ID NO: 19 or SEQ ID NO: 20.

3. A method of treating a subject with a myeloid leukemia comprising administering to said subject an antibody, wherein the antibody binds to VLQELNVTV (SEQ ID NO:45) when bound by an HLA-A2 receptor, said antibody comprises a heavy chain variable region comprising CDRs consisting of amino acid sequences SEQ ID NOS: 3, 60 and 5 respectively, and a light chain variable region comprising CDRs consisting of amino acid sequences SEQ ID NOS: 8, 9 and 10 respectively, wherein said antibody further comprises a heavy chain constant region which is a human gamma-1 heavy chain constant region and a light chain constant region which is a human kappa light chain constant region.

4. The method of claim 3, wherein the antibody comprises a heavy chain comprising a heavy chain variable region consisting of amino acid sequence SEQ ID NO: 16 and a heavy chain constant region which is a human gamma-1 heavy chain constant region, and a light chain comprising a light chain variable region consisting of amino acid sequence SEQ ID NO: 19 and a light chain constant region which is a human kappa light chain constant region.

5. The method of claim 4, wherein the antibody comprises a heavy chain comprising a heavy chain variable region consisting of amino acid sequence SEQ ID NO: 16 and the heavy chain constant region consisting of residues 144-473 in the amino acid sequence SEQ ID NO: 38, and a light chain comprising a light chain variable region consisting of amino acid sequence SEQ ID NO: 19 and a light chain constant region consisting of residues 128-234 in amino acid sequence SEQ ID NO: 42.

6. The method of claim 3, wherein the antibody comprises a heavy chain comprising a heavy chain variable region consisting of amino acid sequence SEQ ID NO: 16 and a heavy chain constant region which is a human gamma-1 heavy chain constant region, and a light chain comprising a light chain variable region consisting of amino acid sequence SEQ ID NO: 20 and a light chain constant region which is a human kappa light chain constant region.

7. The method of claim 6, wherein the antibody comprises a heavy chain comprising a heavy chain variable region consisting of amino acid sequence SEQ ID NO: 16 and the heavy chain constant region consisting of residues 144-473 in the amino acid sequence SEQ ID NO: 38, and a light chain comprising a light chain variable region consisting of amino acid sequence SEQ ID NO: 20 and a light chain constant region consisting of residues 128-234 in the amino acid sequence SEQ ID NO: 42.

8. The method of claim 1, wherein said myeloid leukemia is recurrent.

9. The method of claim 7, wherein said myeloid leukemia is recurrent.

\* \* \* \* \*

SEQUENCE LISTING

```
<160> NUMBER OF SEQ ID NOS: 60

<210> SEQ ID NO 1
<211> LENGTH: 429
<212> TYPE: DNA
<213> ORGANISM: Mus musculus

<400> SEQUENCE: 1
atgaacttcg ggctcagctt gatttcctg gccctcattt taaaaggtgt ccagtgtgag      60
gtgcagctgg tggagtctgg gggagactta gtgaagcctg agggtccct gaaactctcc     120 tgtgcagcct ctggattcac tttcagtgga tatggcatgt cttgggttcg ccagactcca    180
gacaagaggc tggagtgggt cgcaaccatt agtagtggtg gtagttacac ctactatcca    240
gacagtgtga aggggcgatt caccatctcc agagacaatg ccaagaacac cctgtacctg    300
caaatgagca gtctgaagtc tgaagacaca gccatgtatt actgtgcaag acatgagggg    360
ggttactacg gtagtagccc tgcctggttt gtttactggg gccaaggac tctggtcact    420 ctctctgca                                                            429

<210> SEQ ID NO 2
<211> LENGTH: 143
<212> TYPE: PRT
<213> ORGANISM: Mus musculus

<400> SEQUENCE: 2

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Gly Tyr Gly Met Ser Trp Val Arg Gln Thr Pro Asp Lys Arg Leu
```

```
            50                  55                  60
Glu Trp Val Ala Thr Ile Ser Ser Gly Gly Ser Tyr Thr Tyr Tyr Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
            100                 105                 110

Tyr Tyr Cys Ala Arg His Glu Gly Tyr Tyr Gly Ser Ser Pro Ala
        115                 120                 125

Trp Phe Val Tyr Trp Gly Gln Gly Thr Leu Val Thr Leu Ser Ala
    130                 135                 140

<210> SEQ ID NO 3
<211> LENGTH: 5
<212> TYPE: PRT
<213> ORGANISM: Mus musculus

<400> SEQUENCE: 3

Gly Tyr Gly Met Ser
1               5

<210> SEQ ID NO 4
<211> LENGTH: 5
<212> TYPE: PRT
<213> ORGANISM: Mus musculus

<400> SEQUENCE: 4

Gly Tyr Gly Met Ser
1               5

<210> SEQ ID NO 5
<211> LENGTH: 15
<212> TYPE: PRT
<213> ORGANISM: Mus musculus

<400> SEQUENCE: 5

His Glu Gly Gly Tyr Tyr Gly Ser Ser Pro Ala Trp Phe Val Tyr
1               5                   10                  15

<210> SEQ ID NO 6
<211> LENGTH: 381
<212> TYPE: DNA
<213> ORGANISM: Mus musculus

<400> SEQUENCE: 6
atggagtcac agattcaggt ctttgtattc gtgtttctct ggttgtctgg tgttgacgga      60
gacattgtga tgacccagtc tcacaaattc atgtccacat cagtaggaga cagggtcagc    120
atcacctgca aggccagtca ggatgtgagt actgctgtag cctggtatca acagaaacca    180
ggacaatctc ctaaactgct gatttactcg acatcctacc ggtacactgg agtccctgat    240
cgcttcactg gcagtggatc tgggacggtt tcacttttca ccatcaacag tgtccaggct    300
gaagacctgg cagtttatta ctgtcagcaa cattttatta ctcctccgac gttcggtgga    360
ggcaccaagc tggaaatcaa a                                              381

<210> SEQ ID NO 7
<211> LENGTH: 127
<212> TYPE: PRT
<213> ORGANISM: Mus musculus

<400> SEQUENCE: 7
```

```
Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Ser Thr Ala Val Ala Trp Tyr Gln Gln Lys Pro Gly Gln Ser Pro
    50                  55                  60

Lys Leu Leu Ile Tyr Ser Thr Ser Tyr Arg Tyr Thr Gly Val Pro Asp
65                  70                  75                  80

Arg Phe Thr Gly Ser Gly Ser Gly Thr Val Phe Thr Phe Thr Ile Asn
                85                  90                  95

Ser Val Gln Ala Glu Asp Leu Ala Val Tyr Tyr Cys Gln Gln His Phe
                100                 105                 110

Ile Thr Pro Pro Thr Phe Gly Gly Gly Thr Lys Leu Glu Ile Lys
            115                 120                 125
```

<210> SEQ ID NO 8
<211> LENGTH: 11
<212> TYPE: PRT
<213> ORGANISM: Mus musculus

<400> SEQUENCE: 8

```
Lys Ala Ser Gln Asp Val Ser Thr Ala Val Ala
1               5                   10
```

<210> SEQ ID NO 9
<211> LENGTH: 7
<212> TYPE: PRT
<213> ORGANISM: Mus musculus

<400> SEQUENCE: 9

```
Ser Thr Ser Tyr Arg Tyr Thr
1               5
```

<210> SEQ ID NO 10
<211> LENGTH: 9
<212> TYPE: PRT
<213> ORGANISM: Mus musculus

<400> SEQUENCE: 10

```
Gln Gln His Phe Ile Thr Pro Pro Thr
1               5
```

<210> SEQ ID NO 11
<211> LENGTH: 463
<212> TYPE: DNA
<213> ORGANISM: Artificial Sequence
<220> FEATURE:
<223> OTHER INFORMATION: Synthetic primer

<400> SEQUENCE: 11

```
actagtacca ccatgaactt cgggctcagc ttgattttcc tggccctcat tttaaaaggt      60
gtccagtgtg aggtgcagct ggtggagtct gggggagact tagtgaagcc tggagggtcc     120
ctgaaactct cctgtgcagc ctctggattc actttcagtg gatatggcat gtcttgggtt     180
cgccagactc cagacaagag gctggagtgg gtcgcaacca ttagtagtgg tggtagttac     240
acctactatc cagacagtgt gaagggccga ttcaccatct ccagagacaa tgccaagaac     300
accctgtacc tgcaaatgag cagtctgaag tctgaagaca cagccatgta ttactgtgca     360
```

```
agacatgagg ggggttacta cggtagtagc cctgcctggt ttgtttactg gggccaaggg      420
actctggtca ctctctctgc aggtgagtcc taacttcaag ctt                        463
```

<210> SEQ ID NO 12
<211> LENGTH: 143
<212> TYPE: PRT
<213> ORGANISM: Artificial Sequence
<220> FEATURE:
<223> OTHER INFORMATION: Synthetic peptide

<400> SEQUENCE: 12

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Gly Tyr Gly Met Ser Trp Val Arg Gln Thr Pro Asp Lys Arg Leu
    50                  55                  60

Glu Trp Val Ala Thr Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Glu Gly Gly Tyr Tyr Gly Ser Ser Pro Ala
        115                 120                 125

Trp Phe Val Tyr Trp Gly Gln Gly Thr Leu Val Thr Leu Ser Ala
    130                 135                 140
```

<210> SEQ ID NO 13
<211> LENGTH: 416
<212> TYPE: DNA
<213> ORGANISM: Artificial Sequence
<220> FEATURE:
<223> OTHER INFORMATION: Synthetic primer

<400> SEQUENCE: 13

```
gctagcacca ccatggagtc acagattcag gtctttgtat tcgtgtttct ctggttgtct       60
ggtgttgacg gagacattgt gatgacccag tctcacaaat tcatgtccac atcagtagga     120
gacagggtca gcatcacctg caaggccagt caggatgtga gtactgctgt agcctggtat     180
caacagaaac caggacaatc tcctaaactg ctgatttact cgacatccta ccggtacact     240
ggagtccctg atcgcttcac tggcagtgga tctgggacgg ttttcacttt caccatcaac     300
agtgtccagg ctgaagacct ggcagtttat tactgtcagc aacatttat tactcctccg      360 acgttcggtg aggcaccaa gctggaaatc aaacgtaagt agaatccaaa gaattc          416
```

<210> SEQ ID NO 14
<211> LENGTH: 127
<212> TYPE: PRT
<213> ORGANISM: Artificial Sequence
<220> FEATURE:
<223> OTHER INFORMATION: Synthetic peptide

<400> SEQUENCE: 14

```
Met Glu Ser Gln Ile Gln Val Phe Val Phe Val Phe Leu Trp Leu Ser
1               5                   10                  15
```

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
            35                  40                  45

Val Ser Thr Ala Val Ala Trp Tyr Gln Gln Lys Pro Gly Gln Ser Pro
    50                  55                  60

Lys Leu Leu Ile Tyr Ser Thr Ser Tyr Arg Tyr Thr Gly Val Pro Asp
65                  70                  75                  80

Arg Phe Thr Gly Ser Gly Ser Gly Thr Val Phe Thr Phe Thr Ile Asn
                85                  90                  95

Ser Val Gln Ala Glu Asp Leu Ala Val Tyr Tyr Cys Gln Gln His Phe
            100                 105                 110

Ile Thr Pro Pro Thr Phe Gly Gly Gly Thr Lys Leu Glu Ile Lys
            115                 120                 125

<210> SEQ ID NO 15
<211> LENGTH: 124
<212> TYPE: PRT
<213> ORGANISM: Mus musculus

<400> SEQUENCE: 15

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Gly Gly Tyr Tyr Gly Ser Ser Pro Ala Trp Phe Val
            100                 105                 110

Tyr Trp Gly Gln Gly Thr Leu Val Thr Leu Ser Ala
            115                 120

<210> SEQ ID NO 16
<211> LENGTH: 124
<212> TYPE: PRT
<213> ORGANISM: Artificial Sequence
<220> FEATURE:
<223> OTHER INFORMATION: Synthetic peptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
            35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys 85                  90                  95
Ala Arg His Glu Gly Gly Tyr Tyr Gly Ser Ser Pro Ala Trp Phe Val
                100                 105                 110
Tyr Trp Gly Gln Gly Thr Met Val Thr Val Ser Ser
        115                 120

<210> SEQ ID NO 17
<211> LENGTH: 87
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Trp Val
            20                  25                  30
Arg Gln Ala Pro Gly Lys Gly Leu Glu Trp Val Ala Arg Phe Thr Ile
        35                  40                  45
Ser Arg Asp Asn Ala Lys Asn Ser Leu Tyr Leu Gln Met Asn Ser Leu
    50                  55                  60
Arg Ala Glu Asp Thr Ala Val Tyr Tyr Cys Ala Arg Trp Gly Gln Gly
65                  70                  75                  80
Thr Met Val Thr Val Ser Ser
                85

<210> SEQ ID NO 18
<211> LENGTH: 107
<212> TYPE: PRT
<213> ORGANISM: Mus musculus

<400> SEQUENCE: 18

Asp Ile Val Met Thr Gln Ser His Lys Phe Met Ser Thr Ser Val Gly
1               5                   10                  15
Asp Arg Val Ser Ile Thr Cys Lys Ala Ser Gln Asp Val Ser Thr Ala
            20                  25                  30
Val Ala Trp Tyr Gln Gln Lys Pro Gly Gln Ser Pro Lys Leu Leu Ile
        35                  40                  45
Tyr Ser Thr Ser Tyr Arg Tyr Thr Gly Val Pro Asp Arg Phe Thr Gly
    50                  55                  60
Ser Gly Ser Gly Thr Val Phe Thr Phe Thr Ile Asn Ser Val Gln Ala
65                  70                  75                  80
Glu Asp Leu Ala Val Tyr Tyr Cys Gln Gln His Phe Ile Thr Pro Pro
                85                  90                  95
Thr Phe Gly Gly Gly Thr Lys Leu Glu Ile Lys
                100                 105

<210> SEQ ID NO 19
<211> LENGTH: 107
<212> TYPE: PRT
<213> ORGANISM: Artificial Sequence
<220> FEATURE:
<223> OTHER INFORMATION: Synthetic peptide

<400> SEQUENCE: 19

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
                35                  40                  45

Tyr Ser Thr Ser Tyr Arg Tyr Thr Gly Val Pro Ser Arg Phe Ser Gly
        50                  55                  60

Ser Gly Ser Gly Thr Val Phe Thr Phe Thr Ile Ser Ser Leu Gln Pro
65                  70                  75                  80

Glu Asp Ile Ala Thr Tyr Tyr Cys Gln Gln His Phe Ile Thr Pro Pro
                85                  90                  95

Thr Phe Gly Gly Gly Thr Lys Val Glu Ile Lys
                100                 105

<210> SEQ ID NO 20
<211> LENGTH: 107
<212> TYPE: PRT
<213> ORGANISM: Artificial Sequence
<220> FEATURE:
<223> OTHER INFORMATION: Synthetic peptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
                35                  40                  45

Tyr Ser Thr Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Phe Ile Thr Pro Pro
                85                  90                  95

Thr Phe Gly Gly Gly Thr Lys Val Glu Ile Lys
                100                 105

<210> SEQ ID NO 21
<211> LENGTH: 80
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
                20                  25                  30

Pro Lys Leu Leu Ile Tyr Gly Val Pro Ser Arg Phe Ser Gly Ser Gly
        35                  40                  45

Ser Gly Thr Asp Phe Thr Phe Thr Ile Ser Ser Leu Gln Pro Glu Asp
    50                  55                  60

Ile Ala Thr Tyr Tyr Cys Phe Gly Gly Gly Thr Lys Val Glu Ile Lys
65                  70                  75                  80

<210> SEQ ID NO 22
<211> LENGTH: 463
<212> TYPE: DNA
<213> ORGANISM: Artificial Sequence
<220> FEATURE:
<223> OTHER INFORMATION: Synthetic primer

<400> SEQUENCE: 22

-continued

```
actagtacca ccatgaactt cgggctcagc ttgattttcc tggccctcat tttaaaagga    60
gtccagtgtg aagtgcagct ggtggagtct ggcggaggcc tcgtgcagcc tggaggatcc   120
ctgagactct cctgtgcagc ctctggattc actttcagcg atatggcat gtcttgggtt    180 cgccaggctc caggcaaggg gctcgaatgg gtcgcaacca ttagtagtgg tggtagttac   240
acctactatc cagacagtgt gaaggggcga ttcaccatct ccagagacaa tgccaagaac   300
tcactgtacc tgcaaatgaa cagtctgaga gccgaagaca cagccgtgta ttactgtgca   360
agacatgagg gaggctacta cggtagtagc cctgcctggt ttgtttactg gggccaaggg   420
actatggtca ctgtctcttc aggtaagatg ggcttccaag ctt                     463
```

<210> SEQ ID NO 23
<211> LENGTH: 143
<212> TYPE: PRT
<213> ORGANISM: Artificial Sequence
<220> FEATURE:
<223> OTHER INFORMATION: Synthetic peptide

<400> SEQUENCE: 23

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Leu Val Gln
                20                  25                  30

Pro Gly Gly Ser Leu Arg Leu Ser Cys Ala Ala Ser Gly Phe Thr Phe
        35                  40                  45

Ser Gly Tyr Gly Met Ser Trp Val Arg Gln Ala Pro Gly Lys Gly Leu
    50                  55                  60

Glu Trp Val Ala Thr Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg His Glu Gly Gly Tyr Tyr Gly Ser Ser Pro Ala
        115                 120                 125

Trp Phe Val Tyr Trp Gly Gln Gly Thr Met Val Thr Val Ser Ser
    130                 135                 140
```

<210> SEQ ID NO 24
<211> LENGTH: 416
<212> TYPE: DNA
<213> ORGANISM: Artificial Sequence
<220> FEATURE:
<223> OTHER INFORMATION: Synthetic primer

<400> SEQUENCE: 24

```
gctagcacca ccatggagtc acagattcag gtctttgtat tcgtgtttct ctggttgtct    60
ggtgttgacg gagacattca gatgacccag tctccatcct ccctgtccgc atcagtagga   120
gacagggtca ccatcacctg caaggccagt caggatgtga gtactgctgt ggcctggtac   180
caacagaaac caggaaaagc ccctaaactg ctgatttact ccacatccta ccggtacact   240
ggagtccctt cacgcttcag tggcagtgga tctgggaccg ttttcacttt caccatcagc   300
agtctgcagc ctgaagacat tgcaacatat tactgtcagc aacatttat tactcctccc    360 acattcggtg aggcaccaa agtggaaatc aaacgtaagt gcactttcct gaattc        416
```

<210> SEQ ID NO 25

<211> LENGTH: 127
<212> TYPE: PRT
<213> ORGANISM: Artificial Sequence
<220> FEATURE:
<223> OTHER INFORMATION: Synthetic peptide

<400> SEQUENCE: 25

```
Met Glu Ser Gln Ile Gln Val Phe Val Phe Val Phe Leu Trp Leu Ser
1               5                   10                  15

Gly Val Asp Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Thr Ser Tyr Arg Tyr Thr Gly Val Pro Ser
65                  70                  75                  80

Arg Phe Ser Gly Ser Gly Ser Gly Thr Val Phe Thr Phe Thr Ile Ser
                85                  90                  95

Ser Leu Gln Pro Glu Asp Ile Ala Thr Tyr Tyr Cys Gln Gln His Phe
            100                 105                 110

Ile Thr Pro Pro Thr Phe Gly Gly Gly Thr Lys Val Glu Ile Lys
        115                 120                 125
```

<210> SEQ ID NO 26
<211> LENGTH: 416
<212> TYPE: DNA
<213> ORGANISM: Artificial Sequence
<220> FEATURE:
<223> OTHER INFORMATION: Synthetic primer

<400> SEQUENCE: 26

```
gctagcacca ccatggagtc acagattcag gtctttgtat tcgtgtttct ctggttgtct    60
ggtgttgacg gagacattca gatgacccag tctccatcct ccctgtccgc atcagtagga   120
gacagggtca ccatcacctg caaggccagt caggatgtga gtactgctgt ggcctggtac   180
caacagaaac aggaaaaagc ccctaaactg ctgatttact ccacatccta ccggtacact   240
ggagtccctt cacgcttcag tggcagtgga tctgggaccg atttcacttt caccatcagc   300
agtctgcagc ctgaagacat tgcaacatat tactgtcagc aacattttat tactcctccc   360
acattcggtg gaggcaccaa agtggaaatc aaacgtaagt gcactttcct gaattc       416
```

<210> SEQ ID NO 27
<211> LENGTH: 127
<212> TYPE: PRT
<213> ORGANISM: Artificial Sequence
<220> FEATURE:
<223> OTHER INFORMATION: Synthetic peptide

<400> SEQUENCE: 27

```
Met Glu Ser Gln Ile Gln Val Phe Val Phe Val Phe Leu Trp Leu Ser
1               5                   10                  15

Gly Val Asp Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Thr Ser Tyr Arg Tyr Thr Gly Val Pro Ser
```

```
            65                  70                  75                  80
Arg Phe Ser Gly Ser Gly Ser Gly Thr Asp Phe Thr Phe Thr Ile Ser
                    85                  90                  95
Ser Leu Gln Pro Glu Asp Ile Ala Thr Tyr Tyr Cys Gln Gln His Phe
                   100                 105                 110
Ile Thr Pro Pro Thr Phe Gly Gly Gly Thr Lys Val Glu Ile Lys
                   115                 120                 125
```

<210> SEQ ID NO 28
<211> LENGTH: 24
<212> TYPE: DNA
<213> ORGANISM: Artificial Sequence
<220> FEATURE:
<223> OTHER INFORMATION: Synthetic primer

<400> SEQUENCE: 28
gaaccgtcag atcgcctgga gacg                                              24

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
tgaaagatga gctggaggac                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
ctttcttgtc caccttggtg                                                   20

<210> SEQ ID NO 31
<211> LENGTH: 19
<212> TYPE: DNA
<213> ORGANISM: Artificial Sequence
<220> FEATURE:
<223> OTHER INFORMATION: Synthetic primer

<400> SEQUENCE: 31
gctgtcctac agtcctcag                                                    19

<210> SEQ ID NO 32
<211> LENGTH: 18
<212> TYPE: DNA
<213> ORGANISM: Artificial Sequence
<220> FEATURE:
<223> OTHER INFORMATION: Synthetic primer

<400> SEQUENCE: 32
acgtgccaag catcctcg                                                     18

<210> SEQ ID NO 33
<211> LENGTH: 1422
<212> TYPE: DNA
<213> ORGANISM: Artificial Sequence
<220> FEATURE:
<223> OTHER INFORMATION: Synthetic primer

<400> SEQUENCE: 33

```
atgaacttcg ggctcagctt gatttcctg gccctcattt taaaaggtgt ccagtgtgag       60
gtgcagctgg tggagtctgg gggagactta gtgaagcctg agggtccct gaaactctcc      120
tgtgcagcct ctggattcac tttcagtgga tatggcatgt cttgggttcg ccagactcca     180
gacaagaggc tggagtgggt cgcaaccatt agtagtggtg gtagttacac ctactatcca     240
gacagtgtga aggggcgatt caccatctcc agagacaatg ccaagaacac cctgtacctg     300
caaatgagca gtctgaagtc tgaagacaca gccatgtatt actgtgcaag acatgagggg    360
ggttactacg gtagtagccc tgcctggttt gtttactggg gccaagggac tctggtcact     420
ctctctgcag cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta    600
cagtcctcag gactctactc cctcagcagc gtggtgaccg tgccctccag cagcttgggc     660
acccagacct acatctgcaa cgtgaatcac aagcccagca caccaaggt ggacaagaaa      720
gttgagccca atcttgtga caaaactcac acatgcccac cgtgcccagc acctgaactc      780
ctgggggac cgtcagtctt cctcttcccc ccaaaaccca aggacaccct catgatctcc      840
cggacccctg aggtcacatg cgtggtggtg gacgtgagcc acgaagaccc tgaggtcaag    900
ttcaactggt acgtggacgg cgtggaggtg cataatgcca agacaaagcc gcgggaggag    960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagccccga gaaccacagg tgtacaccct gcccccatcc   1140
cgggatgagc tgaccaagaa ccaggtcagc ctgacctgcc tggtcaaagg cttctatccc   1200
agcgacatcg ccgtggagtg ggagagcaat gggcagccgg agaacaacta caagaccacg   1260
cctcccgtgc tggactccga cggctccttc ttcctctaca gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                        1422
```

<210> SEQ ID NO 34
<211> LENGTH: 473
<212> TYPE: PRT
<213> ORGANISM: Artificial Sequence
<220> FEATURE:
<223> OTHER INFORMATION: Synthetic peptide

<400> SEQUENCE: 34

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Gly Tyr Gly Met Ser Trp Val Arg Gln Thr Pro Asp Lys Arg Leu
    50                  55                  60

Glu Trp Val Ala Thr Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
```

```
                100             105             110
Tyr Tyr Cys Ala Arg His Glu Gly Gly Tyr Tyr Gly Ser Ser Pro Ala
        115                 120                 125
Trp Phe Val Tyr Trp Gly Gln Gly Thr Leu Val Thr Leu Ser Ala Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
                180                 185                 190
Val His Thr Phe Pro Ala Val Leu Gln Ser Ser Gly Leu Tyr Ser Leu
                195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
                260                 265                 270
Pro Lys Asp Thr Leu Met Ile Ser Arg Thr Pro Glu Val Thr Cys Val
                275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
                340                 345                 350
Ala Leu Pro Ala Pro Ile Glu Lys Thr Ile Ser Lys Ala Lys Gly Gln
                355                 360                 365
Pro Arg Glu Pro Gln Val Tyr Thr Leu Pro Pro Ser Arg Asp Glu Leu
370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
                420                 425                 430
Tyr Ser Lys Leu Thr Val Asp Lys Ser Arg Trp Gln Gln Gly Asn Val
                435                 440                 445
Phe Ser Cys Ser Val Met His Glu Ala Leu His Asn His Tyr Thr Gln
450                 455                 460
Lys Ser Leu Ser Leu Ser Pro Gly Lys
465                 470

<210> SEQ ID NO 35
<211> LENGTH: 705
<212> TYPE: DNA
<213> ORGANISM: Artificial Sequence
<220> FEATURE:
<223> OTHER INFORMATION: Synthetic primer
```

<400> SEQUENCE: 35

```
atggagtcac agattcaggt ctttgtattc gtgtttctct ggttgtctgg tgttgacgga      60
gacattgtga tgacccagtc tcacaaattc atgtccacat cagtaggaga cagggtcagc     120
atcacctgca aggccagtca ggatgtgagt actgctgtag cctggtatca acagaaacca     180
ggacaatctc ctaaactgct gatttactcg acatcctacc ggtacactgg agtccctgat     240
cgcttcactg gcagtggatc tgggacggtt tcactttca ccatcaacag tgtccaggct      300
gaagacctgg cagttattta ctgtcagcaa cattttatta ctcctccgac gttcggtgga     360
ggcaccaagc tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac agggagagt gttag                      705
```

<210> SEQ ID NO 36
<211> LENGTH: 234
<212> TYPE: PRT
<213> ORGANISM: Artificial Sequence
<220> FEATURE:
<223> OTHER INFORMATION: Synthetic peptide

<400> SEQUENCE: 36

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Lys Leu Leu Ile Tyr Ser Thr Ser Tyr Arg Tyr Thr Gly Val Pro Asp
65                  70                  75                  80

Arg Phe Thr Gly Ser Gly Ser Gly Thr Val Phe Thr Phe Thr Ile Asn
                85                  90                  95

Ser Val Gln Ala Glu Asp Leu Ala Val Tyr Tyr Cys Gln Gln His Phe
            100                 105                 110

Ile Thr Pro Pro Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys

<210> SEQ ID NO 37
<211> LENGTH: 1422
<212> TYPE: DNA
<213> ORGANISM: Artificial Sequence
<220> FEATURE:
<223> OTHER INFORMATION: Synthetic primer

<400> SEQUENCE: 37

```
atgaacttcg ggctcagctt gattttcctg gccctcattt taaaaggagt ccagtgtgaa      60
gtgcagctgg tggagtctgg cggaggcctc gtgcagcctg gaggatccct gagactctcc     120
tgtgcagcct ctggattcac tttcagcgga tatggcatgt cttgggttcg ccaggctcca     180
ggcaaggggc tcgaatgggt cgcaaccatt agtagtggtg gtagttacac ctactatcca     240
gacagtgtga aggggcgatt caccatctcc agagacaatg ccaagaactc actgtacctg     300
caaatgaaca gtctgagagc cgaagacaca gccgtgtatt actgtgcaag acatgaggga     360
ggctactacg gtagtagccc tgcctggttt gtttactggg gccaagggac tatggtcact     420
gtctcttcag cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acccagacct acatctgcaa cgtgaatcac aagcccagca acaccaaggt ggacaagaaa     720
gttgagccca aatcttgtga caaaactcac acatgcccac cgtgcccagc acctgaactc     780
ctggggggac cgtcagtctt cctcttcccc ccaaaaccca aggacaccct catgatctcc     840
cggacccctg aggtcacatg cgtggtggtg gacgtgagcc acgaagaccc tgaggtcaag     900
ttcaactggt acgtggacgg cgtggaggtg cataatgcca agacaaagcc gcgggaggag     960
cagtacaaca gcacgtaccg tgtggtcagc gtcctcaccg tcctgcacca ggactggctg    1020
aatggcaagg agtacaagtg caaggtctcc aacaaagccc tcccagcccc catcgagaaa    1080
accatctcca aagccaaagg gcagccccga gaaccacagg tgtacaccct gcccccatcc    1140
cgggatgagc tgaccaagaa ccaggtcagc ctgacctgcc tggtcaaagg cttctatccc    1200
agcgacatcg ccgtggagtg ggagagcaat gggcagccgg agaacaacta caagaccacg    1260
cctcccgtgc tggactccga cggctccttc ttcctctaca gcaagctcac cgtggacaag    1320
agcaggtggc agcaggggaa cgtcttctca tgctccgtga tgcatgaggc tctgcacaac    1380
cactacacgc agaagagcct ctccctgtct ccgggtaaat ga                       1422
```

<210> SEQ ID NO 38
<211> LENGTH: 473
<212> TYPE: PRT
<213> ORGANISM: Artificial Sequence
<220> FEATURE:
<223> OTHER INFORMATION: Synthetic peptide

<400> SEQUENCE: 38

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45
```

```
Ser Gly Tyr Gly Met Ser Trp Val Arg Gln Ala Pro Gly Lys Gly Leu
 50                  55                  60
Glu Trp Val Ala Thr Ile Ser Ser Gly Gly Ser Tyr Thr Tyr Tyr Pro
 65                  70                  75                  80
Asp Ser Val Lys Gly Arg Phe Thr Ile Ser Arg Asp Asn Ala Lys Asn
                 85                  90                  95
Ser Leu Tyr Leu Gln Met Asn Ser Leu Arg Ala Glu Asp Thr Ala Val
             100                 105                 110
Tyr Tyr Cys Ala Arg His Glu Gly Tyr Tyr Gly Ser Ser Pro Ala
             115                 120                 125
Trp Phe Val Tyr Trp Gly Gln Gly Thr Met Val Thr Val Ser Ser Ala
     130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                 165                 170                 175
Pro Glu Pro Val Thr Val Ser Trp Asn Ser Gly Ala Leu Thr Ser Gly
             180                 185                 190
Val His Thr Phe Pro Ala Val Leu Gln Ser Ser Gly Leu Tyr Ser Leu
         195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                 245                 250                 255
Ala Pro Glu Leu Leu Gly Gly Pro Ser Val Phe Leu Phe Pro Pro Lys
             260                 265                 270
Pro Lys Asp Thr Leu Met Ile Ser Arg Thr Pro Glu Val Thr Cys Val
         275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                 325                 330                 335
Gln Asp Trp Leu Asn Gly Lys Glu Tyr Lys Cys Lys Val Ser Asn Lys
             340                 345                 350
Ala Leu Pro Ala Pro Ile Glu Lys Thr Ile Ser Lys Ala Lys Gly Gln
         355                 360                 365
Pro Arg Glu Pro Gln Val Tyr Thr Leu Pro Pro Ser Arg Asp Glu Leu
370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                 405                 410                 415
Tyr Lys Thr Thr Pro Pro Val Leu Asp Ser Asp Gly Ser Phe Phe Leu
             420                 425                 430
Tyr Ser Lys Leu Thr Val Asp Lys Ser Arg Trp Gln Gln Gly Asn Val
         435                 440                 445
Phe Ser Cys Ser Val Met His Glu Ala Leu His Asn His Tyr Thr Gln
450                 455                 460
Lys Ser Leu Ser Leu Ser Pro Gly Lys
```

<210> SEQ ID NO 39
<211> LENGTH: 705
<212> TYPE: DNA
<213> ORGANISM: Artificial Sequence
<220> FEATURE:
<223> OTHER INFORMATION: Synthetic primer

<400> SEQUENCE: 39

```
atggagtcac agattcaggt ctttgtattc gtgtttctct ggttgtctgg tgttgacgga    60
gacattcaga tgacccagtc tccatcctcc ctgtccgcat cagtaggaga cagggtcacc   120
atcacctgca aggccagtca ggatgtgagt actgctgtgg cctggtacca acagaaacca   180
ggaaaagccc ctaaactgct gatttactcc acatcctacc ggtacactgg agtcccttca   240
cgcttcagtg gcagtggatc tgggaccgtt ttcactttca ccatcagcag tctgcagcct   300
gaagacattg caacatatta ctgtcagcaa cattttatta ctcctcccac attcggtgga   360
ggcaccaaag tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga aaacacaaa gtctacgcct gcgaagtcac ccatcagggc   660
ctgagctcgc ccgtcacaaa gagcttcaac aggggagagt gttag              705
```

<210> SEQ ID NO 40
<211> LENGTH: 234
<212> TYPE: PRT
<213> ORGANISM: Artificial Sequence
<220> FEATURE:
<223> OTHER INFORMATION: Synthetic peptide

<400> SEQUENCE: 40

```
Met Glu Ser Gln Ile Gln Val Phe Val Phe Val Phe Leu Trp Leu Ser
1               5                   10                  15

Gly Val Asp Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Thr Ser Tyr Arg Tyr Thr Gly Val Pro Ser
65                  70                  75                  80

Arg Phe Ser Gly Ser Gly Ser Gly Thr Val Phe Thr Phe Thr Ile Ser
                85                  90                  95

Ser Leu Gln Pro Glu Asp Ile Ala Thr Tyr Tyr Cys Gln Gln His Phe
            100                 105                 110

Ile Thr Pro Pro Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 41
<211> LENGTH: 705
<212> TYPE: DNA
<213> ORGANISM: Artificial Sequence
<220> FEATURE:
<223> OTHER INFORMATION: Synthetic primer

<400> SEQUENCE: 41

```
atggagtcac agattcaggt ctttgtattc gtgtttctct ggttgtctgg tgttgacgga     60
gacattcaga tgacccagtc tccatcctcc ctgtccgcat cagtaggaga cagggtcacc    120
atcacctgca aggccagtca ggatgtgagt actgctgtgg cctggtacca acagaaacca    180
ggaaaagccc ctaaactgct gatttactcc acatcctacc ggtacactgg agtcccttca    240
cgcttcagtg gcagtggatc tgggaccgat ttcactttca ccatcagcag tctgcagcct    300
gaagacattg caacatatta ctgtcagcaa cattttatta ctcctcccac attcggtgga    360
ggcaccaaag tggaaatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag cacccctacg    600
ctgagcaaag cagactacga gaaacacaaa gtctacgcct gcgaagtcac ccatcagggc    660
ctgagctcgc ccgtcacaaa gagcttcaac aggggagagt gttag                    705
```

<210> SEQ ID NO 42
<211> LENGTH: 234
<212> TYPE: PRT
<213> ORGANISM: Artificial Sequence
<220> FEATURE:
<223> OTHER INFORMATION: Synthetic peptide

<400> SEQUENCE: 42

Met Glu Ser Gln Ile Gln Val Phe Val Phe Val Phe Leu Trp Leu Ser
1               5                   10                  15

Gly Val Asp Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Thr Ser Tyr Arg Tyr Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Gln Gln His Phe
            100                 105                 110

Ile Thr Pro Pro Thr Phe Gly Gly Gly Thr Lys Val Glu Ile Lys Arg
        115                 120                 125

```
Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 43
<211> LENGTH: 1422
<212> TYPE: DNA
<213> ORGANISM: Artificial Sequence
<220> FEATURE:
<223> OTHER INFORMATION: Synthetic primer

<400> SEQUENCE: 43

```
atgaacttcg ggctcagctt gattttcctg gccctcattt taaaaggagt ccagtgtgaa      60
gtgcagctgg tggagtctgg cggaggcctc gtgcagcctg gaggatccct gagactctcc     120
tgtgcagcct ctggattcac tttcagcgga tatggcatgt cttgggttcg ccaggctcca     180
ggcaaggggc tcgaatgggt cgcaaccatt agtagtggtg gtagttacac ctactatcca     240
gacagtgtga aggggcgatt caccatctcc agagacaatg ccaagaactc actgtacctg     300
caaatgaaca gtctgagagc cgaagacaca gccgtgtatt actgtgcaag acatgaggga     360
ggctactacg tagtagccc tgcctggttt gtttactggg ccaagggac tatggtcact     420
gtctcttcag cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acccagacct acatctgcaa cgtgaatcac aagcccagca caccaaggt ggacaagaaa     720
gttgagccca aatcttgtga caaaactcac acatgcccac cgtgcccagc acctgaagct     780
gctggaggac cgtcagtctt cctcttcccc ccaaaaccca aggacaccct catgatctcc     840
cggacccctg aggtcacatg cgtggtggtg gacgtgagcc acgaagaccc tgaggtcaag     900
ttcaactggt acgtggacgg cgtggaggtg cataatgcca agacaaagcc gcgggaggag     960
cagtacaaca gcacgtaccg tgtggtcagc gtcctcaccg tcctgcacca ggactggctg    1020
aatggcaagg agtacaagtg caaggtctcc aacaaagccc tcccagcccc catcgagaaa    1080
accatctcca aagccaaagg gcagccccga gaaccacagg tgtacaccct gcccccatcc    1140
cgggatgagc tgaccaagaa ccaggtcagc ctgacctgcc tggtcaaagg cttctatccc    1200
agcgacatcg ccgtggagtg ggagagcaat gggcagccgg agaacaacta caagaccacg    1260
cctcccgtgc tggactccga cggctccttc ttcctctaca gcaagctcac cgtggacaag    1320
agcaggtggc agcaggggaa cgtcttctca tgctccgtga tgcatgaggc tctgcacaac    1380
cactacacgc agaagagcct ctccctgtct ccgggtaaat ga                      1422
```

<210> SEQ ID NO 44
<211> LENGTH: 473
<212> TYPE: PRT
<213> ORGANISM: Artificial Sequence
<220> FEATURE:
<223> OTHER INFORMATION: Synthetic peptide

<400> SEQUENCE: 44

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Gly Tyr Gly Met Ser Trp Val Arg Gln Ala Pro Gly Lys Gly Leu
    50                  55                  60

Glu Trp Val Ala Thr Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg His Glu Gly Gly Tyr Tyr Gly Ser Ser Pro Ala
        115                 120                 125

Trp Phe Val Tyr Trp Gly Gln Gly Thr Met Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365
```

-continued

```
Pro Arg Glu Pro Gln Val Tyr Thr Leu Pro Pro Ser Arg Asp Glu Leu
        370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
    450                 455                 460
Lys Ser Leu Ser Leu Ser Pro Gly Lys
465                 470
```

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Val Leu Gln Glu Leu Asn Val Thr Val
1               5

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
gccagtggat agaccgatgg                                                   20

<210> SEQ ID NO 47
<211> LENGTH: 21
<212> TYPE: DNA
<213> ORGANISM: Artificial Sequence
<220> FEATURE:
<223> OTHER INFORMATION: Synthetic primer

<400> SEQUENCE: 47
gatggataca gttggtgcag c                                                 21

<210> SEQ ID NO 48
<211> LENGTH: 33
<212> TYPE: DNA
<213> ORGANISM: Artificial Sequence
<220> FEATURE:
<223> OTHER INFORMATION: Synthetic primer

<400> SEQUENCE: 48
gcaactagta ccaccatgaa cttcgggctc agc                                    33

<210> SEQ ID NO 49
<211> LENGTH: 45
<212> TYPE: DNA
<213> ORGANISM: Artificial Sequence
<220> FEATURE:
<223> OTHER INFORMATION: Synthetic primer

```
<400> SEQUENCE: 49
cgaaagcttg aagttaggac tcacctgcag agagagtgac cagag            45

<210> SEQ ID NO 50
<211> LENGTH: 33
<212> TYPE: DNA
<213> ORGANISM: Artificial Sequence
<220> FEATURE:
<223> OTHER INFORMATION: Synthetic primer

<400> SEQUENCE: 50
gcagctagca ccaccatgga gtcacagatt cag                         33

<210> SEQ ID NO 51
<211> LENGTH: 45
<212> TYPE: DNA
<213> ORGANISM: Artificial Sequence
<220> FEATURE:
<223> OTHER INFORMATION: Synthetic primer

<400> SEQUENCE: 51
cgagaattct ttggattcta cttacgtttg atttccagct tggtg            45

<210> SEQ ID NO 52
<211> LENGTH: 18
<212> TYPE: DNA
<213> ORGANISM: Artificial Sequence
<220> FEATURE:
<223> OTHER INFORMATION: Synthetic Primer

<400> SEQUENCE: 52
gaccccacca tggctcac                                          18

<210> SEQ ID NO 53
<211> LENGTH: 20
<212> TYPE: DNA
<213> ORGANISM: Artificial Sequence
<220> FEATURE:
<223> OTHER INFORMATION: Synthetic Primer

<400> SEQUENCE: 53
atgggaagga cagacaggag                                        20

<210> SEQ ID NO 54
<211> LENGTH: 20
<212> TYPE: DNA
<213> ORGANISM: Artificial Sequence
<220> FEATURE:
<223> OTHER INFORMATION: Synthetic Primer

<400> SEQUENCE: 54
agcactgcta cgcaggctct                                        20

<210> SEQ ID NO 55
<211> LENGTH: 20
<212> TYPE: DNA
<213> ORGANISM: Artificial Sequence
<220> FEATURE:
<223> OTHER INFORMATION: Synthetic Primer

<400> SEQUENCE: 55
ataagaaaga gaaggtgtgg                                        20

<210> SEQ ID NO 56
<211> LENGTH: 20
```

```
<212> TYPE: DNA
<213> ORGANISM: Artificial Sequence
<220> FEATURE:
<223> OTHER INFORMATION: Synthetic Primer

<400> SEQUENCE: 56
ccagagcaag agagctatcc                                        20

<210> SEQ ID NO 57
<211> LENGTH: 20
<212> TYPE: DNA
<213> ORGANISM: Artificial Sequence
<220> FEATURE:
<223> OTHER INFORMATION: Synthetic Primer

<400> SEQUENCE: 57
ctgtggtggt gaagctgtag                                        20

<210> SEQ ID NO 58
<211> LENGTH: 20
<212> TYPE: DNA
<213> ORGANISM: Artificial Sequence
<220> FEATURE:
<223> OTHER INFORMATION: Synthetic Primer

<400> SEQUENCE: 58
tagacgggaa gctcactggc                                        20

<210> SEQ ID NO 59
<211> LENGTH: 20
<212> TYPE: DNA
<213> ORGANISM: Artificial Sequence
<220> FEATURE:
<223> OTHER INFORMATION: Synthetic Primer

<400> SEQUENCE: 59
aggtccacca ccctgttgct                                        20

<210> SEQ ID NO 60
<211> LENGTH: 17
<212> TYPE: PRT
<213> ORGANISM: Mus musculus

<400> SEQUENCE: 60

Thr Ile Ser Ser Gly Gly Ser Tyr Thr Tyr Tyr Pro Asp Ser Val Lys
1               5                   10                  15

Gly
```